United States Patent
Zhang et al.

(10) Patent No.: US 10,087,486 B2
(45) Date of Patent: Oct. 2, 2018

(54) METHODS FOR PREDICTING AGE AND IDENTIFYING AGENTS THAT INDUCE OR INHIBIT PREMATURE AGING

(71) Applicants: THE REGENTS OF THE UNIVERSITY OF CALIFORNIA, Oakland, CA (US); SAGE BIONETWORKS, Seattle, WA (US)

(72) Inventors: Kang Zhang, La Jolla, CA (US); Gregory Hannum, La Jolla, CA (US); Trey Ideker, La Jolla, CA (US); Stephen H Friend, Seattle, WA (US); Justin Guinney, Seattle, WA (US)

(73) Assignees: The Regents of the University of California, Oakland, CA (US); Sage Bionetworks, Seattle, WA (US)

(*) Notice: Subject to any disclaimer, the term of this patent is extended or adjusted under 35 U.S.C. 154(b) by 225 days.

(21) Appl. No.: 14/442,089

(22) PCT Filed: Nov. 12, 2013

(86) PCT No.: PCT/US2013/069710
§ 371 (c)(1),
(2) Date: May 11, 2015

(87) PCT Pub. No.: WO2014/075083
PCT Pub. Date: May 15, 2014

(65) Prior Publication Data
US 2015/0259742 A1    Sep. 17, 2015

Related U.S. Application Data

(60) Provisional application No. 61/724,528, filed on Nov. 19, 2012.

(51) Int. Cl.
| | | |
|---|---|---|
| *C12Q 1/68* | (2018.01) | |
| *C12Q 1/6883* | (2018.01) | |
| *C12Q 1/6881* | (2018.01) | |
| *G01N 33/53* | (2006.01) | |
| *G01N 33/574* | (2006.01) | |

(52) U.S. Cl.
CPC ......... *C12Q 1/6883* (2013.01); *C12Q 1/6881* (2013.01); *G01N 33/5308* (2013.01); *G01N 33/57484* (2013.01); *C12Q 2600/118* (2013.01); *C12Q 2600/136* (2013.01); *C12Q 2600/154* (2013.01); *C12Q 2600/16* (2013.01); *G01N 2500/00* (2013.01)

(58) Field of Classification Search
None
See application file for complete search history.

(56) References Cited

U.S. PATENT DOCUMENTS

2004/0132026 A1    7/2004   Olek

FOREIGN PATENT DOCUMENTS

EP    1 035 215 A2    9/2000

OTHER PUBLICATIONS

Handbook of Chemistry and Physics, 49th Edition, 1968, Weast (ed.), The Chemical Rubber Co., Cleveland, Ohio, p. A-245.*
Bai, Lingei, International Preliminary Report on Patentability, PCT/US/2013/069710, The International Bureau of WIPO, dated May 12, 2015.
Bell, Jordana et al., "Epigenome-Wide Scans Identify Differentially Methylated Regions for Age and Age-Related Phenotypes in a Healthy Ageing Population", PLOS Genetics, vol. 8, No. 4, Apr. 19, 2012, pp. e1002629.
Bocklandt et al., "Epigenetic predictor of age", PLoS One, vol. 6, Issue 6, Article No. e14821, pp. 1-6, Jun. 22, 2011.
Florath et al., "Cross-sectional and longitudinal changes in DNA methylation with age: an epigenome-wide analysis revealing over 60 novel age-associated Cpg sites", Human Molecular Genetics, Advance Access, pp. 1-16, Oct. 26, 2013.
Garagnani et al., "Methylation of ELOVL2 gene as a new epigenetic marker of age", Aging Cell, vol. 11, No. 6, pp. 1132-1134.
Hannum et al., "Genome-wide methylation profiles reveal quantitative views of human aging rates", Molecular Cell, vol. 49, No. 2, pp. 359-367, Nov. 21, 2012.
Heyn et al., "Distinct DNA methylomes of newborns and centenarians", PNAS, vol. 109, No. 36, pp. 10522-10527, Jun. 11, 2012.
Kim, Seung Beom, International Search Report and Written Opinion, Korean Intellectual Property Office, PCT/US2013/069710, Feb. 7, 2014.
Leber, Thomas, Extended European Search Report, European Patent Office, Application No. 13852408.7, Sep. 12, 2016.
Arango et al., "Gene-Expression Profiling Predicts Recurrence in Dukes' C Colorectal Cancer", Gastroenterology, vol. 129, No. 3, Sep. 1, 2005, pp. 875-884.
Husseinzadeh et al., "Status of tumor markers in epithelial ovarian cancer has there been any progress? A review", Gynecologic Oncology, vol. 120, No. 1, Jan. 1, 2011, pp. 152-157.
Leber, Thomas, Patent Application No. 13852408.7, European Patent Office, Sep. 6, 2017.

* cited by examiner

*Primary Examiner* — James Martinell
(74) *Attorney, Agent, or Firm* — Joseph R. Baker, Jr.; Gavrilovich, Dodd & Lindsey LLP

(57) ABSTRACT

The invention provides for methods for predicting age of a subject based on the epigenome of the subject.

9 Claims, 53 Drawing Sheets
Specification includes a Sequence Listing.

| ID | Name | AddressA_ID | AlleleA_ProbeSeq | AddressB_ID |
|---|---|---|---|---|
| 19934 cg04400972 | cg04400972 | 74745443 | AAAATAAAAACATCTCAAACTCACATTACAAAAAC SEQ ID NO:1 | 13601340 |
| 28973 cg09809672 | cg09809672 | 12737501 | TTTCATCTAAAAATTTAACTCTAACCAAACAACCA CAATTCAAAAAACCA SEQ ID NO:2 | NA |
| 30213 cg10501210 | cg10501210 | 43774458 | CAAAACTACAACACCTTACAACAAAACCAAAATTT ACRAACATCTCTC SEQ ID NO:3 | 66775341 |
| 39647 cg16054275 | cg16054275 | 17771388 | TCCAAATATAAACTTAAACCCAAACAAACCTCAAA AAATCTACACAAACA SEQ ID NO:4 | NA |
| 47340 cg20822990 | cg20822990 | 50699474 | CAAAAAAACTACTACRAAAATCACACAAAAAAAT TCAATAATAACRAAC SEQ ID NO:5 | NA |
| 49956 cg22512670 | cg22512670 | 70754418 | ATAATAACAACTACTAATACCATTCTTAACCTAAAA ACTTATCAACTAAAC SEQ ID NO:6 | NA |
| 54990 cg25410668 | cg25410668 | 26779422 | ACACCRCRTAAAATTACTTATTCTTTTACATAAAAA CACTAAAATCRCCC SEQ ID NO:7 | NA |
| 61752 cg02085953 | cg02085953 | 66719449 | CTAAACTTTCAAACTAAAACCCCTAAAATAAACTCC ATCACATTCTCTTC SEQ ID NO:8 | NA |
| 67888 cg06639320 | cg06639320 | 13732383 | CAAAACTCCTTTCTTCRTACCCTCCRAATCTTAAAA TCACCTAAAAAAAAT SEQ ID NO:9 | NA |
| 86462 cg22016779 | cg22016779 | 10606390 | RCAAAACCCCTAAAAAAAAAACCAATACAACAAATT ACACAATAATTATC SEQ ID NO:10 | NA |
| 86644 cg22158769 | cg22158769 | 17654495 | ACACAAAAACTCTTTAAAAAAACAACTCAACAACT AATTAACCAAACCAC SEQ ID NO:11 | 68643399 |
| 86991 cg22454769 | cg22454769 | 66727363 | CTTAAAAACACAATAATTATCAAAAACATCACCTC TAACCTTACCATACA SEQ ID NO:12 | 23744359 |
| 88430 cg23606718 | cg23606718 | 20628466 | TCTCAAAACCTTAACAACTTACCACTAAAAACCCAC CAACATAAACTCTCA SEQ ID NO:13 | 58618322 |
| 88984 cg24079702 | cg24079702 | 42601467 | AAAACACAATAATTATTCAAAAAACATCACCTCCAAC AATACAACAAAACA SEQ ID NO:14 | 50810372 |
| 93051 ch.2.30415474F | ch.2.30415474F | 51667506 | AAAACTAACTCTTCCTCTACCACCATATAATCATCAA ATAAACTCTCAAACA SEQ ID NO:15 | NA |

FIGURE 9A

| ID | Name | AddressA_ID | AlleleA_ProbeSeq | AddressB_ID |
|---|---|---|---|---|
| 93891 cg00481951 | cg00481951 | 14709443 | CRTTTCAACACCTAAATCAACRCTTCCAAAATCAA CACCAAAAATAAAC SEQ ID NO:16 | NA |
| 97218 cg03607117 | cg03607117 | 70676435 | TATCTACAACCCRAAATAAAACRCAAACTAAATCR AAACTAAACCAAAAC SEQ ID NO:17 | NA |
| 98073 cg04474832 | cg04474832 | 31636354 | TAACRTTTACTTACTTATTACTACTCTACAAAAATTA ACAACATCTAACCC SEQ ID NO:18 | NA |
| 100937 cg07553761 | cg07553761 | 43625429 | ATATAACACCAAATAAAAAAATAATTCCTCAAAAAC CATCAACCACCAACA SEQ ID NO:19 | 17688430 |
| 116505 cg25478614 | cg25478614 | 60721480 | AAAACCCAAAAAAAACCAAAACTCTTAAAAAAA CTAAACATCCCTTAC SEQ ID NO:20 | NA |
| 120672 cg02650266 | cg02650266 | 66683464 | ACTATCCTCAAAAACCACCAAAATACTAAAAAAAA CAACAACAACAAACA SEQ ID NO:21 | 73675449 |
| 137234 cg25428494 | cg25428494 | 68769372 | AAATATATTACATTATAATAACATCTAAACTCTTAA TATAACTATCACCC SEQ ID NO:22 | NA |
| 146444 cg08234504 | cg08234504 | 24749379 | TAAAACCTAATTCACCTATTCACACACAAAAACAT AACTACCATAACAAC SEQ ID NO:23 | NA |
| 159652 cg23500537 | cg23500537 | 48779348 | TACAACCACACATCCAAAACTAACAAAACRAACAC TCTACAAATCCTAC SEQ ID NO:24 | NA |
| 164052 cg00486113 | cg00486113 | 37770376 | AAACCTAAACCCACCCCRAAAAAAATACAAATAAT AAAATCCCCTCAACC SEQ ID NO:25 | NA |
| 172686 cg06493994 | cg06493994 | 49740386 | CAAAAAATACRATAAAAAAATCCTTCCAAAATTA TCTAAATCCTTCCRC SEQ ID NO:26 | NA |
| 172936 cg06685111 | cg06685111 | 59773369 | TTACCAATCTAAATCCRTCCTAATACCTTACTATAC ATACAATTCTACTC SEQ ID NO:27 | NA |
| 181162 cg13001142 | cg13001142 | 74697332 | CACCRTCTCAAAAATTAACAAATTCAAATCTAACCT AATCAAATTTTATC SEQ ID NO:28 | NA |
| 186168 cg16867657 | cg16867657 | 57761335 | TCTAAACAACAAATAAATAATATTCCTAAAACTCCATA AACATTAAACCACCA SEQ ID NO:29 | 17685408 |
| 190156 cg20052760 | cg20052760 | 32659462 | ATTTTCACRCCATCATAACATTTTATTCCTCACCTAA CTAAAAACAACTC SEQ ID NO:30 | NA |

FIGURE 9B

| ID | Name | AddressA_ID | AlleleA_ProbeSeq | | AddressB_ID |
|---|---|---|---|---|---|
| 193374 cg22736354 | cg22736354 | 26771442 | ACTCRAATACAAAATATACTTTAAAAATTTAACCACCRACAACAACRAC | SEQ ID NO:31 | NA |
| 204211 cg03473532 | cg03473532 | 31780418 | AATTCAAAATTTTCAAATAATAATAAACAACTACTATCTCAAACACATAC | SEQ ID NO:32 | NA |
| 209326 cg07927379 | cg07927379 | 42797400 | ACTAAAACACAAAAAACATACAAACACCCAAACCTCATATAATAAAAACCA | SEQ ID NO:33 | 27785403 |
| 209350 cg07955995 | cg07955995 | 49679509 | ATCTCCACATTCTTTCTTCTACCAACAAACCAAATAATAATAACAAAACA | SEQ ID NO:34 | 57684340 |
| 209501 cg08097417 | cg08097417 | 24706423 | ATATTTAACAACCTCAAAAATTATCTTATCTCRCRTTCTTTCTTCTACC | SEQ ID NO:35 | NA |
| 209919 cg08540945 | cg08540945 | 24889307 | AATTCAAAACTTTAAACCCCAACACTCTACAAACAAAAAACAAAACACA | SEQ ID NO:36 | 59640388 |
| 215998 cg14361627 | cg14361627 | 42786323 | RACCCCCRACTAAATCATATTTAACAACCTCAAAAATTATCTTATCTCC | SEQ ID NO:37 | NA |
| 222324 cg20426994 | cg20426994 | 55807502 | ATAACACTTAACACACAAATAACAAACCTCCTCCAAAACACCTAATCCA | SEQ ID NO:38 | 12608480 |
| 224209 cg22285878 | cg22285878 | 49781392 | TCTTCTACCAACAAACCAAATAATAACAAAACAAAACTCCCCAATCA | SEQ ID NO:39 | 49684508 |
| 236164 cg07583137 | cg07583137 | 23646337 | ACAACCCCATTTAAAATTTTAATACACTAAAAATCATTCAAAAAACTTC | SEQ ID NO:40 | NA |
| 242497 cg16419235 | cg16419235 | 72778377 | CAAAAAACTAATTTCTACAATCACTAAAACCTACAACAACACTACTCCCA | SEQ ID NO:41 | 26722332 |
| 279142 cg19935065 | cg19935065 | 27739481 | TATTATTTAAAACTTTACTATCTCCAAAACACRTAAACACCTCACAACC | SEQ ID NO:42 | NA |
| 280381 cg22796704 | cg22796704 | 60625432 | CRAAAAAAACCRCATTCAAAACACTTACTCCTAAATACCTAATATAATC | SEQ ID NO:43 | NA |
| 286836 cg02046143 | cg02046143 | 38797338 | TTTCCACATAACTCCTCCTACTACTTTATTACCTAAACCAAAAAAAAACA | SEQ ID NO:44 | 15671301 |
| 290175 cg04940570 | cg04940570 | 46668492 | ACACACCCTCAAAACACCTTAAACAAATACACTAAAAACCAAAAATTCA | SEQ ID NO:45 | 30738394 |

FIGURE 9C

| ID | Name | AddressA_ID | AlleleA_ProbeSeq | | AddressB_ID |
|---|---|---|---|---|---|
| 291937 cg06419846 | cg06419846 | 40649319 | TAATCACATATCCTACCACTACACTAAAAACTTCA ACTAACAACAAACA | SEQ ID NO:46 | 16728494 |
| 296834 cg11067179 | cg11067179 | 41621317 | CRAAAAATAATCCRACCRCTATATAAACACAAAT AAATACCAAATTACC | SEQ ID NO:47 | NA |
| 308206 cg22213242 | cg22213242 | 25756359 | ATCTACTAACACACACAACAATCTAACACTCATCT ATATCCACACAACA | SEQ ID NO:48 | 21781482 |
| 308942 cg23091758 | cg23091758 | 55782376 | AAAAACAACAACACTAATAAAAACTAACCAACAA TCCAAAAATCCACCA | SEQ ID NO:49 | 30707421 |
| 309640 cg23744638 | cg23744638 | 35611335 | CACAAAACTTTAAAAAACACTCTAACCCTACTACT CACCCATACAAACA | SEQ ID NO:50 | 14763344 |
| 314613 cg00748589 | cg00748589 | 60757479 | AACTCTACCTCAAAAAACTCAAAACCATCRTACTA AACCACAAAAACTC | SEQ ID NO:51 | NA |
| 315365 cg01528542 | cg01528542 | 50719302 | TCCCACTTTACAATCTTTACCAAATTAATCATCAC TAACAAAATTAAC | SEQ ID NO:52 | NA |
| 330233 cg18473521 | cg18473521 | 28617472 | ATTACCCATTCTCRCTCRTAAATCCAATTCAATTAT ACTAACCCAAATC | SEQ ID NO:53 | NA |
| 331413 cg19722847 | cg19722847 | 25621361 | CAACAAATCTATCTTAAAACAAACCAATTACRAT ACCCATACAATTCTC | SEQ ID NO:54 | NA |
| 350626 ch.13.39564907R | ch.13.39564907R | 61804317 | GCTACTTCCCTAAATTAAACAACAATTATTACCTC TCACCTAAACTACT | SEQ ID NO:55 | NA |
| 352716 cg03032497 | cg03032497 | 24810422 | TATCTAACTCAACCCCTTTAAATATTCTTCCAAATA AAATTATTAAATTC | SEQ ID NO:56 | NA |
| 367851 cg03399905 | cg03399905 | 52669494 | CCCATACTCRACCTTCTAAAAAATACCACAAACAC TAACAATAATAAAC | SEQ ID NO:57 | NA |
| 368628 cg04875128 | cg04875128 | 66707375 | AACTATAACTCTACAACAACAACAATTCTAC TACAAATACATAACA | SEQ ID NO:58 | 34724474 |
| 371123 cg09651136 | cg09651136 | 69636474 | CACTACACCCAAACAATTAAAACTTAAAATACA ATATAATCCAACATC | SEQ ID NO:59 | NA |

FIGURE 9D

| ID | Name | AddressA_ID | AlleleA_ProbeSeq | AddressB_ID |
|---|---|---|---|---|
| 377332 cg21296230 | cg21296230 | 29625433 | CRCRAAAATAAATTATAAAAAACCATCRCRAAATC CTTCCTACTAAAACC SEQ ID NO:60 | NA |
| 388382 cg04416734 | cg04416734 | 71765505 | TCAAAATCAAACTCCAATAAAACCAAACCCCT ACCCTCTAAAAACA SEQ ID NO:61 | 24794497 |
| 392814 cg07082267 | cg07082267 | 49808346 | AAAAAAACCATAAAAAATCTCCRTTTCACAAATA AACACACCAAAACCC SEQ ID NO:62 | NA |
| 406094 cg02867102 | cg02867102 | 24773488 | AATAACTAAAAAATCTATCTAAATCAAAACRCTA ACTTTAACCTTCCTC SEQ ID NO:63 | NA |
| 410441 cg06874016 | cg06874016 | 71689361 | AAAAACACAAAAGRAACACAATTATAAATAATAAA CTTACTCTACAAACC SEQ ID NO:64 | NA |
| 418324 cg14692377 | cg14692377 | 11791474 | AACTACACAAAAAAACTAATCCCAAACTAAACAAA CAAACTAACCTCACA SEQ ID NO:65 | 74735323 |
| 424420 cg21139312 | cg21139312 | 71738392 | AAAACCACCCCAAACTCTATAATTTCCAAAACAAA TACAAAAACAACACA SEQ ID NO:66 | 36705403 |
| 434803 cg19283806 | cg19283806 | 62709369 | AATTTCTCCTTAAACAATCCCACAAAAATAACAAC CAAAAAAAATACA SEQ ID NO:67 | 12681323 |
| 449879 cg14556683 | cg14556683 | 39707455 | AAAAACACCAAACTCCACATAAAAACACACAACAA CTTCAACAACAAACA SEQ ID NO:68 | 23657395 |
| 465513 cg07547549 | cg07547549 | 72801360 | AACTCAACTCCATTAAAATACTCCRAACRTATCCA AAATACTAAAATAC SEQ ID NO:69 | NA |
| 479076 cg05442902 | cg05442902 | 45650355 | CTCTCACTCTATACCTCTTAATTATCTTACATACTCT AATCTTTACATAC SEQ ID NO:70 | NA |
| 480022 cg08415592 | cg08415592 | 18687383 | AACAAATCTTTCTCCTTAAAACCACAACAAACCCC AACCCTAAAAATAC SEQ ID NO:71 | NA |

FIGURE 9E

| AlleleB_ProbeSeq | Infinium_Design_Type | Next_Base | Color_Channel |
|---|---|---|---|
| AAAATAAAAACATCTCAAACTCGCGTTACGAAA ACCGATTCGAAAAACCG    SEQ ID NO:72 | I | | |
| | II | T | Red |
| CGAAACTACGACACCTTACGACGAAACCAAAAT TTAAATCTACGCAAACG    SEQ ID NO:73 | I | | |
| | II | A | Red |
| | II | | |
| | II | | |
| | II | | |
| | II | | |
| | II | | |
| ACGCGAAAACTCTTAAAAAAAACGACTCAACGA CTTAACCTTACCGTACG    SEQ ID NO:74 | I | | |
| CTTAAAAACACAATAATTATCGAAAACGTCGCCT CCGACGTAAACTCTCG    SEQ ID NO:75 | I | C | Grn |
| TCTCGAAACCTTAACGACTTACCGCTAAAACCC GCAATACAACAAAACG    SEQ ID NO:76 | I | A | Red |
| AAAACACAATAATTATCGAAAACGTCGCCTCCG ACGTAAACTCTCGAACG    SEQ ID NO:77 | I | C | Grn |
| | II | C | Grn |

FIGURE 9A-1

| AlleleB_ProbeSeq | Infinium_Design_Type | Next_Base | Color_Channel |
|---|---|---|---|
| | II | | |
| | II | | |
| | II | | |
| GTATAACGCCAAATAAAAATAATTCCTCAAAA ACCGTCGACCACCGACG  SEQ ID NO:78 | I | C | Grn |
| GCTATCCTCAAAAAACCGCCAAAATACTAAAAA AACGACAACAACGAACG  SEQ ID NO:79 | I | C | Grn |
| | II | | |
| | II | | |
| | II | | |
| | II | | |
| | II | | |
| | II | | |
| TCTAAACAACGAATAAATATTCCTAAAACTCCGT AAACGTTAAACCGCCG  SEQ ID NO:80 | I | C | Grn |
| | II | | |

FIGURE 9B-1

| AlleleB_ProbeSeq | Infinium_Design_Type | Next_Base | Color_Channel |
|---|---|---|---|
| | II | | |
| | II | | |
| ACTAAAACACGAAAACGTACAAACGCCCAAACC TCGTATAATAAAAAACCG    SEQ ID NO:81 | I | A | Red |
| ATCTCCGGTTCTTTCTTCTACCGACGAACCAAA TAATAATAACAAAACG    SEQ ID NO:82 | I | A | Red |
| | II | | |
| AATTCAAAACTTTAAACCCCCAAGCGCTCTACAAA CAAAAAACGAAACGCG    SEQ ID NO:83 | I | A | Red |
| | II | | |
| ATAACGCTTAACAACAACAAATATAACAAACCTCCTC CGAAACGCCTAATCCG    SEQ ID NO:84 | I | C | Grn |
| TCTTCTACCGACGAACCAAATAATAATAACAAAA CGAAACTCCCAATCG    SEQ ID NO:85 | I | A | Red |
| | II | | |
| CAAAAAAACTAATTTCTACAATCGCTAAAACCTAC AACGACGCTACTCCCG    SEQ ID NO:86 | I | C | Grn |
| | II | | |
| | II | | |
| TTTCCACGTAACTCCTCGCTACTTTATTACCTA AACCAAAAAAAAACG    SEQ ID NO:87 | I | A | Red |
| ACACACCCTCGAACGCCTTAAACGAAATACGCT AAAAAAACCAAAATTCG    SEQ ID NO:88 | I | A | Red |

FIGURE 9C-1

| AlleleB_ProbeSeq | Infinium_Design_Type | Next_Base | Color_Channel |
|---|---|---|---|
| TAATCACGTATCCTACCGCTACACTAAAAACTTC CGACTAACAACAAACG    SEQ ID NO:89 | II | A | Red |
| ATCTACTAACACACACCGACAATCTAACACTCAT CTATATCCACACAACG    SEQ ID NO:90 | I | A | Red |
| AAAAACGACGACGCTAATAAAAACTAACCCGAC AATCCGAAAATCCACCG    SEQ ID NO:91 | I | C | Grn |
| CACGAAACTTTAAAAAACACTCTAACCCTACTA CTCACCCATACAAACG    SEQ ID NO:92 | I | A | Red |
|  | II |  |  |
|  | II |  |  |
|  | II |  |  |
|  | II |  |  |
|  | II |  |  |
| AACTATAACTCTACGACGACAACGAACGATTCT ACTACGAATACGTAACG    SEQ ID NO:93 | II | C | Grn |

FIGURE 9D-1

| AlleleB_ProbeSeq | Infinium_Design_Type | Next_Base | Color_Channel |
|---|---|---|---|
| | II | | |
| TCGAAATCAAACTCCGATAAAAACCCAAAACCC CTACCCTCTAAAAACG SEQ ID NO:94 | I | A | Red |
| | II | | |
| | II | | |
| | II | | |
| AACTACGCGAAAAACTAATCCGAACTAAACA AACGAACTAACCTCGCG SEQ ID NO:95 | I | C | Grn |
| AAAACCGCCCGAACTCTATAATTTCCAAAACAA ATACGAAAAGACACG SEQ ID NO:96 | I | T | Red |
| AATTTCTCCTTAAACAATCCCGCAAAAATAACA ACCAAAAAAAATACG SEQ ID NO:97 | I | A | Red |
| GAAAACACCAAACTCCACATAAAAACGCGCAAC AACTTCAACGACAAACG SEQ ID NO:98 | I | C | Grn |
| | II | | |
| | II | | |
| | II | | |

FIGURE 9E-1

| Forward_Sequence | Genome_Build | CHR | MAPINFO |
|---|---|---|---|
| GGGTATTTTCGGGGGTGAGGGCATCTCAGGCTCGCGTTACGGGGACCGGTTCGGGAGAC[CG]TGG AGCCGAGGTGTCGAATGGAGGGCTTACTTCGGCCGGCCGGGCCAGGGAGGGCCACCCTCCT SEQ ID NO:99 | 37 | 1 | 117665053 |
| CCCCAGAGAGCTTTCATCTAGAAGGTTTGACTCTGCCAGACAACCAGCGAGCATCTTCT[CG]CAATC TGTTGCTTCTTCCATGGCAAACTCCAGAGAATTAAGAAGCCAAACTCAACATGC SEQ ID NO:100 | 37 | 1 | 236557682 |
| ACGTGGGGGAAGAAGGGGGTTACGCCATCAAGTCTGAAGCCTGAGACCACCATCGC[CG]CCT GCGCAGACCCAAATCTTGGTCCCGCCGTAAGGTGCCGCAGTCCGAATGTTCCAGAA SEQ ID NO:101 | 37 | 1 | 207997020 |
| TTCATGAGCCGACAAAGCTGTATCCCTCCATTTCCACCTGCCAACACCACGGAAGCAGT[CG]TCCGT TACCACTGACCTGAGGCCTGCCTGGGTCCAAGCTCACACTTGGAGAACCTTCTGT SEQ ID NO:102 | 37 | 1 | 169556022 |
| AATGCCTGCTTCACAGAGAACTGTGCGAGGATCACACAAGAAAATGCTTGTCAACTGGG[CG]TGGT GGGCCATGCCTGTAATCCCAGCTACTCGGAGACTAAGCCAGGAGAATGCTTGAAC SEQ ID NO:103 | 37 | 1 | 17338766 |
| GGGTCCTGATGGTGGTAACAACTGCTGATGCCCATCTTGGCCTGGGGCACTGAGATGCC[CG]GAGA TCACAGTGTTAGCTTCAGGGCGGGGTAGAAATTAGAGGATAGGGGATCTCTAGGGC SEQ ID NO:104 | 37 | 1 | 26855765 |
| CTAGCCTCACAGCACGCGTGGAGTTGCTTGTCTTTACATAGGAGGTCACATTCTCTT[CG]TGTAAT GCCACCAATGTGCCGATTCTCCCAGTGGGCTGTGAGAAACCTACGCCCTCT SEQ ID NO:105 | 37 | 1 | 28241577 |
| AGTTTGCCTCCAGGGAAACTGAGGCACAAGGCAGCAATGATTACTGAGGGTCCTGCCTC[CG]CTCC TCTAGGTGAGGAGCCTATTCCAGGGCTCAGTCTGAAAGCCTAGAGGCGAGGGGC SEQ ID NO:106 | 37 | 2 | 97202260 |
| CCTTGTTTGCCAGGGCCTCTTCTTCGTGCCCTCGGCGCGGAGTTTCGGACGAGGAGGTTAT[CG]GGAGC GTGCCTCCGGGTGGGCTCCAGGCCCCTTAAAAGGGAGCCAGTGCAACAGATTGGTTAACCAGGCCT SEQ ID NO:107 | 37 | 2 | 106015739 |
| CTACAGTGCCCAGGCCCCCTTAAAAATCCCAAAGACTGGACAGCAAATGCCCTTAGGTTGCATG[CG]TGTT CCCAGTCTTCTAAAAATCCCAAAGACTGGACAGCAAATGCCCTTAGGTTGCATG SEQ ID NO:108 | 37 | 2 | 230452311 |
| AGAGCGCTACGTCGCCGGCAGCAGCCGCTCTCAAAGAGTTCCCGCGTGCGCCGCCAGCC SEQ ID NO:109 | 37 | 2 | 39187539 |
| CGGCAAGGCCAAGCCGCTGAGCCGTCTGAGCAGCACAGTAGTTATCGGAGGCGTGCCCTCCGGCGTGGGCTCT[CG]GGCG CGAGTTTCGGACGAGGCCTGGGCGCGGTGCGCGGTCAGGGGTCTGCCACGCGGGATCTC SEQ ID NO:110 | 37 | 2 | 106015767 |
| CTGACCGTGGTGCTGAGCGGCCCCAGCCGGTAAGTCGCTCGAGCGGTGCCGAGCCTGTGCGGCCG[CG]CCCT GCTGACTGCGGGCCCCAGCCGGTAAGTCGCCAAGGCCGTCCGGCAGAGGCTGCGTTGGT SEQ ID NO:111 | 37 | 2 | 131513927 |
| CTCCGGGTCTTGGGAGGCACAGTAGTTATCGGCCGGTCTCGCCCACGCCGGGGTGCTGCGGCTCTCTGCC[CG]CGA GTTTCGGACGAGGCCTGGGCGCGGTGCGCGGTCAGGGGTCTGCCACGCCGGGATCTCTGCC SEQ ID NO:112 | 37 | 2 | 106015771 |
| ACCCGCTATCTGGTGATGATCACATGTGCAGAGATAGAGAAAGGCAGAATGCTTGAAGATCCAATTTGGAGATTA[CA]TCCA TAGGACTTGCTGATGATCACATGTGCAGAGGAAGAGCCAGTCCTCAAATATGGCC SEQ ID NO:113 | 36 | 2 | 30561970 |

FIGURE 9A-2

| Forward_Sequence | Genome Build | CHR | MAPINFO |
|---|---|---|---|
| TCAGAGGTCTGCGTTTCAGCACCTGGGTCAGCGCTTCCCAGGGTCAGCACCAGGAGATAGA[CG]CCAT TGTCGCTTCGTGCCCAGACAACTACCCAGATTTTGTAATTTCTTGAATGCCAAGT SEQ ID NO:114 | 37 | 3 | 187387650 |
| CGCTGTGGCCCCGAGCGGAACGGCCCGAAGAGGAGAGCGTCCCCGGAACCCAGTGCC[CG]CCC TGGCCCAGCCCCGATCCAGCCTGCGCCTCACCTCGGGTTGTAGACAGAGCGGCGGGG SEQ ID NO:115 | 37 | 3 | 53080440 |
| CCAGCCAAGTGGCCTTGATCGTTTCCCAATGCCCCGAGCCTGTTTCTGCCAGTAGAG[CG]GGTCA GATGTTGCCAACCTCTGCAGAGTAGCAATAAGCAGTAAACGCCACGCTCTGCACA SEQ ID NO:116 | 37 | 3 | 52008487 |
| AATCCGCATGGCACCGGTGGTCTGAGGAATTATCTTTACTTGGCGCCACACGGGGCGGGAAG[CG]CC GGTGGCCGACGGCTTCTGAGGAATTATCTTTACTTGGCGCCACACGGGGCGGGGCCT SEQ ID NO:117 | 37 | 3 | 160167977 |
| TCGGGAGCTGAGGGACCCAGAAAAGCACCAAACTCTTAGAAGGACTGAGCATCCCTTA[CG]TCCA AACCAATGGGGCAGGAGCAAGGTTAGGGAGGGCTGGAGAATCCGGAGACGTCGA SEQ ID NO:118 | 37 | 3 | 187387866 |
| GCCCGAGAGGATCCAGGGAAAGCAGAAGGGGTTAAGGACCATGGACAGAGCCGTGCGC[CG]CT CGTTGCTGCCGCCTTCCCCAGCACTCTGGGCGGCTCTGAGGACAGCGGTCCATCTTG SEQ ID NO:119 | 37 | 3 | 147558239 |
| GGGAGGGTGGGAGAGGGATGAGGGATGCCACCACAGCCCAGATGCCACCACAGCCCAGATGCAATGCAATATACCCATGGAACAGAA SEQ ID NO:120 | 37 | 4 | 84255411 |
| TTGTATTTCAGCCAAAGCTACTGGAAGTGTCAAGCTGCCAGCTCCCCTGCCCTCCC[CG]TTGCTA TGGCAGCCATGTCTCTGTGTGAATAGGTGAACCAGGCTCCAGGTTAGGACCT SEQ ID NO:121 | 37 | 5 | 139013317 |
| CAGGAGTGCGGTGCAGCCACACACCTTCCTCAGCTTCGTCTGTATTGAAAGAGCTTAGTAAA SEQ ID NO:122 | 37 | 5 | 140419819 |
| ATTCACGGGGAATCAGAGGGTGGAGAGGGCGTGGGTGCCTGAGATGCTGGGAACAGAA[CG]GC TGAGGGGACTCCATTATCTGTACTCTTCCCGGGAGGAGTCTTCCCAAAGTTGTCTAGGTCCTTCCG[CG]CCGG SEQ ID NO:123 | 37 | 6 | 31105711 |
| GGAGAGCAAGTCAAGAAATACGGTGAAGAGGTCCTTCCCAAAGTTGTCTAGGTCCTTCCG[CG]CCGG TGCCTGGTCTTCGTCGTCAACACCATGGACAGCTCCCGGGAACCGACTCTGGGGCG SEQ ID NO:124 | 37 | 6 | 25652602 |
| TCACCACTTCTTTGCCAGTCTAGATCCGTCTGGTGCCTTACTGTGCATACAGTTCTACT[CG]TCTCAG GTGAGGAGGCCACTTAATTTGTAAAAGACTGAGGAAGGGGTAGGATCACCACA SEQ ID NO:125 | 37 | 6 | 30295466 |
| TGTGTTACTAAGTGAAGTCTACTATACATACAGTAAATACTACGCAGTATAAATACCTTTATAAA[CG]ACAAA ATCTGACCAGGCTAGATCTGAATCTGTAATTTCTGAGACGGTGTGTCTGAAGTG SEQ ID NO:126 | 37 | 6 | 147528521 |
| CCGGGGGTCCCTGCCGCCGGCCGGGCGGGCGATTTGCAGGTCAGCGGCCGGTTTCGCG[CG]GCG GCTCAACGTCACGGAGCCCAGAATACCACCCGCTGCCAGATGCGGCAGCGCT SEQ ID NO:127 | 37 | 6 | 11044877 |
| CTTGCGCCTCGAATGCCACGTTGAATACTTCCTCATGTCTTTGGAGACATGTCTCCCCTT[CG]AGCTGC TCCCAGTCAGGTGAGGAATAAAATGCTATGATGGCGTGAAATTCTCCCTTGGT SEQ ID NO:128 | 37 | 6 | 10510789 |

FIGURE 9B-2

| Forward_Sequence | Genome Build | CHR | MAPINFO |
|---|---|---|---|
| TGCGCCAGGGGCGGCCACGCAGGCAGGAGACCAGTGGCCGCAGGACAGGTTGCGCGGG[CG]CC GCTGCTGCCGGTGGCCAAACTTCTCAAAGACACACTTGCACTGAGCAGGCTGATCTC SEQ ID NO:129 | 37 | 6 | 18122719 |
| AATTAAAGACTAATTCAGAATTTCAAGTGATAGTAAACAACTGCTATCTCAAACACATA[CG]ATATA AAATGAAACCACTGTGCCTAACTGCCAGTTCTTTCACTCAAACCTCTGCTGTGA SEQ ID NO:130 | 37 | 7 | 131008743 |
| CGTGGCTGCGCCACAAAGCCGCGGGGGCTGCGACTACAGGAAGCCGGCGCGGGGCTT[CG]GC CCTCACTACAGAGGCCTGGGGCCTGCACGCCCCGTGCTTCAGCCGCGGCGTCCCG SEQ ID NO:131 | 37 | 7 | 156433108 |
| AGAAATTATCTTGTCTCCGTCTTCTTTCTTCTGCCGGGAGCCAGGTAATGGTAACAGAG[CG]AAACT CCCCAGTCGGAACTTCTGGGTTGCAGCAGCCTGCGCCCCCCTCCCGCAGCCGC SEQ ID NO:132 | 37 | 7 | 130419159 |
| CCGGCTAAGTCATGTTAACAGCCTCAGAAATTATCTTGTCTCCGCGTTCTTCTTCTGC[CG]GCGAGC CAGGTAATGGTAACAGAGCGAAACTCCCCAGTCGGAACTTCTGGGTTGCAGCAG SEQ ID NO:133 | 37 | 7 | 130419133 |
| CCCCGAGGCGGACGCAGAAGGGCGCGGGGGCCCCCACTCCTGCCCGCGTCGGGGCCGCAG[CG]CGC TCCGCCCTTTGCCTGCAGAGCCGCTGGGGGTTTAAAGTCTGAACCCATGCACGGCTG SEQ ID NO:134 | 37 | 7 | 152591698 |
| TCGGAACGCGCGGCCCCCCGGCTAAGTCATGTTAACAGCCTCAGAAATTATCTTGTCTC[CG]CGTTC TTTCTTCTGCCGGCGGAGCCAGGTAATGGTAACAGAGCGAAACTCCCCAGTCGGAA SEQ ID NO:135 | 37 | 7 | 130419116 |
| GAAGGGCATTGGTGGCGCTTGGCAGCAGGCCCCTCCAGAGCAGGTGTGACAGACCTCTC[CG]GGGCGCTGATC[CG]CGG CGGGGGCGGGGGCTGCCCCTAGGGCCTCCAGAGAACCCACCAGAGGCTGCTGGTG SEQ ID NO:136 | 37 | 7 | 130418324 |
| CTCCGCGGTCTTCTTTCTTCTGCCGGCGAGCCTGCCCCCCCATTAAGGTTTTTGATACACTGAGGA[CG]GAACT TCTGGGTTGCAGCAGCCTCGCCGCCCCCCATTAAGGTTTTTGATACACTGAGGA SEQ ID NO:137 | 37 | 7 | 130419173 |
| CAAACACCAGGCAGCCCCATTAAGGTTTTTGATACACTGAGGATCATTCAGAAAACTT[CG]GATTC CTAGTTATAGAGTTGAATCAACAACACACTCCAGAAGTCCTGACATTAGG SEQ ID NO:138 | 37 | 8 | 82644012 |
| CTGCGCCCTCTGCAAAGGGCTGATTTCTACAGTCGCTAGGACCTGCAGCGGCGTGCTCC[CG]CGGG GCTGCCGCATGTCCATTATAGTCGCTAGAGGGCAGCGCTCTCTGCG SEQ ID NO:139 | 37 | 8 | 57360613 |
| GCAACACAGAGTGCTTTACCATGCCTTAAGGACAGCTGTCACATGACTCTTCCCTAATA[CG]GTTGT GAGGTGCTCACGTGTTTTGGAGATAGCAAAAGTCTCAAATAATATGGCACAGACG SEQ ID NO:140 | 37 | 10 | 98062687 |
| TCCTAAGCCTCTCTGAGCTGGGTCTTGGCCACCTTCCGGGGTGTGAGCGTCACGGGAGAT[CG]ACCA CACCAGGCACCCAGGAGCAAGTGCTTTGAAATGCGGCTTTCTCCGGACCTTGCAGG SEQ ID NO:141 | 37 | 10 | 49673534 |
| GAGTCAGTGCACAGAGTTAGAGGCAGGCAGGCAGAAGAACGCAGAAAGAAGGAGACCTCCCAACCTCGGCCC[CG]CCC TTCCCTGGCCGCAACAAAGCAGCGAGGGGCCACGTGTGGAAAAGCAGTGCAGAT SEQ ID NO:142 | 37 | 11 | 133797911 |
| GCGCACACACGCACACACCCTCGGGCGCCTTGGACGGGTGCGTGGACGGGAGCCAGAAGTT[CG]GAG CGAGCGCGGGGCGGCCAGAGCGCCGCCGCCGCTGCGAGCCCTGAGCCGCTGACCCCCCT SEQ ID NO:143 | 37 | 11 | 12696758 |

FIGURE 9C-2

| Forward_Sequence | Genome Build | CHR | MAPINFO |
|---|---|---|---|
| CACCGGGCTCACACTGCTGCTCGACAGGAGCCTGGGCACAGGGGTCCTCGCAACTGCGCC[CG]TCTG CTGCCAGCCGGAAGCCCTCAGTGCAGCGGCAGGACACGTGACCATCCACCTCCTCC SEQ ID NO:144 | 37 | 11 | 66083697 |
| CCTCGCTACAACTGTGTCCACACAGCTAGTTGACACATCTGTGGCACACACAC[CG]GCAAT CTGGCACTCATCTGTCCACACAGCGGTGCGGATCATCTCCGCTGGCCGGAAA SEQ ID NO:145 | 37 | 11 | 66083541 |
| TAGTTGACACACATCTGTGGCACACATCTGGCACTCATCTGTCCACACAG[CG]GTGCG GATCATCTCCGCTGGCCGGAAACCCAGGCGACAGTGGCAGTGTAGCCTTGTG SEQ ID NO:146 | 37 | 11 | 66083573 |
| CAAAGCCGGCGAGGAGGCGGCGGCGCTGGTGGGGGACTGACCCGGCAGTCCGAGAATCCAC[CG]CG GCCTTTTCACCCAACCGCCCCTCTGCGTGGGGAGCACTCTAGCCCTCTGTACTCACCATGCAAG[CG]GGGT | 37 | 11 | 9025767 |
| TCGACTTAAACCCACGAAGCTTTGGGGAGCACTCTAGCCCTCTGTACTCACCATGCAAG[CG]GGGT GCGCGTCGCGCACACACTCACTCACTGAAGATAGGGGCTTTCTAGGAAAAATACT SEQ ID NO:148 | 37 | 11 | 10323902 |
| CCGGTGCGCGGGCTCACCTCAAGGAGCTCAGGGCCATCGTGTCGAACCAACAGAGGCT[CG]TCCG CACCCAGCGCCAGAGCATCGACGAGCTGGAGCCTGAACGAGCTGAGCGCT SEQ ID NO:149 | 37 | 12 | 11653486 |
| TGTTACAATTTAACTACTTTCTCTTTCTCTCTCTCTCTCTCTGGTAAAAA[CG]TAACCTCT GCTAGTGATGACCAAACTGGTAAAGATTGTAAAGTGGGAAAATTGGATT SEQ ID NO:150 | 37 | 12 | 81468232 |
| CTCCTCGGCCCCCTCTGGCCCCCGTCTCCTTCTCTTCTCTCCCCCCTCTCTCCAGGAG[CG]ACTCTGG GTTAGCACAATTGAACTGGATTTACGAGCGAGAATGGGTAATTACATCCCCA SEQ ID NO:151 | 37 | 12 | 54448265 |
| TCTGCTTACAGCTGTTCCAAATTAAGCATATCTGGATGGTGTGACACTTTTGTTAGTC[CG]AGAACT GTATGGGCATCGCAACTGGGCCTGTTCCAAGATAGACTTGTTGGGACCTTCAAA SEQ ID NO:152 | 37 | 12 | 30849114 |
| GTGAATGGATTTGGGAGGGAGGGAGGATCAGATAGAGGCCAGAAGTCCGGTGAGCAATATTA[CA]GTA GTCCAGGTGAGAGGTAATAATGGCCTGCCTAACCCAAGGAAGCAGCCACCGGGGATTA SEQ ID NO:153 | 36 | 13 | 40666907 |
| CACACCACTCGTATCTAACTCAACCCTTTAGATATTCTTCCAGGTGAAATTATTGGATT[CG]GTCAGA ATGGGGAGGGGCCACTATGCCCTTAAGAGAGGCTCAGAAGTGCCTACCTGGCTAA SEQ ID NO:154 | 37 | 14 | 61108227 |
| TTCACCTGACCCCCATGCTCGGCCTTCTGGAAGATGCCCACAGACACTGGCAATAATGGA[CG]CTGGC ACACTCTGCCGGCGCGGGGCCCGGAGCCCGGAGTTCAGCAGCCTCGGACAGAGCCCGA SEQ ID NO:155 | 37 | 15 | 79576060 |
| CGGCGCGCCAGCGCGGGCTGTAGCTCTGCGACGAGCGGGTTCGTGCGCCCGACGCCTGC SEQ ID NO:156 | 37 | 15 | 31775895 |
| CCTGAGCTGAGGACAAACTAAGAACAGTGTGACAACACTGGTGACAAGGATCTGGC[CG]ATG CTGACTATATTGTATTTAAAGTTCTAAATTGTCTGGGTGCAGTGGCTCACGCCTG SEQ ID NO:157 | 37 | 15 | 72525012 |

FIGURE 9D-2

| Forward_Sequence | Genome_Build | CHR | MAPINFO |
|---|---|---|---|
| GGTGCGTTGTTCGCGGGGGTGAATTGTGAAGAACCATCGCGGGGTCTTCTGCTGAGGC[CG]CGG ACACCGTGACCTGCTGCTTCTGGGTCTGTGGGTCTGCAGGGAAACGTAGGAAAAAAGTTGTCAG SEQ ID NO:158 | 37 | 15 | 33010536 |
| ACTGTCTCTGCTTCGAGATCAAGCTCCGATGAGGACCCAGGCCCCTGCCCTCTGGGGAG[CG]GCCA GCCCCAGGGCCCATGTGCCCTCTCCCTGAAGAGCCTTTCCCACGCCACTGGAA SEQ ID NO:159 | 37 | 16 | 30075192 |
| GCTCCTCATGTGAGAAGGACCATAGGAATCTCCCGTTTCACAGGTGGGCACCTGCACACCAAGGCC[CG]ACAA TGGGTCAGGCTGCCAAGGGTGGAGCCGAGATGCAAAGGGCACCTCAGAGCCTGC SEQ ID NO:160 | 37 | 16 | 85429035 |
| CTCCTGGAGTGGGTGCTCTGGGATGCTTCAGGTTTAGACACCGGGGTTACGGCAGCTGC[CG]AGGA AGGCTAAAGCCAGCGCGTCCTGGATTCAGACAGACAGACCTTTAGCCATTAAATCCACTAA SEQ ID NO:161 | 37 | 17 | 62398693 |
| CAGCCTCTCAGGAGCTGACAGGTCCTCTTCGGGGCTCAGGAGGGTGGGCACACACCCAG[CG]GCCT GCAGAGTAAGCTTATTACCCACAACTGTCCCGCTTTGTGCTTCTAAGGTGCACAC SEQ ID NO:162 | 37 | 17 | 40177415 |
| ACCCACCTGCCAGGCTGCGGCGCTGGCTGTGCGGAGGGGCGCGGCTGCCTCG[CG]CCC TCGAGGCACCCGGCTGGCTGTGCGAGGGGCGCGGCGCTGGCGCGCCGTATTGTA SEQ ID NO:163 | 37 | 17 | 28562685 |
| TTGGAGCTGCCAAAGCCGCCCCGGGCTCTGTGGTTTCCAGAGCAGATGCGGAGGCGGCA[CG]TCCT CGTGCCCTTGCTCCAGTGCGCACACGACCTCAGCCTCCTCTCGCCCCGCTGGGCGC SEQ ID NO:164 | 37 | 17 | 55663225 |
| TCCGTAGTATTGTCTCTGGCTTTGCGGGGATTGTTCAAGGAGAAATCCATCCTGACTGG AGCGTGTTGCACTCATCC[CG]CATCC SEQ ID NO:165 | 37 | 18 | 66389420 |
| ACCAGCGCCACCGAGAACACCAGGCTCCACAGCTCCACATGAAGGCGCGACAGCTTCAGCGACAGG[CG]CGA CGGGCCAGCAGCGCGGTCACCACAGCTCCGGCATGTCGCCGCATGTCCGGGACCAC SEQ ID NO:166 | 37 | 19 | 15342982 |
| TTGCAGCCTGGAGCTCAGCTCCATTGGAATGCTCCGGGCTGTCCACGCGCTTCAAGGTGCTGGAATG[CG]CCGC GCCCGGGGCCAGAGCTGCGGGCCGGGGATTATCGCTGCCACGCGCTTCGGGCTGA SEQ ID NO:167 | 37 | 20 | 44658225 |
| GCCAGGTCACCCTCTCACTCTGTGCCTTAGTTATCTTGACTTGCATA[CG]CTGCTCC CTGCACCAGGAACCTCCATCCCCATCTTTGTCTGTGTCGAACTTCAGAAAT SEQ ID NO:168 | 37 | 22 | 21369010 |
| AGTATGTCAGTGGCAGGTCTTTCTCCTGAGACACCAGACCCCAGCCCTGAGGATG[CG]AGGC AGGTGGGTTGGATGAGAGGGGATCTGGATGTCTCAGGCTGTCTGGTCTGTCTCCTCTAAGGG SEQ ID NO:169 | 37 | 22 | 36648973 |

FIGURE 9E-2

| SourceSeq | Chromosome_36 | Coordinate_36 | Strand | Probe_SNPs | Probe_SNPs_10 |
|---|---|---|---|---|---|
| CGGTCTCCCGAACCGGTCCCGGTAACGCGAGCCTGAGATGCCCTCACCCC SEQ ID NO:170 | 1 | 117466576 | R | | rs78180333 |
| TTCATCTAGAAGGTTTGACTCTGGCCAGACAACCAGCGAGCATCTTCTCG SEQ ID NO:171 | 1 | 234624305 | R | | |
| CGGGACTGCGGCACCTTACGGCGGGACCAAGATTTGGGTCTGCGCAGGCG SEQ ID NO:172 | 1 | 206063643 | F | rs61821292 | |
| CGTCCGTACCACTGACCTGAGGCCTGCCTGGGTCCAAGCTCACACTTGG SEQ ID NO:173 | 1 | 167822646 | F | rs9332483 | |
| CGCCCAGTTGACAAGCATTTTCTTGTTGATCCTGCAGCAGTTCTCTGT SEQ ID NO:174 | 1 | 17211353 | R | | |
| CGGGCGATCTCAGTGCCCCAGGCCAAGATGGGCATCAGCAGTTGTTACCA SEQ ID NO:175 | 1 | 26728352 | R | rs59827434 | |
| CACCGCGTGGAGTTGCTTGTTCTTTTACATAGGAGGTCACATTCTCTTCG SEQ ID NO:176 | 1 | 28114164 | R | | |
| TAGGCTTTTCAGACTGGAGCCCCTGGAATAGGCTCCTCACCTAGAGGAGCG SEQ ID NO:177 | 2 | 96565987 | F | | rs13020129 |
| AGGGCTCCTTCTTCGTGCCCTCCGGGTCTTGGGAGCACAGTAGTTATCG SEQ ID NO:178 | 2 | 105382171 | R | | |
| CGTGGCCTGGTTAACCAATCTGTTGCACTGGCTCCCTTTAAGGGGCCTG SEQ ID NO:179 | 2 | 230160555 | R | | |
| ACGCGGGAACTCTTTGAGAGAGCGGCTCAGCGGCTTGGCCTTGCCGTGCG SEQ ID NO:180 | 2 | 39041043 | F | | |
| CTTGGGAGCACAGTAGTTATCGGGAGCGTCGCCTCCGGCGTGGGCTCTCG SEQ ID NO:181 | 2 | 105382199 | R | | |
| TCTCGGGGCTTGGCGACTTACCGCTGGGGGCCCGCAGTGCAGCAGGGCG SEQ ID NO:182 | 2 | 131230397 | F | | |
| CGCCCGAGAGCCCACGCCGAGGCGACGCTCCCGATAACTACTGTGCTCC SEQ ID NO:183 | 2 | 105382203 | R | | |
| CATCCATAGGACTTGCTGATGATCACATGTGGCAGAGGAAGAGCCAGTCC SEQ ID NO:184 | 2 | 30415474 | F | | |

FIGURE 9A-3

| SourceSeq | Chromosome_36 | Coordinate_36 | Strand | Probe_SNPs | Probe_SNPs_10 |
|---|---|---|---|---|---|
| GTTTCAGCACCTGGGTCAGCGCTTCCCAGGGTCAGCA CCAGGGATAGACG SEQ ID NO:185 | 3 | 188870344 | R | | |
| CGCCCTGGCCCAGCCCGATCCAGCCTGCGCCTCACC TCGGGTTGTAGAC SEQ ID NO:186 | 3 | 53055480 | F | | |
| CGGGTCAGATGTTGCCAACCTCTGCAGAGTAGCAATA AGCAGTAAACGCC SEQ ID NO:187 | 3 | 51983527 | F | | |
| CGCCGGTGGCCGACGGCTTCTGAGGAATTATCTTTA CTTGGGCCCACAC SEQ ID NO:188 | 3 | 161650671 | F | | |
| GGACCCAGAAAAGCACCAAAACTCTTTAGAAGGACT GAGCATCCCTTACG SEQ ID NO:189 | 3 | 188870560 | R | | |
| GCTGTCCTCAGGAGCCGCCAGAGTGCTGGGAAGGC GGCAGCAACGAGCG SEQ ID NO:190 | 4 | 147777689 | F | | rs76832102 |
| CGGGTGACAGTTACACTAAGAGCCCAGATGCCACCAC AATGCAATATACC SEQ ID NO:191 | 4 | 84474435 | F | | |
| GGAGCCTGGTTCACCTATTCACACACAGAGACATGGC TGCCATAGCAACG SEQ ID NO:192 | 5 | 138993501 | F | | |
| GCAGCCACACATCCAAGGCTGACAGGGCGGGCACTC TGCCAAGTCCTGCG SEQ ID NO:193 | 5 | 140400003 | R | | |
| CGGCTGAGGGGACTCCATTATCTGTACTCTTCCCGGG GTGGGTCTAGGTC SEQ ID NO:194 | 6 | 31213690 | F | rs35474509 | |
| AAGAAATACGGTGAAGGAGTCCTTCCCAAAGTTGTCT AGGTCCTTCCGCG SEQ ID NO:195 | 6 | 25760581 | R | | |
| TGCCAGTCTAGATCCGTCCTGGTGCCTTACTGTGCATA CAGTTCTACTCG SEQ ID NO:196 | 6 | 30403445 | R | | |
| CGACAAAATCTGACCAGGCTAGATCTGAATCTGTTAA TTTCTGAGACGGT SEQ ID NO:197 | 6 | 147570214 | F | | |
| CGGGGCTCAACGTCCACGGAGCCCAGGAATACC ACCCGCTGCCAGA SEQ ID NO:198 | 6 | 11152863 | F | | |
| CGAGCTGCTCCCAGTCAGGTGAGGAATAAAATGCTAT GATGGGGTGAAAA SEQ ID NO:199 | 6 | 10618775 | F | | |

FIGURE 9B-3

| SourceSeq | Chromosome_36 | Coordinate_36 | Strand | Probe_SNPs | Probe_SNPs_10 |
|---|---|---|---|---|---|
| CTCGAGTGCAAGGTGTGCTTTGAGAAGTTTGGCCACC GGCAGCAGCGGCG SEQ ID NO:200 | 6 | 18230698 | F | rs28940575 | |
| CGTATGTGTTTGAGATAGCAGTTGTTTACTATCACTTG AAAATTCTGAAT SEQ ID NO:201 | 7 | 130659283 | R | | rs76007347 |
| CGGCCCTCACTACACGAGAGGCCTGGGCGCCTGCACGCC CCCGTGCTTCAGC SEQ ID NO:202 | 7 | 156125869 | F | | rs74424274 |
| CGCTCTGTTACCATTACCTGGCTCGCCGGCAGAAGAA AGAACGCGGAGAC SEQ ID NO:203 | 7 | 130069699 | R | | |
| TGTTTAAACAGCCTCAGAAATTATCTTGTCTCCGCGTTC TTTCTTCTGCCG SEQ ID NO:204 | 7 | 130069673 | R | | |
| CGGCTCCGCCCTTTGCCTGCAGAGGCGCTGGGGGTTT AAAGTCCTGAACC SEQ ID NO:205 | 7 | 152222631 | F | | |
| GCCCCCCGGCTAAGTCATGTTTAACAGCCTCAGAAAT TATCTTGTCTCCG SEQ ID NO:206 | 7 | 130069556 | R | | |
| GTGGCGCTTGGCAGCAGGTGTGACAGACCTCCTCCG GGGGCCCTGATCCG SEQ ID NO:207 | 7 | 130068864 | R | | |
| TCTTCTGCCGGCGAGCCAGGTAATGGTAACAGAGCG AAACTCCCCAGTCG SEQ ID NO:208 | 7 | 130069713 | R | | |
| CAGCCCCATTTAAGGTTTTTGATACACTGAGGATCATT CAGAAAACTTCG SEQ ID NO:209 | 8 | 82806567 | R | | |
| CAAAGGGCTGATTTCTACAGTCGCTAGGACCTGCAGC GGCGCTGCTCCCG SEQ ID NO:210 | 8 | 57523167 | R | | |
| CGGTTGTGAGGTGCTCACGTGTTTGGAGAGATAGCAAA AGTCTCAAATAAT SEQ ID NO:211 | 10 | 98052677 | F | | |
| CGACCACACCAGGCACCCAGGAGCAAGTGCTTTGAA ATGCGGCTTTCTCC SEQ ID NO:212 | 10 | 49343540 | F | rs11101335 | |
| TTTCCACACGTGGCTCCTCGCTGCTTTGTTGCCTGGGC CAGGGAAGGGCG SEQ ID NO:213 | 11 | 133303121 | F | | |
| ACACACCCTCGGGGCCCTTGGACGGGGTGCGCTGGG GAGCCAGAAGTTCG SEQ ID NO:214 | 11 | 12653334 | R | | |

FIGURE 9C-3

| SourceSeq | Chromosome_36 | Coordinate_36 | Strand | Probe_SNPs | Probe_SNPs_10 |
|---|---|---|---|---|---|
| TGGTCACGTGTCCTGCCGCTGCACTGAGGGCTTCCGG CTGGCAGCAGACG SEQ ID NO:215 | 11 | 65840273 | F | | |
| CGGCAATCGGCACTCATCTGTCCACACAGCGGTG CGGATCATCTCC SEQ ID NO:216 | 11 | 65840117 | F | | |
| ATCTGCTGGCACACACCGGCAATCTGGCACTCATCTG TGTCCACACAGCG SEQ ID NO:217 | 11 | 65840149 | R | | |
| GGAGGCGGCGGCGCTGGTGGGGACTGACCCGGCAG TCCGAGAATCCACCG SEQ ID NO:218 | 11 | 8982343 | R | | |
| CACGAAGCTTTGGGGAGCACTCTAGCCCCTGCTACTC ACCCATGCAAGCG SEQ ID NO:219 | 11 | 10280478 | R | | |
| GCTCTACCTCAAGGAGCTCAGGGCCATCGTGCTGAAC CAACAGAGGCTCG SEQ ID NO:220 | 12 | 11544753 | R | | |
| CGTTAACCTCTGCTAGTGATGACCAAACCTGGTAAAG ATTGTAAAGTGGG SEQ ID NO:221 | 12 | 79992363 | F | | |
| TTACCCATTCTCGCTCGTAAATCCAGTTCAATTGTGCT AACCCAGAGTCG SEQ ID NO:222 | 12 | 52734532 | F | | |
| AACAAGTCTATCTTGGAACAGGCCCAGTTGCGATGCC CATACAGTTCTCG SEQ ID NO:223 | 12 | 30740381 | F | | |
| CAGTAGTCCAGGTGAGAGGTAATAATGGCCTGCCTAA CCCAGGGAAGCAG SEQ ID NO:224 | 13 | 39564907 | F | | |
| ATCTAACTCAACCCCTTTAGATATATTCTTCCAGGTGGAA TTATTGGATTCG SEQ ID NO:225 | 14 | 60177980 | R | | |
| CCATGCTCGGCCTTCTGGAAGATGCCACAGACACTG GCAATAATGGACG SEQ ID NO:226 | 15 | 77363115 | R | | |
| CGCCACGTACCCGCAGCAGAACCGCTCGTCGTGTCG CAGAGCTACAGCC SEQ ID NO:227 | 15 | 29563187 | R | | |
| ACTGCACCCAGACAATTTAAAACTTTAAAATACAATAT AGTCCAGCATCG SEQ ID NO:228 | 15 | 70312066 | F | | |

FIGURE 9D-3

| SourceSeq | Chromosome_36 | Coordinate_36 | Strand | Probe_SNPs | Probe_SNPs_10 |
|---|---|---|---|---|---|
| GCGGGGGTGAATTGTGAAGAACCATCGCGGGTCCT TCCTGCTGAGGCCG SEQ ID NO:229 | 15 | 30797828 | R | | |
| TCGAGATCAAGCTCCGATGAGGACCCAGGGCCCTGC CCTCTGGGAGCG SEQ ID NO:230 | 16 | 29982693 | R | | rs36029842 |
| CGGGCCTTGGTGTGCCCACCTGTGAAACGGGAGATTC CTATGGTCCTTCT SEQ ID NO:231 | 16 | 83986536 | R | | |
| ATGGCTAAAAGGTCTGTCTGAATCAGGACGCTGGCT TTAGCCTTCCTG SEQ ID NO:232 | 17 | 59752425 | F | rs71377739 | |
| CGGCCTGCAGAGTAAGCTTATTACCACAACTGTGCC CGCTTTGTGCTTC SEQ ID NO:233 | 17 | 37430941 | F | rs1128719 | |
| GGCTGCGCGGGGAGGCTGGTCCCGGGCTGGGCAGG CGGGCTGGCCTCGCG SEQ ID NO:234 | 17 | 25586811 | R | | |
| CGTGCCGCCTCCGCATCTGCTCTGAAACCACAGAGC CCGGGGCGGCTTT SEQ ID NO:235 | 17 | 53018224 | R | | |
| GATTTCTTCCTTGAACAATCCCGCAAAGATAGCAGCC AAAAAGGATGCG SEQ ID NO:236 | 18 | 64540400 | F | | |
| GAGAACACCAGGCTCCACATGAAGGCGCGAGCAGC TTCAGCGACAGGCG SEQ ID NO:237 | 19 | 152033982 | R | | |
| GCTCAGTCCATTGGAATGCTCCGGGCGCTGTCCAAG GTGCTGGAATGCG SEQ ID NO:238 | 20 | 44091632 | R | | |
| TCTCACTCTGTGCCTCTTAGTTATCTTGCATGCTCTGGT CTTTGCATACG SEQ ID NO:239 | 22 | 19699010 | R | | |
| CGCATCCTCAGGGCTGGGGGTCTGCTGTGTCTCAAG GAGAAAGACCTGC SEQ ID NO:240 | 22 | 34978919 | R | | |

FIGURE 9E-3

| Random_Loci | Methyl27_Loci | UCSC_RefGene_Name | UCSC_RefGene_Accession |
|---|---|---|---|
| NA | NA | TRIM45;TRIM45 | NM_025188;NM_001145635 |
| NA | TRUE | EDARADD;EDARADD;EDARADD | NM_080738;NM_145861;NM_145861 |
| NA | NA | F5 | NM_000130 |
| NA | NA | ATP13A2;ATP13A2;ATP13A2 | NM_022089;NM_001141974;NM_001141973 |
| NA | NA | RPS6KA1 | NM_002953 |
| NA | NA | RPA2 | NM_002946 |
| NA | NA | ARID5A | NM_212481 |
| NA | NA | FHL2;FHL2;FHL2;FHL2 | NM_001039492;NM_001450;NM_201557;NM_201555 |
| NA | NA | DNER | NM_139072 |
| NA | NA | LOC375196;LOC100271715 | NR_028386;NM_001145451 |
| NA | NA | FHL2;FHL2;FHL2;FHL2 | NM_001039492;NM_001450;NM_201557;NM_201555 |
| NA | NA | FAM123C;FAM123C;FAM123C;FAM123C;FAM123C;FAM123C | NM_152698;NM_001105194;NM_001105195;NM_001105194;NM_001105193;NM_001105195 |
| NA | NA | FHL2;FHL2;FHL2;FHL2 | NM_001039492;NM_001450;NM_201557;NM_201555 |
| NA | NA | | |

FIGURE 9A-4

| Random_Loci | Methyl27_Loci | UCSC_RefGene_Name | UCSC_RefGene_Accession |
|---|---|---|---|
| NA | NA | SST | NM_001048 |
| NA | NA | SFMBT1;SFMBT1;SFMBT1 | NM_001005159;NM_016329;NM_001005158 |
| NA | TRUE | ABHD14B;ABHD14B;ABHD14A;ABHD14B;ABHD14B | NM_001146314;NR_027476;NM_032750;NM_015407;NM_032750;NM_001146314 |
| NA | NA | TRIM59 | NM_173084 |
| NA | NA | SST | NM_001048 |
| NA | NA | | |
| NA | NA | HPSE;HPSE;HPSE | NM_001098540;NM_001166498;NM_006665 |
| NA | NA | | |
| NA | NA | | |
| NA | NA | PSORS1C1;PSORS1C2 | NM_014068;NM_014069 |
| NA | TRUE | SCGN;SCGN | NM_006998;NM_006998 |
| NA | NA | HCG18;TRIM39;TRIM39;HCG18;TRIM39 | NR_024053;NM_172016;NM_021253;NR_024052;NM_172016 |
| NA | NA | STXBP5;STXBP5 | NM_001127715;NM_139244 |
| NA | NA | ELOVL2 | NM_017770 |
| NA | NA | | |

FIGURE 9B-4

| Random_Loci | Methyl27_Loci | UCSC_RefGene_Name | UCSC_RefGene_Accession |
|---|---|---|---|
| NA | TRUE | NHLRC1 | NM_198586 |
| NA | NA | MKLN1 | NM_001145354 |
| NA | NA | C7orf13;RNF32 | NR_026865;NM_030936 |
| NA | NA | KLF14 | NM_138693 |
| NA | NA | KLF14 | NM_138693 |
| NA | NA | | |
| NA | NA | KLF14 | NM_138693 |
| NA | NA | KLF14 | NM_138693 |
| NA | NA | KLF14 | NM_138693 |
| NA | NA | CHMP4C | NM_152284 |
| NA | NA | PENK | NM_001135690 |
| NA | NA | DNTT;DNTT | NM_004088;NM_001017520 |
| NA | NA | ARHGAP22 | NM_021226 |
| NA | NA | IGSF9B | NM_014987 |
| NA | NA | TEAD1 | NM_021961 |

FIGURE 9C-4

| Random_Loci | Methyl27_Loci | UCSC_RefGene_Name | UCSC_RefGene_Accession |
|---|---|---|---|
| NA | NA | CD248 | NM_020404 |
| NA | NA | CD248 | NM_020404 |
| NA | NA | CD248 | NM_020404 |
| NA | NA | NRIP3 | NM_020645 |
| NA | NA | | |
| NA | NA | | |
| NA | NA | HOXC4;HOXC4 | NM_153633;NM_014620 |
| NA | TRUE | IPO8 | NM_006390 |
| NA | NA | | |
| NA | NA | ANKRD34C | NM_001146341 |
| NA | NA | OTUD7A | NM_130901 |
| NA | NA | PKM2;PKM2;PKM2 | NM_182470;NM_182471;NM_002654 |

FIGURE 9D-4

| Random_Loci | Methyl27_Loci | UCSC_RefGene_Name | UCSC_RefGene_Accession |
|---|---|---|---|
| NA | TRUE | GREM1 | NM_013372 |
| NA | NA | ALDOA;ALDOA;ALDOA | NM_001127617;NM_184043;NM_000034 |
| NA | NA | | |
| NA | NA | NKIRAS2;NKIRAS2;NKIRAS2;NKIRAS2 | NM_001144927;NM_001144928;NM_017595;NM_001144929;NM_001001349 |
| NA | NA | SLC6A4;SLC6A4 | NM_001045;NM_001045 |
| NA | NA | MSI2;MSI2 | NM_138962;NM_170721 |
| NA | NA | CCDC102B | NM_001093729 |
| NA | NA | EPHX3;EPHX3 | NM_024794;NM_001142886 |
| NA | NA | SLC12A5;SLC12A5 | NM_020708;NM_001134771 |
| NA | TRUE | MGC16703;P2RX6;P2RX6 | NR_003608;NM_005446;NM_001159554 |
| NA | NA | APOL1;APOL1;APOL1 | NM_001136541;NM_003661;NM_001136540;NM_145343 |

FIGURE 9E-4

| UCSC_RefGene_Group | UCSC_CpG_Islands_Name | Relation_to_UCSC_CpG_Island |
|---|---|---|
| TSS1500;TSS1500 | chr1:117664180-117665148 | Island |
| TSS1500;5'UTR;1stExon | chr1:236558459-236559336 | N_Shore |
| TSS1500 | | |
| TSS1500;TSS1500;TSS1500 | chr1:17337829-17338590 | S_Shore |
| TSS1500 | chr1:26856191-26856684 | N_Shore |
| TSS1500 | chr1:28240584-28241535 | S_Shore |
| TSS1500 | chr2:97202313-97203787 | N_Shore |
| TSS200;TSS200;5'UTR;TSS200 | chr2:106014878-106015884 | Island |
| Body | | |
| TSS200;Body | chr2:39186777-39187968 | Island |
| TSS200;TSS200;5'UTR;TSS200 | chr2:106014878-106015884 | Island |
| 5'UTR;5'UTR;1stExon;1stExon;5'UTR;5'UTR | chr2:131513363-131514183 | Island |
| TSS200;TSS200;5'UTR;TSS200 | chr2:106014878-106015884 | Island |

FIGURE 9A-5

| UCSC_RefGene_Group | UCSC_CpG_Islands_Name | Relation_to_UCSC_CpG_Island |
|---|---|---|
| Body | chr3:187387914-187388176 | N_Shore |
| TSS1500;TSS1500;TSS1500 | chr3:53078956-53081101 | Island |
| 1stExon;Body;5'UTR;TSS1500;1stExon;5'UTR | chr3:52008943-52009339 | N_Shore |
| TSS1500 | chr3:160167184-160168200 | Island |
| Body | chr3:187387914-187388176 | N_Shore |
| | chr4:147558231-147558583 | Island |
| Body;Body;Body | chr4:84255726-84256399 | N_Shore |
| | chr5:139017133-139017668 | N_Shelf |
| | | |
| Body;3'UTR | | |
| 1stExon;5'UTR | chr6:25652380-25652709 | Island |
| TSS1500;5'UTR;5'UTR;TSS1500;1stExon | chr6:30294169-30295071 | S_Shore |
| Body;Body | chr6:147525374-147525848 | S_Shelf |
| TSS1500 | chr6:11043913-11045206 | Island |
| | | |

FIGURE 9B-5

| UCSC_RefGene_Group | UCSC_CpG_Islands_Name | Relation_to_UCSC_CpG_Island |
|---|---|---|
| 1stExon | chr6:18122250-18122994 | Island |
| Body | chr7:131012460-131013190 | N_Shelf |
| Body;TSS1500 | chr7:156432433-156433670 | Island |
| TSS1500 | chr7:130417912-130419378 | Island |
| TSS1500 | chr7:130417912-130419378 | Island |
| | chr7:152591458-152591706 | Island |
| TSS1500 | chr7:130417912-130419378 | Island |
| 1stExon | chr7:130417912-130419378 | Island |
| TSS1500 | chr7:130417912-130419378 | Island |
| TSS1500 | chr8:82644603-82644849 | N_Shore |
| TSS1500 | chr8:57360585-57360815 | Island |
| TSS1500;TSS1500 | | |
| Body | chr10:49674243-49674776 | N_Shore |
| Body | chr11:133800684-133800931 | N_Shelf |
| 5'UTR | chr11:12695414-12696981 | Island |

FIGURE 9C-5

| UCSC_RefGene_Group | UCSC_CpG_Islands_Name | Relation_to_UCSC_CpG_Island |
|---|---|---|
| 1stExon | chr11:66083572-66083782 | Island |
| 1stExon | chr11:66083572-66083782 | N_Shore |
| 1stExon | chr11:66083572-66083782 | Island |
| TSS200 | chr11:9025095-9026315 | Island |
| | chr11:10324353-10324828 | N_Shore |
| | chr12:11653232-11653775 | Island |
| | chr12:81471569-81472119 | N_Shelf |
| Body;Body | chr12:54447744-54448091 | S_Shore |
| TSS1500 | chr12:30848264-30849016 | S_Shore |
| | chr14:61108954-61109786 | N_Shore |
| 5'UTR | chr15:79576059-79576270 | Island |
| Body | chr15:31775540-31776988 | Island |
| TSS1500;TSS1500;TSS1500 | chr15:72522131-72524238 | S_Shore |

FIGURE 9D-5

| UCSC_RefGene_Group | UCSC_CpG_Islands_Name | Relation_to_UCSC_CpG_Island |
|---|---|---|
| 5'UTR | chr15:33009530-33011696 | Island |
| TSS1500;TSS1500;5'UTR | chr16:30076310-30077872 | N_Shore |
| 3'UTR;3'UTR;3'UTR;3'UTR | chr17:28562387-28563186 | Island |
| 1stExon;5'UTR | | |
| Body;Body | | |
| 5'UTR | | |
| 1stExon;Body | chr19:15342626-15343181 | Island |
| Body;Body | chr20:44657463-44659243 | Island |
| TSS1500;TSS1500;TSS1500 | chr22:21368197-21368771 | S_Shore |
| TSS200;TSS200;TSS200 | | |

FIGURE 9E-5

| Phantom | DMR | Enhancer | HMM_Island | Regulatory_Feature_Name |
|---|---|---|---|---|
| | | NA | | 1:117663907-117665512 |
| | | NA | 1:117465578-117466781 | |
| | CDMR | TRUE | 1:206063625-206063801 | |
| | | NA | | 1:169555452-169556050 |
| | | TRUE | | 1:173369020-17338827 |
| | | NA | | 1:26855689-26857507 |
| | | NA | 1:28113187-28114165 | 1:28240552-28241702 |
| | | NA | | 2:97202196-97202767 |
| | | NA | 2:105381311-105382817 | 2:106014507-106016259 |
| | | TRUE | 2:39040222-39041697 | 2:230451331-230452578 |
| | | TRUE | 2:105381311-105382817 | 2:39187021-39187940 |
| | | NA | 2:105381311-105382817 | 2:106014507-106016259 |
| | DMR | NA | 2:131229834-131230653 | 2:131513688-131513993 |
| | | NA | 2:105381311-105382817 | 2:106014507-106016259 |
| | | NA | | |

FIGURE 9A-6

| Phantom | DMR | Enhancer | HMM_Island | Regulatory_Feature_Name |
|---|---|---|---|---|
| high-CpG:53054999-53055997 | RDMR | TRUE | 3:188870246-188870359 | |
| | | NA | 3:53053856-53056190 | |
| | | TRUE | 3:51982751-51985402 | 3:52007848-52009460 |
| | | NA | 3:161649892-161650878 | 3:160166409-160168278 |
| | RDMR | TRUE | 3:188870501-188870889 | |
| | | NA | 4:147777501-147778016 | 4:147557996-147558356 |
| | | NA | | 4:84255006-84256489 |
| | | TRUE | | 5:139013288-139013559 |
| | RDMR | NA | 5:140400003-140400154 | |
| | | NA | | 6:31104495-31106407 |
| | DMR | NA | 6:25760360-25760750 | 6:25652510-25652746 |
| | | NA | | |
| | | NA | | 6:147528521-147528685 |
| | | NA | 6:11151611-11153237 | 6:110441102-11044892 |
| | | TRUE | | 6:10510346-10511316 |

FIGURE 9B-6

| Phantom | DMR | Enhancer | HMM_Island | Regulatory_Feature_Name |
|---|---|---|---|---|
| | | TRUE | 6:18230230-18231229 | 6:18122473-18123542 |
| | DMR | NA | | 7:131008672-131009115 |
| | | NA | 7:156125195-156126707 | 7:156432754-156434135 |
| | | NA | 7:130068467-130069793 | 7:130418325-130419878 |
| | | NA | 7:130068467-130069793 | 7:130418325-130419878 |
| | | NA | 7:152222028-152222744 | 7:152590901-152592150 |
| | | NA | 7:130068467-130069793 | 7:130418325-130419878 |
| | DMR | NA | 7:130068467-130069793 | |
| | | NA | | 7:130418325-130419878 |
| | | NA | 8:57522950-57523369 | 8:57360377-57362115 |
| | | NA | | |
| | | NA | | |
| | | TRUE | 11:133303046-133303162 | 11:133797084-133799070 |
| | | NA | 11:126651991-12653557 | 11:12695339-12696865 |

FIGURE 9C-6

| Phantom | DMR | Enhancer | HMM_Island | Regulatory_Feature_Name |
|---|---|---|---|---|
| | | NA | 11:65840060-65841164 | |
| | RDMR | NA | 11:65840060-65841164 | |
| | | NA | 11:65840060-65841164 | |
| | DMR | NA | 11:8981699-8983012 | |
| | | NA | | |
| | | NA | 12:11544500-11545229 | 12:11653353-11654101 |
| | | NA | | |
| | | NA | 12:52734084-52734533 | 12:54447856-54448358 |
| | | NA | 12:30739425-30740382 | |
| | | NA | | |
| | RDMR | TRUE | 14:60177929-60179820 | |
| | RDMR | NA | 15:77363046-77363443 | |
| | | NA | 15:29562601-29564280 | |
| | | NA | | |

FIGURE 9D-6

| Phantom | DMR | Enhancer | HMM_Island | Regulatory_Feature_Name |
|---|---|---|---|---|
| | | NA | 15:30796823-30799072 | |
| | | NA | | |
| | | TRUE | | |
| | | NA | 17:59752099-59752445 | 17:62397669-62399390 |
| | | NA | | 17:40176771-40177869 |
| | DMR | NA | 17:25586344-25587312 | 17:28562266-28563419 |
| | | NA | 17:53018213-53018286 | |
| | DMR | NA | | 18:66388995-66389733 |
| | DMR | NA | 19:15203635-15204238 | 19:15341951-15343455 |
| | | NA | 20:44090882-44092713 | 20:44657985-44658436 |
| | | TRUE | | 22:21368080-21369261 |
| | | NA | | 22:36648819-36649508 |

FIGURE 9E-6

| Regulatory_Feature_Group | DHS | RANGE_START | RANGE_END | RANGE_GB | SPOT_ID |
|---|---|---|---|---|---|
| Promoter_Associated | NA | 117665053 | 117665176 | NC_000001.10 | |
| | NA | 236557682 | 236557805 | NC_000001.10 | |
| | TRUE | 207997020 | 207997143 | NC_000001.10 | |
| Unclassified_Cell_type_specific | NA | 169556022 | 169556145 | NC_000001.10 | |
| Promoter_Associated | NA | 17338766 | 17338889 | NC_000001.10 | |
| Promoter_Associated | NA | 26855765 | 26855888 | NC_000001.10 | |
| NonGene_Associated | NA | 28241577 | 28241700 | NC_000001.10 | |
| Promoter_Associated | NA | 97202260 | 97202383 | NC_000002.11 | |
| Unclassified_Cell_type_specific | TRUE | 106015739 | 106015862 | NC_000002.11 | |
| Unclassified_Cell_type_specific | NA | 230452311 | 230452434 | NC_000002.11 | |
| Unclassified | TRUE | 39187539 | 39187662 | NC_000002.11 | |
| Unclassified_Cell_type_specific | TRUE | 106015767 | 106015890 | NC_000002.11 | |
| Unclassified_Cell_type_specific | TRUE | 131513927 | 131514050 | NC_000002.11 | |
| Unclassified_Cell_type_specific | TRUE | 106015771 | 106015894 | NC_000002.11 | |
| | NA | 30561970 | 30562093 | NC_000002.11 | |

FIGURE 9A-7

| Regulatory_Feature_Group | DHS | RANGE_START | RANGE_END | RANGE_GB | SPOT_ID |
|---|---|---|---|---|---|
| | NA | 187387650 | 187387773 | NC_000003.11 | |
| | NA | 53080440 | 53080563 | NC_000003.11 | |
| Promoter_Associated | NA | 52008487 | 52008610 | NC_000003.11 | |
| Promoter_Associated | NA | 160167977 | 160168100 | NC_000003.11 | |
| | NA | 187387866 | 187387989 | NC_000003.11 | |
| Unclassified_Cell_type_specific | TRUE | 147558239 | 147558362 | NC_000004.11 | |
| Unclassified_Cell_type_specific | NA | 84255411 | 84255534 | NC_000004.11 | |
| Unclassified | NA | 139013317 | 139013440 | NC_000005.9 | |
| | NA | 140419819 | 140419942 | NC_000005.9 | |
| Unclassified | NA | 31105711 | 31105834 | NC_000006.11 | |
| Unclassified_Cell_type_specific | TRUE | 25652602 | 25652725 | NC_000006.11 | |
| | NA | 30295466 | 30295589 | NC_000006.11 | |
| Unclassified_Cell_type_specific | NA | 147528521 | 147528644 | NC_000006.11 | |
| Unclassified_Cell_type_specific | TRUE | 11044877 | 11045000 | NC_000006.11 | |
| Unclassified | NA | 10510789 | 10510912 | NC_000006.11 | |

FIGURE 9B-7

| Regulatory_Feature_Group | DHS | RANGE_START | RANGE_END | RANGE_GB | SPOT_ID |
|---|---|---|---|---|---|
| Promoter_Associated | TRUE | 18122719 | 18122842 | NC_000006.11 | |
| Unclassified_Cell_type_specific | NA | 131008743 | 131008866 | NC_000007.13 | |
| Unclassified | NA | 156433108 | 156433231 | NC_000007.13 | |
| Unclassified | TRUE | 130419159 | 130419282 | NC_000007.13 | |
| Unclassified | TRUE | 130419133 | 130419256 | NC_000007.13 | |
| Unclassified | TRUE | 152591698 | 152591821 | NC_000007.13 | |
| Unclassified | TRUE | 130419116 | 130419239 | NC_000007.13 | |
| Unclassified | TRUE | 130418324 | 130418447 | NC_000007.13 | |
| Unclassified | TRUE | 130419173 | 130419296 | NC_000007.13 | |
| | NA | 82644012 | 82644135 | NC_000008.10 | |
| Unclassified_Cell_type_specific | TRUE | 57360613 | 57360736 | NC_000008.10 | |
| | NA | 98062687 | 98062810 | NC_000010.10 | |
| | NA | 49673534 | 49673657 | NC_000010.10 | |
| Promoter_Associated | NA | 133797911 | 133798034 | NC_000011.9 | |
| Unclassified_Cell_type_specific | NA | 12696758 | 12696881 | NC_000011.9 | |

FIGURE 9C-7

| Regulatory_Feature_Group | DHS | RANGE_START | RANGE_END | RANGE_GB | SPOT_ID |
|---|---|---|---|---|---|
| | NA | 66083697 | 66083820 | NC_000011.9 | |
| | NA | 66083541 | 66083664 | NC_000011.9 | |
| | NA | 66083573 | 66083696 | NC_000011.9 | |
| | TRUE | 9025767 | 9025890 | NC_000011.9 | |
| | NA | 10323902 | 10324025 | NC_000011.9 | |
| Unclassified | TRUE | 11653486 | 11653609 | NC_000012.11 | |
| | NA | 81468232 | 81468355 | NC_000012.11 | |
| Unclassified | TRUE | 54448265 | 54448388 | NC_000012.11 | |
| | NA | 30849114 | 30849237 | NC_000012.11 | |
| | NA | 40666907 | 40667030 | NC_000013.10 | |
| | NA | 61108227 | 61108350 | NC_000014.8 | |
| | TRUE | 79576060 | 79576183 | NC_000015.9 | |
| | NA | 31775895 | 31776018 | NC_000015.9 | |
| | NA | 72525012 | 72525135 | NC_000015.9 | |

FIGURE 9D-7

| Regulatory_Feature_Group | DHS | RANGE_START | RANGE_END | RANGE_GB | SPOT_ID |
|---|---|---|---|---|---|
| | TRUE | 33010536 | 33010659 | NC_000015.9 | |
| | NA | 30075192 | 30075315 | NC_000016.9 | |
| | NA | 85429035 | 85429158 | NC_000016.9 | |
| Unclassified | TRUE | 62398693 | 62398816 | NC_000017.10 | |
| Gene_Associated | NA | 40177415 | 40177538 | NC_000017.10 | |
| Unclassified_Cell_type_specific | TRUE | 28562685 | 28562808 | NC_000017.10 | |
| | NA | 55663225 | 55663348 | NC_000017.10 | |
| Unclassified_Cell_type_specific | NA | 66389420 | 66389543 | NC_000018.9 | |
| Unclassified_Cell_type_specific | NA | 15342982 | 15343105 | NC_000019.9 | |
| Unclassified_Cell_type_specific | TRUE | 44658225 | 44658348 | NC_000020.10 | |
| Promoter_Associated | NA | 21369010 | 21369133 | NC_000022.10 | |
| Unclassified | TRUE | 36648973 | 36649096 | NC_000022.10 | |

FIGURE 9E-7

SEQUENCE LISTING

<160> NUMBER OF SEQ ID NOS: 240

<210> SEQ ID NO 1
<211> LENGTH: 50
<212> TYPE: DNA
<213> ORGANISM: Artificial Sequence
<220> FEATURE:
<223> OTHER INFORMATION: Probe sequence

```
<400> SEQUENCE: 1
aaaataaaaa catctcaaac tcacattaca aaaaccaatt caaaaaacca            50

<210> SEQ ID NO 2
<211> LENGTH: 50
<212> TYPE: DNA
<213> ORGANISM: Artificial Sequence
<220> FEATURE:
<223> OTHER INFORMATION: Probe sequence

<400> SEQUENCE: 2
tttcatctaa aaaatttaac tctaaccaaa caaccaacra acatcttctc            50

<210> SEQ ID NO 3
<211> LENGTH: 50
<212> TYPE: DNA
<213> ORGANISM: Artificial Sequence
<220> FEATURE:
<223> OTHER INFORMATION: Probe sequence

<400> SEQUENCE: 3
caaaactaca acaccttaca acaaaaccaa aatttaaatc tacacaaaca            50

<210> SEQ ID NO 4
<211> LENGTH: 50
<212> TYPE: DNA
<213> ORGANISM: Artificial Sequence
<220> FEATURE:
<223> OTHER INFORMATION: Probe Sequence

<400> SEQUENCE: 4
tccaaatata aacttaaacc caaacaaacc tcaaatcaat aataacraac            50

<210> SEQ ID NO 5
<211> LENGTH: 50
<212> TYPE: DNA
<213> ORGANISM: Artificial Sequence
<220> FEATURE:
<223> OTHER INFORMATION: Probe sequence

<400> SEQUENCE: 5
cacaaaaaac tactacraaa atcacacaaa aaaatactta tcaactaaac            50

<210> SEQ ID NO 6
<211> LENGTH: 50
<212> TYPE: DNA
<213> ORGANISM: Artificial Sequence
<220> FEATURE:
<223> OTHER INFORMATION: Probe sequence

<400> SEQUENCE: 6
ataataacaa ctactaatac ccatcttaac ctaaaacact aaaatcrccc            50

<210> SEQ ID NO 7
<211> LENGTH: 50
<212> TYPE: DNA
<213> ORGANISM: Artificial Sequence
<220> FEATURE:
<223> OTHER INFORMATION: Probe sequence

<400> SEQUENCE: 7
acaccrcrta aaattactta ttcttttaca taaaaaatca cattctcttc            50

<210> SEQ ID NO 8
<211> LENGTH: 50
```

<212> TYPE: DNA
<213> ORGANISM: Artificial Sequence
<220> FEATURE:
<223> OTHER INFORMATION: Probe sequence

<400> SEQUENCE: 8
ctaaactttc aaactaaaac ccctaaaata aactcctcac ctaaaaaaac    50

<210> SEQ ID NO 9
<211> LENGTH: 50
<212> TYPE: DNA
<213> ORGANISM: Artificial Sequence
<220> FEATURE:
<223> OTHER INFORMATION: Probe sequence

<400> SEQUENCE: 9
caaaactcct ttcttcrtac cctccraatc ttaaaaacac aataattatc    50

<210> SEQ ID NO 10
<211> LENGTH: 50
<212> TYPE: DNA
<213> ORGANISM: Artificial Sequence
<220> FEATURE:
<223> OTHER INFORMATION: Probe sequence

<400> SEQUENCE: 10
rcaaacccct taaaaaaaaa ccaatacaac aaattaatta accaaaccac    50

<210> SEQ ID NO 11
<211> LENGTH: 50
<212> TYPE: DNA
<213> ORGANISM: Artificial Sequence
<220> FEATURE:
<223> OTHER INFORMATION: Probe sequence

<400> SEQUENCE: 11
acacaaaaac tctttaaaaa aacaactcaa caacttaacc ttaccataca    50

<210> SEQ ID NO 12
<211> LENGTH: 50
<212> TYPE: DNA
<213> ORGANISM: Artificial Sequence
<220> FEATURE:
<223> OTHER INFORMATION: Probe sequence

<400> SEQUENCE: 12
cttaaaaaca caataattat caaaaacatc acctccaaca taaactctca    50

<210> SEQ ID NO 13
<211> LENGTH: 50
<212> TYPE: DNA
<213> ORGANISM: Artificial Sequence
<220> FEATURE:
<223> OTHER INFORMATION: Probe sequence

<400> SEQUENCE: 13
tctcaaaacc ttaacaactt accactaaaa acccacaata caacaaaaca    50

<210> SEQ ID NO 14
<211> LENGTH: 50
<212> TYPE: DNA
<213> ORGANISM: Artificial Sequence
<220> FEATURE:
<223> OTHER INFORMATION: Probe sequence

<400> SEQUENCE: 14
aaaacacaat aattatcaaa aacatcacct ccaacataaa ctctcaaaca       50

<210> SEQ ID NO 15
<211> LENGTH: 50
<212> TYPE: DNA
<213> ORGANISM: Artificial Sequence
<220> FEATURE:
<223> OTHER INFORMATION: Probe sequence

<400> SEQUENCE: 15
aaaactaact cttcctctac cacatataat catcaacaaa tcctataaat       50

<210> SEQ ID NO 16
<211> LENGTH: 50
<212> TYPE: DNA
<213> ORGANISM: Artificial Sequence
<220> FEATURE:
<223> OTHER INFORMATION: Probe sequence

<400> SEQUENCE: 16
crtttcaaca cctaaatcaa crcttcccaa aatcaacacc aaaaataaac       50

<210> SEQ ID NO 17
<211> LENGTH: 50
<212> TYPE: DNA
<213> ORGANISM: Artificial Sequence
<220> FEATURE:
<223> OTHER INFORMATION: Probe sequence

<400> SEQUENCE: 17
tatctacaac ccraaataaa acrcaaacta aatcraaact aaaccaaaac       50

<210> SEQ ID NO 18
<211> LENGTH: 50
<212> TYPE: DNA
<213> ORGANISM: Artificial Sequence
<220> FEATURE:
<223> OTHER INFORMATION: Probe sequence

<400> SEQUENCE: 18
taacrtttac tacttattac tactctacaa aaattaacaa catctaaccc       50

<210> SEQ ID NO 19
<211> LENGTH: 50
<212> TYPE: DNA
<213> ORGANISM: Artificial Sequence
<220> FEATURE:
<223> OTHER INFORMATION: Probe sequence

<400> SEQUENCE: 19
atataacacc aaataaaaaa taattcctca aaaaccatca accaccaaca       50

<210> SEQ ID NO 20
<211> LENGTH: 50
<212> TYPE: DNA
<213> ORGANISM: Artificial Sequence
<220> FEATURE:
<223> OTHER INFORMATION: Probe sequence

<400> SEQUENCE: 20
aaaacccaaa aaaacaccaa aactctttaa aaaaactaaa catcccttac       50

<210> SEQ ID NO 21
<211> LENGTH: 50
<212> TYPE: DNA
<213> ORGANISM: Artificial Sequence
<220> FEATURE:
<223> OTHER INFORMATION: Probe sequence

<400> SEQUENCE: 21
actatcctca aaaccacca aaatactaaa aaaaacaaca acaacaaaca                50

<210> SEQ ID NO 22
<211> LENGTH: 50
<212> TYPE: DNA
<213> ORGANISM: Artificial Sequence
<220> FEATURE:
<223> OTHER INFORMATION: Probe sequence

<400> SEQUENCE: 22
aaatatatta cattataata acatctaaac tcttaatata actatcaccc                50

<210> SEQ ID NO 23
<211> LENGTH: 50
<212> TYPE: DNA
<213> ORGANISM: Artificial Sequence
<220> FEATURE:
<223> OTHER INFORMATION: Probe sequence

<400> SEQUENCE: 23
taaaacctaa ttcacctatt cacacacaaa aacataacta ccataacaac                50

<210> SEQ ID NO 24
<211> LENGTH: 50
<212> TYPE: DNA
<213> ORGANISM: Artificial Sequence
<220> FEATURE:
<223> OTHER INFORMATION: Probe sequence

<400> SEQUENCE: 24
tacaaccaca catccaaaac taacaaaacr aacactctac caaatcctac                50

<210> SEQ ID NO 25
<211> LENGTH: 50
<212> TYPE: DNA
<213> ORGANISM: Artificial Sequence
<220> FEATURE:
<223> OTHER INFORMATION: Probe sequence

<400> SEQUENCE: 25
aaacctaaac ccaccccraa aaaaatacaa ataataaaat cccctcaacc                50

<210> SEQ ID NO 26
<211> LENGTH: 50
<212> TYPE: DNA
<213> ORGANISM: Artificial Sequence
<220> FEATURE:
<223> OTHER INFORMATION: Probe sequence

<400> SEQUENCE: 26
caaaaaatac rataaaaaaa tccttcccaa aattatctaa atccttccrc                50

<210> SEQ ID NO 27
<211> LENGTH: 50
<212> TYPE: DNA
<213> ORGANISM: Artificial Sequence
<220> FEATURE:
<223> OTHER INFORMATION: Probe sequence

<400> SEQUENCE: 27
ttaccaatct aaatccrtcc taatacctta ctatacatac aattctactc                50

<210> SEQ ID NO 28
<211> LENGTH: 50
<212> TYPE: DNA
<213> ORGANISM: Artificial Sequence
<220> FEATURE:
<223> OTHER INFORMATION: Probe sequence

<400> SEQUENCE: 28
caccrtctca aaaattaaca aattcaaatc taacctaatc aaattttatc    50

<210> SEQ ID NO 29
<211> LENGTH: 50
<212> TYPE: DNA
<213> ORGANISM: Artificial Sequence
<220> FEATURE:
<223> OTHER INFORMATION: Probe sequence

<400> SEQUENCE: 29
tctaaacaac aaataaatat tcctaaaact ccataaacat taaaccacca    50

<210> SEQ ID NO 30
<211> LENGTH: 50
<212> TYPE: DNA
<213> ORGANISM: Artificial Sequence
<220> FEATURE:
<223> OTHER INFORMATION: Probe sequence

<400> SEQUENCE: 30
attttcacrc catcataaca ttttattcct cacctaacta aaaacaactc    50

<210> SEQ ID NO 31
<211> LENGTH: 50
<212> TYPE: DNA
<213> ORGANISM: Artificial Sequence
<220> FEATURE:
<223> OTHER INFORMATION: Probe sequence

<400> SEQUENCE: 31
actcraatac aaaatatact ttaaaaaatt taaccaccra caacaacrac    50

<210> SEQ ID NO 32
<211> LENGTH: 50
<212> TYPE: DNA
<213> ORGANISM: Artificial Sequence
<220> FEATURE:
<223> OTHER INFORMATION: Probe sequence

<400> SEQUENCE: 32
aattcaaaat tttcaaataa taataaacaa ctactatctc aaacacatac    50

<210> SEQ ID NO 33
<211> LENGTH: 50
<212> TYPE: DNA
<213> ORGANISM: Artificial Sequence
<220> FEATURE:
<223> OTHER INFORMATION: Probe sequence

<400> SEQUENCE: 33
actaaaacac aaaacatac aaacacccaa acctcatata ataaaaacca    50

<210> SEQ ID NO 34
<211> LENGTH: 50
<212> TYPE: DNA
<213> ORGANISM: Artificial Sequence
<220> FEATURE:
<223> OTHER INFORMATION: Probe sequence

```
<400> SEQUENCE: 34
atctccacat tctttcttct accaacaaac caaataataa taacaaaaca              50

<210> SEQ ID NO 35
<211> LENGTH: 50
<212> TYPE: DNA
<213> ORGANISM: Artificial Sequence
<220> FEATURE:
<223> OTHER INFORMATION: Probe sequence

<400> SEQUENCE: 35
atatttaaca acctcaaaaa ttatcttatc tccrcrttct ttcttctacc              50

<210> SEQ ID NO 36
<211> LENGTH: 50
<212> TYPE: DNA
<213> ORGANISM: Artificial Sequence
<220> FEATURE:
<223> OTHER INFORMATION: Probe sequence

<400> SEQUENCE: 36
aattcaaaac tttaaacccc caacactcta caaacaaaaa acaaaacaca              50

<210> SEQ ID NO 37
<211> LENGTH: 50
<212> TYPE: DNA
<213> ORGANISM: Artificial Sequence
<220> FEATURE:
<223> OTHER INFORMATION: Probe sequence

<400> SEQUENCE: 37
raccccccra ctaaatcata tttaacaacc tcaaaaatta tcttatctcc              50

<210> SEQ ID NO 38
<211> LENGTH: 50
<212> TYPE: DNA
<213> ORGANISM: Artificial Sequence
<220> FEATURE:
<223> OTHER INFORMATION: Probe sequence

<400> SEQUENCE: 38
ataacactta acaacaaata taacaaacct cctccaaaac acctaatcca              50

<210> SEQ ID NO 39
<211> LENGTH: 50
<212> TYPE: DNA
<213> ORGANISM: Artificial Sequence
<220> FEATURE:
<223> OTHER INFORMATION: Probe sequence

<400> SEQUENCE: 39
tcttctacca acaaaccaaa taataataac aaaacaaaac tccccaatca              50

<210> SEQ ID NO 40
<211> LENGTH: 50
<212> TYPE: DNA
<213> ORGANISM: Artificial Sequence
<220> FEATURE:
<223> OTHER INFORMATION: Probe sequence

<400> SEQUENCE: 40
acaaccccat ttaaaatttt taatacacta aaaatcattc aaaaaacttc              50

<210> SEQ ID NO 41
```

```
<211> LENGTH: 50
<212> TYPE: DNA
<213> ORGANISM: Artificial Sequence
<220> FEATURE:
<223> OTHER INFORMATION: Probe sequence

<400> SEQUENCE: 41
caaaaaacta atttctacaa tcactaaaac ctacaacaac actactccca                    50

<210> SEQ ID NO 42
<211> LENGTH: 50
<212> TYPE: DNA
<213> ORGANISM: Artificial Sequence
<220> FEATURE:
<223> OTHER INFORMATION: Probe sequence

<400> SEQUENCE: 42
tattatttaa aacttttact atctccaaaa cacrtaaaca cctcacaacc                    50

<210> SEQ ID NO 43
<211> LENGTH: 50
<212> TYPE: DNA
<213> ORGANISM: Artificial Sequence
<220> FEATURE:
<223> OTHER INFORMATION: Probe sequence

<400> SEQUENCE: 43
craaaaaaac crcatttcaa aacacttact cctaaatacc taatataatc                    50

<210> SEQ ID NO 44
<211> LENGTH: 50
<212> TYPE: DNA
<213> ORGANISM: Artificial Sequence
<220> FEATURE:
<223> OTHER INFORMATION: Probe sequence

<400> SEQUENCE: 44
tttccacaca taactcctca ctactttatt acctaaacca aaaaaaaaca                    50

<210> SEQ ID NO 45
<211> LENGTH: 50
<212> TYPE: DNA
<213> ORGANISM: Artificial Sequence
<220> FEATURE:
<223> OTHER INFORMATION: Probe sequence

<400> SEQUENCE: 45
acacaccctc aaacacctta aacaaaatac actaaaaaac caaaaattca                    50

<210> SEQ ID NO 46
<211> LENGTH: 50
<212> TYPE: DNA
<213> ORGANISM: Artificial Sequence
<220> FEATURE:
<223> OTHER INFORMATION: Probe sequence

<400> SEQUENCE: 46
taatcacata tcctaccact acactaaaaa cttccaacta acaacaaaca                    50

<210> SEQ ID NO 47
<211> LENGTH: 50
<212> TYPE: DNA
<213> ORGANISM: Artificial Sequence
<220> FEATURE:
<223> OTHER INFORMATION: Probe sequence

<400> SEQUENCE: 47
```
craaaaataa tccrcaccrc tatataaaca caaataaata ccaaattacc                50

<210> SEQ ID NO 48
<211> LENGTH: 50
<212> TYPE: DNA
<213> ORGANISM: Artificial Sequence
<220> FEATURE:
<223> OTHER INFORMATION: Probe sequence

<400> SEQUENCE: 48
atctactaac acacaccaac aatctaacac tcatctatat ccacacaaca                50

<210> SEQ ID NO 49
<211> LENGTH: 50
<212> TYPE: DNA
<213> ORGANISM: Artificial Sequence
<220> FEATURE:
<223> OTHER INFORMATION: Probe sequence

<400> SEQUENCE: 49
aaaaacaaca acactaataa aaactaaccc aacaatccaa aaatccacca                50

<210> SEQ ID NO 50
<211> LENGTH: 50
<212> TYPE: DNA
<213> ORGANISM: Artificial Sequence
<220> FEATURE:
<223> OTHER INFORMATION: Probe sequence

<400> SEQUENCE: 50
cacaaaactt taaaaaacac tctaacccct actactcacc catacaaaca                50

<210> SEQ ID NO 51
<211> LENGTH: 50
<212> TYPE: DNA
<213> ORGANISM: Artificial Sequence
<220> FEATURE:
<223> OTHER INFORMATION: Probe sequence

<400> SEQUENCE: 51
aactctacct caaaaaactc aaaaccatcr tactaaacca acaaaaactc                50

<210> SEQ ID NO 52
<211> LENGTH: 50
<212> TYPE: DNA
<213> ORGANISM: Artificial Sequence
<220> FEATURE:
<223> OTHER INFORMATION: Probe sequence

<400> SEQUENCE: 52
tcccacttta caatctttac caaatttaat catcactaac aaaaattaac                50

<210> SEQ ID NO 53
<211> LENGTH: 50
<212> TYPE: DNA
<213> ORGANISM: Artificial Sequence
<220> FEATURE:
<223> OTHER INFORMATION: Probe sequence

<400> SEQUENCE: 53
attacccatt ctcrctcrta aatccaattc aattatacta acccaaaatc                50

<210> SEQ ID NO 54
<211> LENGTH: 50
<212> TYPE: DNA

<213> ORGANISM: Artificial Sequence
<220> FEATURE:
<223> OTHER INFORMATION: Probe sequence

<400> SEQUENCE: 54
caacaaatct atcttaaaac aaacccaatt acrataccca tacaattctc         50

<210> SEQ ID NO 55
<211> LENGTH: 50
<212> TYPE: DNA
<213> ORGANISM: Artificial Sequence
<220> FEATURE:
<223> OTHER INFORMATION: Probe sequence

<400> SEQUENCE: 55
gctacttccc taaattaaac aaaccattat tacctctcac ctaaactact         50

<210> SEQ ID NO 56
<211> LENGTH: 50
<212> TYPE: DNA
<213> ORGANISM: Artificial Sequence
<220> FEATURE:
<223> OTHER INFORMATION: Probe sequence

<400> SEQUENCE: 56
tatctaactc aaccccttta aatattcttc caaataaaat tattaaattc         50

<210> SEQ ID NO 57
<211> LENGTH: 50
<212> TYPE: DNA
<213> ORGANISM: Artificial Sequence
<220> FEATURE:
<223> OTHER INFORMATION: Probe sequence

<400> SEQUENCE: 57
cccatactcr accttctaaa aaatacccac aaacactaac aataataaac         50

<210> SEQ ID NO 58
<211> LENGTH: 50
<212> TYPE: DNA
<213> ORGANISM: Artificial Sequence
<220> FEATURE:
<223> OTHER INFORMATION: Probe sequence

<400> SEQUENCE: 58
aactataact ctacaacaac aacaaacaat tctactacaa atacataaca         50

<210> SEQ ID NO 59
<211> LENGTH: 50
<212> TYPE: DNA
<213> ORGANISM: Artificial Sequence
<220> FEATURE:
<223> OTHER INFORMATION: Probe sequence

<400> SEQUENCE: 59
cactacaccc aaacaattta aaactttaaa atacaatata atccaacatc         50

<210> SEQ ID NO 60
<211> LENGTH: 50
<212> TYPE: DNA
<213> ORGANISM: Artificial Sequence
<220> FEATURE:
<223> OTHER INFORMATION: Probe sequence

<400> SEQUENCE: 60
crcraaaata aattataaaa aaccatcrcr aaatccttcc tactaaaacc         50

<210> SEQ ID NO 61
<211> LENGTH: 50
<212> TYPE: DNA
<213> ORGANISM: Artificial Sequence
<220> FEATURE:
<223> OTHER INFORMATION: Probe sequence

<400> SEQUENCE: 61
tcaaaatcaa actccaataa aaacccaaaa cccctaccct ctaaaaaaca          50

<210> SEQ ID NO 62
<211> LENGTH: 50
<212> TYPE: DNA
<213> ORGANISM: Artificial Sequence
<220> FEATURE:
<223> OTHER INFORMATION: Probe sequence

<400> SEQUENCE: 62
aaaaaaaacc ataaaaatct cccrtttcac aaataaacac accaaaaccc          50

<210> SEQ ID NO 63
<211> LENGTH: 50
<212> TYPE: DNA
<213> ORGANISM: Artificial Sequence
<220> FEATURE:
<223> OTHER INFORMATION: Probe sequence

<400> SEQUENCE: 63
aataactaaa aaatctatct aaatccaaaa crctaacttt aaccttcctc          50

<210> SEQ ID NO 64
<211> LENGTH: 50
<212> TYPE: DNA
<213> ORGANISM: Artificial Sequence
<220> FEATURE:
<223> OTHER INFORMATION: Probe sequence

<400> SEQUENCE: 64
aaaaacacaa aacraacaca attataaata ataaacttac tctacaaacc          50

<210> SEQ ID NO 65
<211> LENGTH: 50
<212> TYPE: DNA
<213> ORGANISM: Artificial Sequence
<220> FEATURE:
<223> OTHER INFORMATION: Probe sequence

<400> SEQUENCE: 65
aactacacaa aaaaactaat cccaaactaa acaaacaaac taacctcaca          50

<210> SEQ ID NO 66
<211> LENGTH: 50
<212> TYPE: DNA
<213> ORGANISM: Artificial Sequence
<220> FEATURE:
<223> OTHER INFORMATION: Probe sequence

<400> SEQUENCE: 66
aaaaccaccc caaactctat aatttccaaa acaaatacaa aaacaacaca          50

<210> SEQ ID NO 67
<211> LENGTH: 50
<212> TYPE: DNA
<213> ORGANISM: Artificial Sequence
<220> FEATURE:

<223> OTHER INFORMATION: Probe sequence

<400> SEQUENCE: 67
aatttctcct taaacaatcc ccacaaaaat aacaaccaaa aaaaaataca        50

<210> SEQ ID NO 68
<211> LENGTH: 50
<212> TYPE: DNA
<213> ORGANISM: Artificial Sequence
<220> FEATURE:
<223> OTHER INFORMATION: Probe sequence

<400> SEQUENCE: 68
aaaaacacca aactccacat aaaaacacac aacaacttca acaacaaaca        50

<210> SEQ ID NO 69
<211> LENGTH: 50
<212> TYPE: DNA
<213> ORGANISM: Artificial Sequence
<220> FEATURE:
<223> OTHER INFORMATION: Probe Sequence

<400> SEQUENCE: 69
aactcaactc cattaaaata ctccraacrc tatccaaaat actaaaatac        50

<210> SEQ ID NO 70
<211> LENGTH: 50
<212> TYPE: DNA
<213> ORGANISM: Artificial Sequence
<220> FEATURE:
<223> OTHER INFORMATION: Probe sequence

<400> SEQUENCE: 70
ctctcactct atacctctta attatcttac atactctaat ctttacatac        50

<210> SEQ ID NO 71
<211> LENGTH: 50
<212> TYPE: DNA
<213> ORGANISM: Artificial Sequence
<220> FEATURE:
<223> OTHER INFORMATION: Probe sequence

<400> SEQUENCE: 71
aacaaatctt tctccttaaa accacaacaa accccaacc ctaaaaatac         50

<210> SEQ ID NO 72
<211> LENGTH: 50
<212> TYPE: DNA
<213> ORGANISM: Artificial Sequence
<220> FEATURE:
<223> OTHER INFORMATION: Probe sequence

<400> SEQUENCE: 72
aaaataaaaa catctcaaac tcgcgttacg aaaaccgatt cgaaaaaccg        50

<210> SEQ ID NO 73
<211> LENGTH: 50
<212> TYPE: DNA
<213> ORGANISM: Artificial Sequence
<220> FEATURE:
<223> OTHER INFORMATION: Probe sequence

<400> SEQUENCE: 73
cgaaactacg acaccttacg acgaaaccaa aatttaaatc tacgcaaacg        50

<210> SEQ ID NO 74
<211> LENGTH: 50
<212> TYPE: DNA
<213> ORGANISM: Artificial Sequence
<220> FEATURE:
<223> OTHER INFORMATION: Probe sequence

<400> SEQUENCE: 74
acgcgaaaac tctttaaaaa aacgactcaa cgacttaacc ttaccgtacg        50

<210> SEQ ID NO 75
<211> LENGTH: 50
<212> TYPE: DNA
<213> ORGANISM: Artificial Sequence
<220> FEATURE:
<223> OTHER INFORMATION: Probe sequence

<400> SEQUENCE: 75
cttaaaaaca caataattat cgaaaacgtc gcctccgacg taaactctcg        50

<210> SEQ ID NO 76
<211> LENGTH: 50
<212> TYPE: DNA
<213> ORGANISM: Artificial Sequence
<220> FEATURE:
<223> OTHER INFORMATION: Probe sequence

<400> SEQUENCE: 76
tctcgaaacc ttaacgactt accgctaaaa acccgcaata caacaaaacg        50

<210> SEQ ID NO 77
<211> LENGTH: 50
<212> TYPE: DNA
<213> ORGANISM: Artificial Sequence
<220> FEATURE:
<223> OTHER INFORMATION: Probe sequence

<400> SEQUENCE: 77
aaaacacaat aattatcgaa aacgtcgcct ccgacgtaaa ctctcgaacg        50

<210> SEQ ID NO 78
<211> LENGTH: 50
<212> TYPE: DNA
<213> ORGANISM: Artificial Sequence
<220> FEATURE:
<223> OTHER INFORMATION: Probe sequence

<400> SEQUENCE: 78
gtataacgcc aaataaaaaa taattcctca aaaaccgtcg accaccgacg        50

<210> SEQ ID NO 79
<211> LENGTH: 50
<212> TYPE: DNA
<213> ORGANISM: Artificial Sequence
<220> FEATURE:
<223> OTHER INFORMATION: Probe sequence

<400> SEQUENCE: 79
gctatcctca aaaccgcca aaatactaaa aaaaacgaca caacgaacg        50

<210> SEQ ID NO 80
<211> LENGTH: 50
<212> TYPE: DNA
<213> ORGANISM: Artificial Sequence
<220> FEATURE:
<223> OTHER INFORMATION: Probe sequence

<400> SEQUENCE: 80
tctaaacaac gaataaatat tcctaaaact ccgtaaacgt taaaccgccg          50

<210> SEQ ID NO 81
<211> LENGTH: 50
<212> TYPE: DNA
<213> ORGANISM: Artificial Sequence
<220> FEATURE:
<223> OTHER INFORMATION: Probe sequence

<400> SEQUENCE: 81
actaaaacac gaaaacgtac aaacgcccaa acctcgtata ataaaaaccg          50

<210> SEQ ID NO 82
<211> LENGTH: 50
<212> TYPE: DNA
<213> ORGANISM: Artificial Sequence
<220> FEATURE:
<223> OTHER INFORMATION: Probe sequence

<400> SEQUENCE: 82
atctccgcgt tctttcttct accgacgaac caaataataa taacaaaacg          50

<210> SEQ ID NO 83
<211> LENGTH: 50
<212> TYPE: DNA
<213> ORGANISM: Artificial Sequence
<220> FEATURE:
<223> OTHER INFORMATION: Probe sequence

<400> SEQUENCE: 83
aattcaaaac tttaaacccc caacgctcta caaacaaaaa acgaaacgcg          50

<210> SEQ ID NO 84
<211> LENGTH: 50
<212> TYPE: DNA
<213> ORGANISM: Artificial Sequence
<220> FEATURE:
<223> OTHER INFORMATION: Probe sequence

<400> SEQUENCE: 84
ataacgctta acaacaaata taacaaacct cctccgaaac gcctaatccg          50

<210> SEQ ID NO 85
<211> LENGTH: 50
<212> TYPE: DNA
<213> ORGANISM: Artificial Sequence
<220> FEATURE:
<223> OTHER INFORMATION: Probe sequence

<400> SEQUENCE: 85
tcttctaccg acgaaccaaa taataataac aaaacgaaac tccccaatcg          50

<210> SEQ ID NO 86
<211> LENGTH: 50
<212> TYPE: DNA
<213> ORGANISM: Artificial Sequence
<220> FEATURE:
<223> OTHER INFORMATION: Probe sequence

<400> SEQUENCE: 86
caaaaaacta atttctacaa tcgctaaaac ctacaacgac gctactcccg          50

<210> SEQ ID NO 87
<211> LENGTH: 49

<212> TYPE: DNA
<213> ORGANISM: Artificial Sequence
<220> FEATURE:
<223> OTHER INFORMATION: Probe sequence

<400> SEQUENCE: 87
tttccacagt aactcctcgc tactttatta cctaaaccaa aaaaaaacg         49

<210> SEQ ID NO 88
<211> LENGTH: 50
<212> TYPE: DNA
<213> ORGANISM: Artificial Sequence
<220> FEATURE:
<223> OTHER INFORMATION: Probe sequence

<400> SEQUENCE: 88
acacaccctc gaacgcctta aacgaaatac gctaaaaaac caaaaattcg         50

<210> SEQ ID NO 89
<211> LENGTH: 50
<212> TYPE: DNA
<213> ORGANISM: Artificial Sequence
<220> FEATURE:
<223> OTHER INFORMATION: Probe sequence

<400> SEQUENCE: 89
taatcacgta tcctaccgct acactaaaaa cttccgacta acaacaaacg         50

<210> SEQ ID NO 90
<211> LENGTH: 50
<212> TYPE: DNA
<213> ORGANISM: Artificial Sequence
<220> FEATURE:
<223> OTHER INFORMATION: Probe sequence

<400> SEQUENCE: 90
atctactaac acacaccgac aatctaacac tcatctatat ccacacaacg         50

<210> SEQ ID NO 91
<211> LENGTH: 50
<212> TYPE: DNA
<213> ORGANISM: Artificial Sequence
<220> FEATURE:
<223> OTHER INFORMATION: Probe sequence

<400> SEQUENCE: 91
aaaaacgacg acgctaataa aaactaaccc gacaatccga aaatccaccg         50

<210> SEQ ID NO 92
<211> LENGTH: 50
<212> TYPE: DNA
<213> ORGANISM: Artificial Sequence
<220> FEATURE:
<223> OTHER INFORMATION: Probe sequence

<400> SEQUENCE: 92
cacgaaactt taaaaaacac tctaacccct actactcacc catacaaacg         50

<210> SEQ ID NO 93
<211> LENGTH: 50
<212> TYPE: DNA
<213> ORGANISM: Artificial Sequence
<220> FEATURE:
<223> OTHER INFORMATION: Probe sequence

<400> SEQUENCE: 93
aactataact ctacgacgac aacgaacgat tctactacga atacgtaacg        50

<210> SEQ ID NO 94
<211> LENGTH: 50
<212> TYPE: DNA
<213> ORGANISM: Artificial Sequence
<220> FEATURE:
<223> OTHER INFORMATION: Probe sequence

<400> SEQUENCE: 94
tcgaaatcaa actccgataa aaacccaaaa ccctaccct ctaaaaacg        50

<210> SEQ ID NO 95
<211> LENGTH: 50
<212> TYPE: DNA
<213> ORGANISM: Artificial Sequence
<220> FEATURE:
<223> OTHER INFORMATION: Probe sequence

<400> SEQUENCE: 95
aactacgcga aaaaactaat cccgaactaa acaaacgaac taacctcgcg        50

<210> SEQ ID NO 96
<211> LENGTH: 50
<212> TYPE: DNA
<213> ORGANISM: Artificial Sequence
<220> FEATURE:
<223> OTHER INFORMATION: Probe sequence

<400> SEQUENCE: 96
aaaaccgccc cgaactctat aatttccaaa acaaatacga aaacgacacg        50

<210> SEQ ID NO 97
<211> LENGTH: 50
<212> TYPE: DNA
<213> ORGANISM: Artificial Sequence
<220> FEATURE:
<223> OTHER INFORMATION: Probe sequence

<400> SEQUENCE: 97
aatttctcct taaacaatcc ccgcaaaaat aacaaccaaa aaaaaatacg        50

<210> SEQ ID NO 98
<211> LENGTH: 50
<212> TYPE: DNA
<213> ORGANISM: Artificial Sequence
<220> FEATURE:
<223> OTHER INFORMATION: Probe sequence

<400> SEQUENCE: 98
gaaaacacca aactccacat aaaaacgcgc aacaacttca acgacaaacg        50

<210> SEQ ID NO 99
<211> LENGTH: 122
<212> TYPE: DNA
<213> ORGANISM: Artificial Sequence
<220> FEATURE:
<223> OTHER INFORMATION: Forward Sequence

<400> SEQUENCE: 99
gggtattttt cggggtgag ggcatctcag gctcgcgtta cggggaccgg ttcgggagac        60
cgtggagccg aggtgtcgaa tggagggctt acttcggccg ggccagggag cgccaccctc        120
ct        122

```
<210> SEQ ID NO 100
<211> LENGTH: 122
<212> TYPE: DNA
<213> ORGANISM: Artificial Sequence
<220> FEATURE:
<223> OTHER INFORMATION: Forward Sequence

<400> SEQUENCE: 100
ccccagagag ctttcatcta gaaggtttga ctctggccag acaaccagcg agcatcttct      60
cgcaatctgt tgcttcttcc atggcaaact ccagagaatt aagaagccaa actcaacatc    120
gc                                                                    122

<210> SEQ ID NO 101
<211> LENGTH: 122
<212> TYPE: DNA
<213> ORGANISM: Artificial Sequence
<220> FEATURE:
<223> OTHER INFORMATION: Forward Sequence

<400> SEQUENCE: 101
acgtggggga agaaggggt tacgccatca gtcctgaag cccgtcggac cacccatcgc       60
cgcctgcgca gacccaaatc ttggtcccgc cgtaaggtgc cgcagtcccg aatgttccag    120
aa                                                                    122

<210> SEQ ID NO 102
<211> LENGTH: 122
<212> TYPE: DNA
<213> ORGANISM: Artificial Sequence
<220> FEATURE:
<223> OTHER INFORMATION: Forward Sequence

<400> SEQUENCE: 102
ttcatgagcc ggacaaagct gtatccctcc atttccacct gccaacacca cggaagcagt     60
cgtccgttac cactgacctg aggcctgcct gggtccaagc tcacacttgg agaaccttct   120
gt                                                                    122

<210> SEQ ID NO 103
<211> LENGTH: 122
<212> TYPE: DNA
<213> ORGANISM: Artificial Sequence
<220> FEATURE:
<223> OTHER INFORMATION: Forward Sequence

<400> SEQUENCE: 103
aatgcctgct tcacagagaa ctgctgcgag gatcacacaa gaaaatgctt gtcaactggg     60
cgtggtggcg catgcctgta atcccagcta ctcggagact aagccaggag aatcgcttga   120
ac                                                                    122

<210> SEQ ID NO 104
<211> LENGTH: 122
<212> TYPE: DNA
<213> ORGANISM: Artificial Sequence
<220> FEATURE:
<223> OTHER INFORMATION: Forward Sequence

<400> SEQUENCE: 104
gggtcctgat ggtggtaaca actgctgatg cccatcttgg cctggggcac tgagatcgcc     60
cggagatcac agtgttagct tcagggcggg gtagaaatta gaggataggg gatctctagg   120
gc                                                                    122
```

<210> SEQ ID NO 105
<211> LENGTH: 122
<212> TYPE: DNA
<213> ORGANISM: Artificial Sequence
<220> FEATURE:
<223> OTHER INFORMATION: Forward Sequence

<400> SEQUENCE: 105
ctagcctcac agcaccgcgt ggagttgctt gttcttttac ataggaggtc acattctctt    60
cgtgtaatgc caccaatggt gccgattctc cccagtgggg ctgtgagaaa cctacgccct   120
ct                                                                  122

<210> SEQ ID NO 106
<211> LENGTH: 122
<212> TYPE: DNA
<213> ORGANISM: Artificial Sequence
<220> FEATURE:
<223> OTHER INFORMATION: Forward Sequence

<400> SEQUENCE: 106
agttttgcct ccagggaaac tgaggcacaa ggcagcaatg attactgagg gtcctgcctc    60
cgctcctcta ggtgaggagc ctattccagg ggctccagtc tgaaagccta gaggcgaggg   120
gc                                                                  122

<210> SEQ ID NO 107
<211> LENGTH: 122
<212> TYPE: DNA
<213> ORGANISM: Artificial Sequence
<220> FEATURE:
<223> OTHER INFORMATION: Forward Sequence

<400> SEQUENCE: 107
cctttgtttg ccagggctcc tttcttcgtg ccctccgggt cttgggagca cagtagttat    60
cgggagcgtc gcctccggcg tgggctctcg ggcgcgagtt tcggacgagg cctgggcgcg   120
gt                                                                  122

<210> SEQ ID NO 108
<211> LENGTH: 122
<212> TYPE: DNA
<213> ORGANISM: Artificial Sequence
<220> FEATURE:
<223> OTHER INFORMATION: Forward Sequence

<400> SEQUENCE: 108
ctacagtgcc cgcaggcccc ttaaaaggga gccagtgcaa cagattggtt aaccaggcca    60
cgtgttccca gtcttctaaa atccccaaa gactggacag caaatgcccc ttaggttgca   120
tg                                                                  122

<210> SEQ ID NO 109
<211> LENGTH: 122
<212> TYPE: DNA
<213> ORGANISM: Artificial Sequence
<220> FEATURE:
<223> OTHER INFORMATION: Forward Sequence

<400> SEQUENCE: 109
agagcgctac gtcgccggcg ggcagcagca gcgcctacaa actggaggcg gcggcgcagg    60
cgcacggcaa ggccaagccg ctgagccgct ctctcaaaga gttcccgcgt gcgccgccag   120
cc                                                                  122

```
<210> SEQ ID NO 110
<211> LENGTH: 122
<212> TYPE: DNA
<213> ORGANISM: Artificial Sequence
<220> FEATURE:
<223> OTHER INFORMATION: Forward Sequence

<400> SEQUENCE: 110
tgccctccgg gtcttgggag cacagtagtt atcgggagcg tcgcctccgg cgtgggctct      60
cgggcgcgag tttcggacga ggcctgggcg cggtggcagg ggtctgccca cgccgggatc     120
tc                                                                    122

<210> SEQ ID NO 111
<211> LENGTH: 122
<212> TYPE: DNA
<213> ORGANISM: Artificial Sequence
<220> FEATURE:
<223> OTHER INFORMATION: Forward Sequence

<400> SEQUENCE: 111
ctgaccgtgg tgctgagcgc ggctcgcgct ccgacgcggt gcccgagcct gtcgcggccg      60
cgccctgctg cactgcgggc ccccagcggt aagtcgccaa ggccccgaga ggctgcgttg     120
gt                                                                    122

<210> SEQ ID NO 112
<211> LENGTH: 122
<212> TYPE: DNA
<213> ORGANISM: Artificial Sequence
<220> FEATURE:
<223> OTHER INFORMATION: Forward Sequence

<400> SEQUENCE: 112
ctccgggtct tgggagcaca gtagttatcg ggagcgtcgc ctccggcgtg ggctctcggg      60
cgcgagtttc ggacgaggcc tgggcgcggt ggcaggggtc tgcccacgcc gggatctctg     120
cc                                                                    122

<210> SEQ ID NO 113
<211> LENGTH: 122
<212> TYPE: DNA
<213> ORGANISM: Artificial Sequence
<220> FEATURE:
<223> OTHER INFORMATION: Forward Sequence

<400> SEQUENCE: 113
acccgctatc tggtggagat agagaaaggc agatggcttg aagatccaat ttggagatta      60
catccatagg acttgctgat gatcacatgt ggcagaggaa gagccagtcc tcaaatatgg     120
cc                                                                    122

<210> SEQ ID NO 114
<211> LENGTH: 122
<212> TYPE: DNA
<213> ORGANISM: Artificial Sequence
<220> FEATURE:
<223> OTHER INFORMATION: Forward Sequence

<400> SEQUENCE: 114
tcagaggtct gcgtttcagc acctgggtca gcgcttccca gggtcagcac cagggataga      60
cgccattgtc gcttcgtgcc cagacaacta cccagatttt gtaattttct tgaatgccaa     120
```

```
gt                                                                      122

<210> SEQ ID NO 115
<211> LENGTH: 122
<212> TYPE: DNA
<213> ORGANISM: Artificial Sequence
<220> FEATURE:
<223> OTHER INFORMATION: Forward Sequence

<400> SEQUENCE: 115
cgctgtggcc ccgagcggaa cggcccggaa gaggagacgc gtccccggga acccagtgcc      60
cgccctggcc cagccccgat ccagcctgcg cctcacctcg ggttgtagac agagcggcgg     120
gg                                                                     122

<210> SEQ ID NO 116
<211> LENGTH: 122
<212> TYPE: DNA
<213> ORGANISM: Artificial Sequence
<220> FEATURE:
<223> OTHER INFORMATION: Forward Sequence

<400> SEQUENCE: 116
ccagccaagt ggccttgatc gttttcccaa tgcccccgag cctgtttcct gccagtagag      60
cgggtcagat gttgccaacc tctgcagagt agcaataagc agtaaacgcc acgctctgca     120
ca                                                                     122

<210> SEQ ID NO 117
<211> LENGTH: 122
<212> TYPE: DNA
<213> ORGANISM: Artificial Sequence
<220> FEATURE:
<223> OTHER INFORMATION: Forward Sequence

<400> SEQUENCE: 117
aatccgcatg gcaccggtgg tctgggggag aggctgggcc tggcgcggga cgaggcgaag      60
cgccggtggc cgacggcttc tgaggaatta tcttttactt ggcgccacac ggggcgggc     120 ct                                                                     122

<210> SEQ ID NO 118
<211> LENGTH: 122
<212> TYPE: DNA
<213> ORGANISM: Artificial Sequence
<220> FEATURE:
<223> OTHER INFORMATION: Forward Sequence

<400> SEQUENCE: 118
tcgggagctg agggacccag aaaagcacca aaactcttta gaaggactga gcatcccttta     60 cgtccaaacc aatggggcag gagcaaggct tagggagggc tggagaatcc gggagacgtc    120
ga                                                                     122

<210> SEQ ID NO 119
<211> LENGTH: 122
<212> TYPE: DNA
<213> ORGANISM: Artificial Sequence
<220> FEATURE:
<223> OTHER INFORMATION: Forward Sequence

<400> SEQUENCE: 119
gcccgagagg atccagggaa agcagaaggg ggttaaggac catggacaga gcccgtcgcg      60
cgctcgttgc tgccgccttc cccagcactc tggcggctcc tgaggacagc ggtcccatct    120
```

```
tg                                                                        122

<210> SEQ ID NO 120
<211> LENGTH: 122
<212> TYPE: DNA
<213> ORGANISM: Artificial Sequence
<220> FEATURE:
<223> OTHER INFORMATION: Forward Sequence

<400> SEQUENCE: 120
gggagggtgg gagagggatg agggatgaga aattacctat tagatacaat gtacaacatt        60
cgggtgacag ttacactaag agcccagatg ccaccacaat gcaatatacc catggaacag       120
aa                                                                       122

<210> SEQ ID NO 121
<211> LENGTH: 122
<212> TYPE: DNA
<213> ORGANISM: Artificial Sequence
<220> FEATURE:
<223> OTHER INFORMATION: Forward Sequence

<400> SEQUENCE: 121
ttgtatttca gcccaaagcc tactggaagt gtcaagctgc cagctcccct ctgccctccc        60
cgttgctatg gcagccatgt ctctgtgtgt gaataggtga accaggctcc aggttaggac       120
ct                                                                       122

<210> SEQ ID NO 122
<211> LENGTH: 122
<212> TYPE: DNA
<213> ORGANISM: Artificial Sequence
<220> FEATURE:
<223> OTHER INFORMATION: Forward Sequence

<400> SEQUENCE: 122
caggagtgcg gtgcagccac acatccaagg ctgacagggc gggcactctg ccaagtcctg        60
cgcgctgctc gccttccaca acaccttcct cagcttcgtc tgtatttgaa gagcttagta       120
aa                                                                       122

<210> SEQ ID NO 123
<211> LENGTH: 122
<212> TYPE: DNA
<213> ORGANISM: Artificial Sequence
<220> FEATURE:
<223> OTHER INFORMATION: Forward Sequence

<400> SEQUENCE: 123
attcacgggg aatcagaggg tggagagggc gtgggtgcct ggagatgcct gggaacagaa        60
cggctgaggg gactccatta tctgtactct tcccggggtg ggtctaggtc tggctcctcc       120
tg                                                                       122

<210> SEQ ID NO 124
<211> LENGTH: 122
<212> TYPE: DNA
<213> ORGANISM: Artificial Sequence
<220> FEATURE:
<223> OTHER INFORMATION: Forward Sequence

<400> SEQUENCE: 124
ggagagcaag tcaagaaata cggtgaagga gtccttccca aagttgtcta ggtccttccg        60
```
cgccggtgcc tggtcttcgt cgtcaacacc atggacagct cccgggaacc gactctgggg    120
cg                                                                    122

<210> SEQ ID NO 125
<211> LENGTH: 122
<212> TYPE: DNA
<213> ORGANISM: Artificial Sequence
<220> FEATURE:
<223> OTHER INFORMATION: Forward Sequence

<400> SEQUENCE: 125
tcaccacttc tttgccagtc tagatccgtc ctggtgcctt actgtgcata cagttctact    60
cgtctcaggt gaggaggcca cttaatttgt aaaagactga ggaagggta ggatcaccac     120 aa                                                                    122

<210> SEQ ID NO 126
<211> LENGTH: 122
<212> TYPE: DNA
<213> ORGANISM: Artificial Sequence
<220> FEATURE:
<223> OTHER INFORMATION: Forward Sequence

<400> SEQUENCE: 126
tgtgttacta agtgaagtct actatacata gtaaatacta cgcagtcata cctttataaa    60
cgacaaaatc tgaccaggct agatctgaat ctgttaattt ctgagacggt gtgtctgaag    120
tg                                                                    122

<210> SEQ ID NO 127
<211> LENGTH: 122
<212> TYPE: DNA
<213> ORGANISM: Artificial Sequence
<220> FEATURE:
<223> OTHER INFORMATION: Forward Sequence

<400> SEQUENCE: 127
ccgcggcgtc ccctgccggc cgggcggcga tttgcaggtc cagccggcgc cggtttcgcg    60
cggcggctca acgtccacgg agccccagga atacccaccc gctgcccaga tcggcagccg    120
ct                                                                    122

<210> SEQ ID NO 128
<211> LENGTH: 122
<212> TYPE: DNA
<213> ORGANISM: Artificial Sequence
<220> FEATURE:
<223> OTHER INFORMATION: Forward Sequence

<400> SEQUENCE: 128
cttgcgcctc gaatgccacg ttgaatactc ctcatgtctt tggagacatg tccttcccct    60
cgagctgctc ccagtcaggt gaggaataaa atgctatgat ggcgtgaaaa ttctcccttg    120
gt                                                                    122

<210> SEQ ID NO 129
<211> LENGTH: 122
<212> TYPE: DNA
<213> ORGANISM: Artificial Sequence
<220> FEATURE:
<223> OTHER INFORMATION: Forward Sequence

<400> SEQUENCE: 129
tgcgccaggg cggccacgca ggccaggcag accacgtggc cgcaggacag gttgcgcggg    60

```
cgccgctgct gccggtggcc aaacttctca agcacacct  tgcactcgag caggctgatc    120
tc                                                                  122

<210> SEQ ID NO 130
<211> LENGTH: 122
<212> TYPE: DNA
<213> ORGANISM: Artificial Sequence
<220> FEATURE:
<223> OTHER INFORMATION: Forward Sequence

<400> SEQUENCE: 130
aattaaagac taattcagaa ttttcaagtg atagtaaaca actgctatct caaacacata    60
cgatataaaa tgaaaccact ggtgcctaac tgccagttct ttcactcaaa cctctgctgt   120
ga                                                                  122

<210> SEQ ID NO 131
<211> LENGTH: 122
<212> TYPE: DNA
<213> ORGANISM: Artificial Sequence
<220> FEATURE:
<223> OTHER INFORMATION: Forward Sequence

<400> SEQUENCE: 131
cgtggctgcg cccacaaagc cgccgggggc tgcggactac agcgaagccg gcgcggggct    60
cggccctcac tacacgaggc ctgggcgcct gcacgccccc gtgcttcagc ccgcggctcc   120
cg                                                                  122

<210> SEQ ID NO 132
<211> LENGTH: 122
<212> TYPE: DNA
<213> ORGANISM: Artificial Sequence
<220> FEATURE:
<223> OTHER INFORMATION: Forward Sequence

<400> SEQUENCE: 132
agaaattatc ttgtctccgc gttctttctt ctgccggcga gccaggtaat ggtaacagag    60
cgaaactccc cagtcggaac ttctgggttg cagcagcctc gccccccctc cccgcagccc   120
gc                                                                  122

<210> SEQ ID NO 133
<211> LENGTH: 122
<212> TYPE: DNA
<213> ORGANISM: Artificial Sequence
<220> FEATURE:
<223> OTHER INFORMATION: Forward Sequence

<400> SEQUENCE: 133
ccggctaagt catgtttaac agcctcagaa attatcttgt ctccgcgttc tttcttctgc    60
cggcgagcca ggtaatggta acagagcgaa actccccagt cggaacttct gggttgcagc   120
ag                                                                  122

<210> SEQ ID NO 134
<211> LENGTH: 122
<212> TYPE: DNA
<213> ORGANISM: Artificial Sequence
<220> FEATURE:
<223> OTHER INFORMATION: Forward Sequence

<400> SEQUENCE: 134
```
ccccgaggcg acgccagag ggcgcgcgcc cccactcct gcccgcgtcg gggccgcagc    60
cgcgctccgc cctttgcctg cagagcgctg ggggtttaaa gtcctgaacc catgcacggc   120
tg                                                                  122

<210> SEQ ID NO 135
<211> LENGTH: 122
<212> TYPE: DNA
<213> ORGANISM: Artificial Sequence
<220> FEATURE:
<223> OTHER INFORMATION: Forward Sequence

<400> SEQUENCE: 135
tcggaacgcg cggccccccg gctaagtcat gtttaacagc ctcagaaatt atcttgtctc    60
cgcgttcttt cttctgccgg cgagccaggt aatggtaaca gagcgaaact ccccagtcgg   120
aa                                                                  122

<210> SEQ ID NO 136
<211> LENGTH: 122
<212> TYPE: DNA
<213> ORGANISM: Artificial Sequence
<220> FEATURE:
<223> OTHER INFORMATION: Forward Sequence

<400> SEQUENCE: 136
gaaggggcat tggtggcgct tggcagcagg tgtgacagac ctcctccggg gcgcctgatc    60
cgcggcgggg gcggggcctg cccctagggc ccctccagag aacccaccag aggctgctgg   120
tg                                                                  122

<210> SEQ ID NO 137
<211> LENGTH: 122
<212> TYPE: DNA
<213> ORGANISM: Artificial Sequence
<220> FEATURE:
<223> OTHER INFORMATION: Forward Sequence

<400> SEQUENCE: 137
ctccgcgttc tttcttctgc cggcgagcca ggtaatggta acagagcgaa actccccagt    60
cggaacttct gggttgcagc agcctcgccc ccctccccg cagcccgccg cccgctggtc   120
cg                                                                  122

<210> SEQ ID NO 138
<211> LENGTH: 122
<212> TYPE: DNA
<213> ORGANISM: Artificial Sequence
<220> FEATURE:
<223> OTHER INFORMATION: Forward Sequence

<400> SEQUENCE: 138
caaacaccag ggcagcccca tttaaggttt tgatacact gaggatcatt cagaaaactt    60
cggattccta gttatagagt tgaatccaac caccaacaca ctccagaagt cctgacatta   120
gg                                                                  122

<210> SEQ ID NO 139
<211> LENGTH: 122
<212> TYPE: DNA
<213> ORGANISM: Artificial Sequence
<220> FEATURE:
<223> OTHER INFORMATION: Forward Sequence

<400> SEQUENCE: 139

```
ctgcgccctc tgcaaagggc tgatttctac agtcgctagg acctgcagcg gcgctgctcc    60
cgcggggctc cggccgcgct gcatgtccca ttatagtcgc tagagggcag cgctctcctg   120
cg                                                                  122

<210> SEQ ID NO 140
<211> LENGTH: 122
<212> TYPE: DNA
<213> ORGANISM: Artificial Sequence
<220> FEATURE:
<223> OTHER INFORMATION: Forward Sequence

<400> SEQUENCE: 140
gcaacacaga gtgctttacc catgccttaa ggcagctgtc acatgactct tcccctaata    60
cggttgtgag gtgctcacgt gttttggaga tagcaaaagt ctcaaataat atggcacaga   120
cg                                                                  122

<210> SEQ ID NO 141
<211> LENGTH: 122
<212> TYPE: DNA
<213> ORGANISM: Artificial Sequence
<220> FEATURE:
<223> OTHER INFORMATION: Forward Sequence

<400> SEQUENCE: 141
tcctaagcct ctctgagctg ggcttggcca ccttccgggg tgtgagcgtc cacgggagat    60
cgaccacacc aggcacccag gagcaagtgc tttgaaatgc ggctttctcc ggaccttgca   120
gg                                                                  122

<210> SEQ ID NO 142
<211> LENGTH: 122
<212> TYPE: DNA
<213> ORGANISM: Artificial Sequence
<220> FEATURE:
<223> OTHER INFORMATION: Forward Sequence

<400> SEQUENCE: 142
gagtcagtgc acagagttag aggcaggcag aaagaaagga gacctcccca acctcggccc    60
cgcccttccc tggcccaggc aacaaagcag cgaggagcca cgtgtggaaa agcagtgcag   120
at                                                                  122

<210> SEQ ID NO 143
<211> LENGTH: 122
<212> TYPE: DNA
<213> ORGANISM: Artificial Sequence
<220> FEATURE:
<223> OTHER INFORMATION: Forward Sequence

<400> SEQUENCE: 143
gcgcacacac gcacacaccc tcgggcgcct tggacggggt gcgctgggga gccagaagtt    60
cggagcgagc gcgggcgggc agagccgccg cctcggagcc cggagccggc ctgcaccccc   120
ct                                                                  122

<210> SEQ ID NO 144
<211> LENGTH: 122
<212> TYPE: DNA
<213> ORGANISM: Artificial Sequence
<220> FEATURE:
<223> OTHER INFORMATION: Forward Sequence
```

```
<400> SEQUENCE: 144
caccgggctc acactgctgc tcgcacggag cctgggcaca ggggtcctcg caactgcgcc    60
cgtctgctgc cagccggaag ccctcagtgc agcggcagga cacgtgacca tccacctcct   120
cc                                                                 122

<210> SEQ ID NO 145
<211> LENGTH: 122
<212> TYPE: DNA
<213> ORGANISM: Artificial Sequence
<220> FEATURE:
<223> OTHER INFORMATION: Forward Sequence

<400> SEQUENCE: 145
cctcgctaca ataacactcg aagccaccaa cgtagttgac acacatctgc tggcacacac    60
cggcaatctg gcactcatct gtgtccacac agcggtgcgg atcatcctcc gctggccgga   120
aa                                                                 122

<210> SEQ ID NO 146
<211> LENGTH: 122
<212> TYPE: DNA
<213> ORGANISM: Artificial Sequence
<220> FEATURE:
<223> OTHER INFORMATION: Forward Sequence

<400> SEQUENCE: 146
tagttgacac acatctgctg gcacacaccg gcaatctggc actcatctgt gtccacacag    60
cggtgcggat catcctccgc tggccggaaa cccaggcgac agtggcagct gtagccttgt   120
gg                                                                 122

<210> SEQ ID NO 147
<211> LENGTH: 121
<212> TYPE: DNA
<213> ORGANISM: Artificial Sequence
<220> FEATURE:
<223> OTHER INFORMATION: Forward Sequence

<400> SEQUENCE: 147
caaagccggc gaggaggcgg cggcgctggt gggactgacc cggcagtccg agaatccacc    60
gcggcctttt cacccaaccg ccccctcctg cgtgggggcc ccgcatcccc tggactggcg   120
t                                                                  121

<210> SEQ ID NO 148
<211> LENGTH: 122
<212> TYPE: DNA
<213> ORGANISM: Artificial Sequence
<220> FEATURE:
<223> OTHER INFORMATION: Forward Sequence

<400> SEQUENCE: 148
tcgacttaaa cccacgaagc tttggggagc actctagccc ctgctactca cccatgcaag    60
cggggtgcgc gctcgcgcac acactcactc actccaagat aggggctttc taggaaaata   120
ct                                                                 122

<210> SEQ ID NO 149
<211> LENGTH: 122
<212> TYPE: DNA
<213> ORGANISM: Artificial Sequence
<220> FEATURE:
<223> OTHER INFORMATION: Forward Sequence
```

```
<400> SEQUENCE: 149
ccggtgcgcc gggctctacc tcaaggagct cagggccatc gtgctgaacc aacagaggct    60
cgtccgcacc cagcgccaga gcatcgacga gctggagcgg cggctgaacg agctgagcgc   120
ct                                                                  122

<210> SEQ ID NO 150
<211> LENGTH: 122
<212> TYPE: DNA
<213> ORGANISM: Artificial Sequence
<220> FEATURE:
<223> OTHER INFORMATION: Forward Sequence

<400> SEQUENCE: 150
tgttacaatt taactacttt ctctttctct ttctctctct ctctctctct ctggtaaaaa    60
cgttaacctc tgctagtgat gaccaaacct ggtaaagatt gtaaagtggg aaaaattgga   120
tt                                                                  122

<210> SEQ ID NO 151
<211> LENGTH: 120
<212> TYPE: DNA
<213> ORGANISM: Artificial Sequence
<220> FEATURE:
<223> OTHER INFORMATION: Forward Sequence

<400> SEQUENCE: 151
ctcctcggcc ccctctggcc cccgtcctcc tttctctcct tccccctctc tctccaggag    60
cgactctggg ttagcaattg aactggattt acgagcgaga atgggtaatt acatccccca   120

<210> SEQ ID NO 152
<211> LENGTH: 122
<212> TYPE: DNA
<213> ORGANISM: Artificial Sequence
<220> FEATURE:
<223> OTHER INFORMATION: Forward Sequence

<400> SEQUENCE: 152
tctgcttaca gctgcttcca aattaagcat atctggatgg tgtgacactt tttgttagtc    60
cgagaactgt atgggcatcg caactgggcc tgttccaaga tagacttgtt gggaccttca   120
aa                                                                  122

<210> SEQ ID NO 153
<211> LENGTH: 122
<212> TYPE: DNA
<213> ORGANISM: Artificial Sequence
<220> FEATURE:
<223> OTHER INFORMATION: Forward Sequence

<400> SEQUENCE: 153
gtgaatggat ttggggaggg aggatcagac tagaggccag aagtccggtg agcaatatta    60
cagtagtcca ggtgagaggt aataatggcc tgcctaaccc agggaagcag ccacggggat   120
ta                                                                  122

<210> SEQ ID NO 154
<211> LENGTH: 122
<212> TYPE: DNA
<213> ORGANISM: Artificial Sequence
<220> FEATURE:
<223> OTHER INFORMATION: Forward Sequence
```

```
<400> SEQUENCE: 154
cacaccactc gtatctaact caacccctt agatattctt ccaggtggaa ttattggatt    60
cggtcagaat gggggagggg ccactatgcc cttaagaggc tcagaagtgc ctacctggct   120
aa                                                                 122

<210> SEQ ID NO 155
<211> LENGTH: 122
<212> TYPE: DNA
<213> ORGANISM: Artificial Sequence
<220> FEATURE:
<223> OTHER INFORMATION: Forward Sequence

<400> SEQUENCE: 155
ttcacctgac ccccatgctc ggccttctgg aagatgccca cagacactgg caataatgga    60
cgctggcaca ctctgccggc gcggccggag ccccggagtt cagcacctcg dacagagccc   120
ga                                                                  122

<210> SEQ ID NO 156
<211> LENGTH: 122
<212> TYPE: DNA
<213> ORGANISM: Artificial Sequence
<220> FEATURE:
<223> OTHER INFORMATION: Forward Sequence

<400> SEQUENCE: 156
cggcgcgcgc cgggctgtag ctctgcgacg acagcgagcg gttctgctgc gggtacgtgg    60
cgcacggccg cagcgccccc acggccggcg cgcacgcctc gtcccgcgcg cccgacgcct   120
gc                                                                  122

<210> SEQ ID NO 157
<211> LENGTH: 122
<212> TYPE: DNA
<213> ORGANISM: Artificial Sequence
<220> FEATURE:
<223> OTHER INFORMATION: Forward Sequence

<400> SEQUENCE: 157
cctgagctga ggacaaacta agaacagtgg tggacaacac tgggatggca aggatctggc    60
cgatgctgga ctatattgta ttttaaagtt ctaaattgtc tgggtgcagt ggctcacgcc   120
tg                                                                  122

<210> SEQ ID NO 158
<211> LENGTH: 122
<212> TYPE: DNA
<213> ORGANISM: Artificial Sequence
<220> FEATURE:
<223> OTHER INFORMATION: Forward Sequence

<400> SEQUENCE: 158
ggtgcgttgt tcgcgggggt gaattgtgaa gaaccatcgc ggggtccttc ctgctgaggc    60
cgcggacacc gtgacctcgc tgctctgggt ctgcaggaa acgtaggaaa aaagttgtc    120 ag                                                                  122

<210> SEQ ID NO 159
<211> LENGTH: 122
<212> TYPE: DNA
<213> ORGANISM: Artificial Sequence
<220> FEATURE:
<223> OTHER INFORMATION: Forward Sequence
```

<400> SEQUENCE: 159
actgtctctg cttcgagatc aagctccgat gaggacccag ggcccctgcc ctctggggag    60
cggccagccc ccagggccca tgtgccctcc tccctgaaga gcctttcccc acgccactgg   120
aa                                                                  122

<210> SEQ ID NO 160
<211> LENGTH: 122
<212> TYPE: DNA
<213> ORGANISM: Artificial Sequence
<220> FEATURE:
<223> OTHER INFORMATION: Forward Sequence

<400> SEQUENCE: 160
gctcctcatg tgagaaggac cataggaatc tcccgtttca caggtgggca caccaaggcc    60
cgacaatggg tccaggctgc caagggtgga gccgagatgc aaaggggcac ctcagagcct   120
gc                                                                  122

<210> SEQ ID NO 161
<211> LENGTH: 122
<212> TYPE: DNA
<213> ORGANISM: Artificial Sequence
<220> FEATURE:
<223> OTHER INFORMATION: Forward Sequence

<400> SEQUENCE: 161
ctcctggagt gggtgctcct gggatgcttc aggtttagac accggggtta cggcagctgc    60
cgaggaaggc taaagccagc gtcctggatt cagacagacc ttttagccat taaatccact   120
aa                                                                  122

<210> SEQ ID NO 162
<211> LENGTH: 121
<212> TYPE: DNA
<213> ORGANISM: Artificial Sequence
<220> FEATURE:
<223> OTHER INFORMATION: Forward Sequence

<400> SEQUENCE: 162
cagcctctca ggagctgaca ggtcctcttt cggggctcag gagggtgggc acacacccag    60
cggcctgcag agtaagctta ttacccacaa ctgtgcccgc tttgtgcttc taaggtgcac   120
a                                                                   121

<210> SEQ ID NO 163
<211> LENGTH: 122
<212> TYPE: DNA
<213> ORGANISM: Artificial Sequence
<220> FEATURE:
<223> OTHER INFORMATION: Forward Sequence

<400> SEQUENCE: 163
acccacctgc caggctgcgc ggggaggctg gtcccgggct gggcaggcgg gctggcctcg    60
cgccctcgag gcacccggcg gcgctggctg tgcggagggg cgccggcgcg gccgtatttg   120
ta                                                                  122

<210> SEQ ID NO 164
<211> LENGTH: 122
<212> TYPE: DNA
<213> ORGANISM: Artificial Sequence
<220> FEATURE:

<223> OTHER INFORMATION: Forward Sequence

<400> SEQUENCE: 164
ttggagctcg ccaaagccgc cccgggctct gtggtttcca gagcagatgc ggaggcggca    60
cgtcctcgtg cccttgctcc agctgcgcac acgacctcag cctcctctgc cccgctgggc   120
gc                                                                   122

<210> SEQ ID NO 165
<211> LENGTH: 122
<212> TYPE: DNA
<213> ORGANISM: Artificial Sequence
<220> FEATURE:
<223> OTHER INFORMATION: Forward Sequence

<400> SEQUENCE: 165
tccgtagtat tgtctctggc tttgaacgct gttgagggag gggaatgttt gcactcatcc    60
cgcatccttt tttggctgct atctttgcgg ggattgttca aggagaaatc catcctgact   120
gg                                                                   122

<210> SEQ ID NO 166
<211> LENGTH: 122
<212> TYPE: DNA
<213> ORGANISM: Artificial Sequence
<220> FEATURE:
<223> OTHER INFORMATION: Forward Sequence

<400> SEQUENCE: 166
accagcgcca ccgagaacac caggctccac atgaaggcgc gcagcagctt cagcgacagg    60
cgcgacggcg ccagcagcgc ggtcaccacc agctccggca tgtcgccgcg ctccgggacc   120
ac                                                                   122

<210> SEQ ID NO 167
<211> LENGTH: 122
<212> TYPE: DNA
<213> ORGANISM: Artificial Sequence
<220> FEATURE:
<223> OTHER INFORMATION: Forward Sequence

<400> SEQUENCE: 167
ttgcagcctg gagctcagct ccattggaat gctccgggcg ctgtccaagg tgctggaatg    60
cgccgcgccc gggggcagag ctgcgggccg ggggattatc gctgcccacg gcttcgggct   120
ga                                                                   122

<210> SEQ ID NO 168
<211> LENGTH: 122
<212> TYPE: DNA
<213> ORGANISM: Artificial Sequence
<220> FEATURE:
<223> OTHER INFORMATION: Forward Sequence

<400> SEQUENCE: 168
gccaggtcac cctctcactc tgtgcctctt agttatcttg catgctctgg tctttgcata    60
cgctgctccc tgcaccagga acctccatcc ccatctttgt ctgcttgtcg aacttcagaa   120
at                                                                   122

<210> SEQ ID NO 169
<211> LENGTH: 122
<212> TYPE: DNA
<213> ORGANISM: Artificial Sequence

```
<220> FEATURE:
<223> OTHER INFORMATION: Forward Sequence

<400> SEQUENCE: 169
agtatgtcag tggcaggtct ttctccttga gaccacagca gaccccagc cctgaggatg      60 cgaggcaggt gggttggatg agagggatct ggatgtctgg tctcaggctg ctcctctaag    120
gg                                                                  122

<210> SEQ ID NO 170
<211> LENGTH: 50
<212> TYPE: DNA
<213> ORGANISM: Artificial Sequence
<220> FEATURE:
<223> OTHER INFORMATION: Sourse Sequence

<400> SEQUENCE: 170
cggtctcccg aaccggtccc cgtaacgcga gcctgagatg ccctcacccc                50

<210> SEQ ID NO 171
<211> LENGTH: 50
<212> TYPE: DNA
<213> ORGANISM: Artificial Sequence
<220> FEATURE:
<223> OTHER INFORMATION: Source Sequence

<400> SEQUENCE: 171
ttcatctaga aggtttgact ctggccagac aaccagcgag catcttctcg                50

<210> SEQ ID NO 172
<211> LENGTH: 49
<212> TYPE: DNA
<213> ORGANISM: Artificial Sequence
<220> FEATURE:
<223> OTHER INFORMATION: Source Sequence

<400> SEQUENCE: 172
cgggactgcg gcaccttacg gcggaccaag atttgggtct gcgcaggcg                 49

<210> SEQ ID NO 173
<211> LENGTH: 50
<212> TYPE: DNA
<213> ORGANISM: Artificial Sequence
<220> FEATURE:
<223> OTHER INFORMATION: Source Sequence

<400> SEQUENCE: 173
cgtccgttac cactgacctg aggcctgcct gggtccaagc tcacacttgg                50

<210> SEQ ID NO 174
<211> LENGTH: 50
<212> TYPE: DNA
<213> ORGANISM: Artificial Sequence
<220> FEATURE:
<223> OTHER INFORMATION: Source Sequence

<400> SEQUENCE: 174
cgcccagttg acaagcattt tcttgtgtga tcctcgcagc agttctctgt                50

<210> SEQ ID NO 175
<211> LENGTH: 50
<212> TYPE: DNA
<213> ORGANISM: Artificial Sequence
<220> FEATURE:
<223> OTHER INFORMATION: Source Sequence
```

<400> SEQUENCE: 175
cgggcgatct cagtgcccca ggccaagatg ggcatcagca gttgttacca          50

<210> SEQ ID NO 176
<211> LENGTH: 50
<212> TYPE: DNA
<213> ORGANISM: Artificial Sequence
<220> FEATURE:
<223> OTHER INFORMATION: Source Sequence

<400> SEQUENCE: 176
caccgcgtgg agttgcttgt tcttttacat aggaggtcac attctcttcg          50

<210> SEQ ID NO 177
<211> LENGTH: 50
<212> TYPE: DNA
<213> ORGANISM: Artificial Sequence
<220> FEATURE:
<223> OTHER INFORMATION: Source Sequence

<400> SEQUENCE: 177
taggctttca gactggagcc cctggaatag gctcctcacc tagaggagcg          50

<210> SEQ ID NO 178
<211> LENGTH: 50
<212> TYPE: DNA
<213> ORGANISM: Artificial Sequence
<220> FEATURE:
<223> OTHER INFORMATION: Source Sequence

<400> SEQUENCE: 178
agggctcctt tcttcgtgcc ctccgggtct tgggagcaca gtagttatcg          50

<210> SEQ ID NO 179
<211> LENGTH: 50
<212> TYPE: DNA
<213> ORGANISM: Artificial Sequence
<220> FEATURE:
<223> OTHER INFORMATION: Source Sequence

<400> SEQUENCE: 179
cgtggcctgg ttaaccaatc tgttgcactg gctcccttt aaggggcctg           50

<210> SEQ ID NO 180
<211> LENGTH: 50
<212> TYPE: DNA
<213> ORGANISM: Artificial Sequence
<220> FEATURE:
<223> OTHER INFORMATION: Source Sequence

<400> SEQUENCE: 180
acgcgggaac tctttgagag agcggctcag cggcttggcc ttgccgtgcg          50

<210> SEQ ID NO 181
<211> LENGTH: 50
<212> TYPE: DNA
<213> ORGANISM: Artificial Sequence
<220> FEATURE:
<223> OTHER INFORMATION: Source Sequence

<400> SEQUENCE: 181
cttgggagca cagtagttat cgggagcgtc gcctccggcg tgggctctcg          50

<210> SEQ ID NO 182
<211> LENGTH: 50

```
<212> TYPE: DNA
<213> ORGANISM: Artificial Sequence
<220> FEATURE:
<223> OTHER INFORMATION: Source Sequence

<400> SEQUENCE: 182
tctcggggcc ttggcgactt accgctgggg gcccgcagtg cagcagggcg            50

<210> SEQ ID NO 183
<211> LENGTH: 50
<212> TYPE: DNA
<213> ORGANISM: Artificial Sequence
<220> FEATURE:
<223> OTHER INFORMATION: Source Sequence

<400> SEQUENCE: 183
cgcccgagag cccacgccgg aggcgacgct cccgataact actgtgctcc            50

<210> SEQ ID NO 184
<211> LENGTH: 50
<212> TYPE: DNA
<213> ORGANISM: Artificial Sequence
<220> FEATURE:
<223> OTHER INFORMATION: Source Sequence

<400> SEQUENCE: 184
catccatagg acttgctgat gatcacatgt ggcagaggaa gagccagtcc            50

<210> SEQ ID NO 185
<211> LENGTH: 50
<212> TYPE: DNA
<213> ORGANISM: Artificial Sequence
<220> FEATURE:
<223> OTHER INFORMATION: Source Sequence

<400> SEQUENCE: 185
gtttcagcac ctgggtcagc gcttcccagg gtcagcacca gggatagacg            50

<210> SEQ ID NO 186
<211> LENGTH: 50
<212> TYPE: DNA
<213> ORGANISM: Artificial Sequence
<220> FEATURE:
<223> OTHER INFORMATION: Source Sequence

<400> SEQUENCE: 186
cgccctggcc cagccccgat ccagcctgcg cctcacctcg ggttgtagac            50

<210> SEQ ID NO 187
<211> LENGTH: 50
<212> TYPE: DNA
<213> ORGANISM: Artificial Sequence
<220> FEATURE:
<223> OTHER INFORMATION: Source Sequence

<400> SEQUENCE: 187
cgggtcagat gttgccaacc tctgcagagt agcaataagc agtaaacgcc            50

<210> SEQ ID NO 188
<211> LENGTH: 50
<212> TYPE: DNA
<213> ORGANISM: Artificial Sequence
<220> FEATURE:
<223> OTHER INFORMATION: Source Sequence

<400> SEQUENCE: 188
```
cgccggtggc cgacggcttc tgaggaatta tcttttactt ggcgccacac    50

<210> SEQ ID NO 189
<211> LENGTH: 50
<212> TYPE: DNA
<213> ORGANISM: Artificial Sequence
<220> FEATURE:
<223> OTHER INFORMATION: Source Sequence

<400> SEQUENCE: 189
ggacccagaa aagcaccaaa actctttaga aggactgagc atcccttacg    50

<210> SEQ ID NO 190
<211> LENGTH: 50
<212> TYPE: DNA
<213> ORGANISM: Artificial Sequence
<220> FEATURE:
<223> OTHER INFORMATION: Source Sequence

<400> SEQUENCE: 190
gctgtcctca ggagccgcca gagtgctggg gaaggcggca gcaacgagcg    50

<210> SEQ ID NO 191
<211> LENGTH: 50
<212> TYPE: DNA
<213> ORGANISM: Artificial Sequence
<220> FEATURE:
<223> OTHER INFORMATION: Source Sequence

<400> SEQUENCE: 191
cgggtgacag ttacactaag agcccagatg ccaccacaat gcaatatacc    50

<210> SEQ ID NO 192
<211> LENGTH: 50
<212> TYPE: DNA
<213> ORGANISM: Artificial Sequence
<220> FEATURE:
<223> OTHER INFORMATION: Source Sequence

<400> SEQUENCE: 192
ggagcctggt tcacctattc acacacagag acatggctgc catagcaacg    50

<210> SEQ ID NO 193
<211> LENGTH: 50
<212> TYPE: DNA
<213> ORGANISM: Artificial Sequence
<220> FEATURE:
<223> OTHER INFORMATION: Source Sequence

<400> SEQUENCE: 193
gcagccacac atccaaggct gacagggcgg gcactctgcc aagtcctgcg    50

<210> SEQ ID NO 194
<211> LENGTH: 50
<212> TYPE: DNA
<213> ORGANISM: Artificial Sequence
<220> FEATURE:
<223> OTHER INFORMATION: Source Sequence

<400> SEQUENCE: 194
cggctgaggg gactccatta tctgtactct tcccggggtg ggtctaggtc    50

<210> SEQ ID NO 195
<211> LENGTH: 50
<212> TYPE: DNA
<213> ORGANISM: Artificial Sequence
<220> FEATURE:
<223> OTHER INFORMATION: Source Sequence

<400> SEQUENCE: 195
aagaaatacg gtgaaggagt ccttcccaaa gttgtctagg tccttccgcg    50

<210> SEQ ID NO 196
<211> LENGTH: 50
<212> TYPE: DNA
<213> ORGANISM: Artificial Sequence
<220> FEATURE:
<223> OTHER INFORMATION: Source Sequence

<400> SEQUENCE: 196
tgccagtcta gatccgtcct ggtgccttac tgtgcataca gttctactcg    50

<210> SEQ ID NO 197
<211> LENGTH: 50
<212> TYPE: DNA
<213> ORGANISM: Artificial Sequence
<220> FEATURE:
<223> OTHER INFORMATION: Source Sequence

<400> SEQUENCE: 197
cgacaaaatc tgaccaggct agatctgaat ctgttaattt ctgagacggt    50

<210> SEQ ID NO 198
<211> LENGTH: 50
<212> TYPE: DNA
<213> ORGANISM: Artificial Sequence
<220> FEATURE:
<223> OTHER INFORMATION: Source Sequence

<400> SEQUENCE: 198
cggcggctca acgtccacgg agccccagga atacccaccc gctgcccaga    50

<210> SEQ ID NO 199
<211> LENGTH: 50
<212> TYPE: DNA
<213> ORGANISM: Artificial Sequence
<220> FEATURE:
<223> OTHER INFORMATION: Source Sequence

<400> SEQUENCE: 199
cgagctgctc ccagtcaggt gaggaataaa atgctatgat ggcgtgaaaa    50

<210> SEQ ID NO 200
<211> LENGTH: 50
<212> TYPE: DNA
<213> ORGANISM: Artificial Sequence
<220> FEATURE:
<223> OTHER INFORMATION: Source Sequence

<400> SEQUENCE: 200
ctcgagtgca aggtgtgctt tgagaagttt ggccaccggc agcagcggcg    50

<210> SEQ ID NO 201
<211> LENGTH: 50
<212> TYPE: DNA
<213> ORGANISM: Artificial Sequence
<220> FEATURE:
<223> OTHER INFORMATION: Source Sequence

<400> SEQUENCE: 201
cgtatgtgtt tgagatagca gttgtttact atcacttgaa aattctgaat    50

<210> SEQ ID NO 202
<211> LENGTH: 50
<212> TYPE: DNA
<213> ORGANISM: Artificial Sequence
<220> FEATURE:
<223> OTHER INFORMATION: Source Sequence

<400> SEQUENCE: 202
cggccctcac tacacgaggc ctgggcgcct gcacgccccc gtgcttcagc                50

<210> SEQ ID NO 203
<211> LENGTH: 50
<212> TYPE: DNA
<213> ORGANISM: Artificial Sequence
<220> FEATURE:
<223> OTHER INFORMATION: Source Sequence

<400> SEQUENCE: 203
cgctctgtta ccattacctg gctcgccggc agaagaaaga acgcggagac                50

<210> SEQ ID NO 204
<211> LENGTH: 50
<212> TYPE: DNA
<213> ORGANISM: Artificial Sequence
<220> FEATURE:
<223> OTHER INFORMATION: Source Sequence

<400> SEQUENCE: 204
tgtttaacag cctcagaaat tatcttgtct ccgcgttctt tcttctgccg                50

<210> SEQ ID NO 205
<211> LENGTH: 50
<212> TYPE: DNA
<213> ORGANISM: Artificial Sequence
<220> FEATURE:
<223> OTHER INFORMATION: Source Sequence

<400> SEQUENCE: 205
cgcgctccgc cctttgcctg cagagcgctg ggggtttaaa gtcctgaacc                50

<210> SEQ ID NO 206
<211> LENGTH: 50
<212> TYPE: DNA
<213> ORGANISM: Artificial Sequence
<220> FEATURE:
<223> OTHER INFORMATION: Source Sequence

<400> SEQUENCE: 206
gccccccggc taagtcatgt ttaacagcct cagaaattat cttgtctccg                50

<210> SEQ ID NO 207
<211> LENGTH: 50
<212> TYPE: DNA
<213> ORGANISM: Artificial Sequence
<220> FEATURE:
<223> OTHER INFORMATION: Source Sequence

<400> SEQUENCE: 207
gtggcgcttg gcagcaggtg tgacagacct cctccggggc gcctgatccg                50

<210> SEQ ID NO 208
<211> LENGTH: 50
<212> TYPE: DNA
<213> ORGANISM: Artificial Sequence
<220> FEATURE:
<223> OTHER INFORMATION: Source Sequence

```
<400> SEQUENCE: 208
tcttctgccg gcgagccagg taatggtaac agagcgaaac tccccagtcg         50

<210> SEQ ID NO 209
<211> LENGTH: 50
<212> TYPE: DNA
<213> ORGANISM: Artificial Sequence
<220> FEATURE:
<223> OTHER INFORMATION: Source Sequence

<400> SEQUENCE: 209
cagccccatt taaggttttt gatacactga ggatcattca gaaaacttcg         50

<210> SEQ ID NO 210
<211> LENGTH: 50
<212> TYPE: DNA
<213> ORGANISM: Artificial Sequence
<220> FEATURE:
<223> OTHER INFORMATION: Source Sequence

<400> SEQUENCE: 210
caaagggctg atttctacag tcgctaggac ctgcagcggc gctgctcccg         50

<210> SEQ ID NO 211
<211> LENGTH: 50
<212> TYPE: DNA
<213> ORGANISM: Artificial Sequence
<220> FEATURE:
<223> OTHER INFORMATION: Source Sequence

<400> SEQUENCE: 211
cggttgtgag gtgctcacgt gttttggaga tagcaaaagt ctcaaataat         50

<210> SEQ ID NO 212
<211> LENGTH: 50
<212> TYPE: DNA
<213> ORGANISM: Artificial Sequence
<220> FEATURE:
<223> OTHER INFORMATION: Source Sequence

<400> SEQUENCE: 212
cgaccacacc aggcacccag gagcaagtgc tttgaaatgc ggctttctcc         50

<210> SEQ ID NO 213
<211> LENGTH: 50
<212> TYPE: DNA
<213> ORGANISM: Artificial Sequence
<220> FEATURE:
<223> OTHER INFORMATION: Source Sequence

<400> SEQUENCE: 213
tttccacacg tggctcctcg ctgctttgtt gcctgggcca gggaagggcg         50

<210> SEQ ID NO 214
<211> LENGTH: 50
<212> TYPE: DNA
<213> ORGANISM: Artificial Sequence
<220> FEATURE:
<223> OTHER INFORMATION: Source Sequence

<400> SEQUENCE: 214
acacaccctc gggcgccttg gacggggtgc gctggggagc cagaagttcg         50

<210> SEQ ID NO 215
```

<211> LENGTH: 50
<212> TYPE: DNA
<213> ORGANISM: Artificial Sequence
<220> FEATURE:
<223> OTHER INFORMATION: Source Sequence

<400> SEQUENCE: 215
tggtcacgtg tcctgccgct gcactgaggg cttccggctg gcagcagacg                    50

<210> SEQ ID NO 216
<211> LENGTH: 50
<212> TYPE: DNA
<213> ORGANISM: Artificial Sequence
<220> FEATURE:
<223> OTHER INFORMATION: Source Sequence

<400> SEQUENCE: 216
cggcaatctg gcactcatct gtgtccacac agcggtgcgg atcatcctcc                    50

<210> SEQ ID NO 217
<211> LENGTH: 50
<212> TYPE: DNA
<213> ORGANISM: Artificial Sequence
<220> FEATURE:
<223> OTHER INFORMATION: Source Sequence

<400> SEQUENCE: 217
atctgctggc acacaccggc aatctggcac tcatctgtgt ccacacagcg                    50

<210> SEQ ID NO 218
<211> LENGTH: 50
<212> TYPE: DNA
<213> ORGANISM: Artificial Sequence
<220> FEATURE:
<223> OTHER INFORMATION: Source Sequence

<400> SEQUENCE: 218
ggaggcggcg gcgctggtgg ggactgaccc ggcagtccga gaatccaccg                    50

<210> SEQ ID NO 219
<211> LENGTH: 50
<212> TYPE: DNA
<213> ORGANISM: Artificial Sequence
<220> FEATURE:
<223> OTHER INFORMATION: Source Sequence

<400> SEQUENCE: 219
cacgaagctt tggggagcac tctagcccct gctactcacc catgcaagcg                    50

<210> SEQ ID NO 220
<211> LENGTH: 50
<212> TYPE: DNA
<213> ORGANISM: Artificial Sequence
<220> FEATURE:
<223> OTHER INFORMATION: Source Sequence

<400> SEQUENCE: 220
gctctacctc aaggagctca gggccatcgt gctgaaccaa cagaggctcg                    50

<210> SEQ ID NO 221
<211> LENGTH: 50
<212> TYPE: DNA
<213> ORGANISM: Artificial Sequence
<220> FEATURE:
<223> OTHER INFORMATION: Source Sequence

<400> SEQUENCE: 221
cgttaacctc tgctagtgat gaccaaacct ggtaaagatt gtaaagtggg          50

<210> SEQ ID NO 222
<211> LENGTH: 50
<212> TYPE: DNA
<213> ORGANISM: Artificial Sequence
<220> FEATURE:
<223> OTHER INFORMATION: Source Sequence

<400> SEQUENCE: 222
ttacccattc tcgctcgtaa atccagttca attgtgctaa cccagagtcg          50

<210> SEQ ID NO 223
<211> LENGTH: 50
<212> TYPE: DNA
<213> ORGANISM: Artificial Sequence
<220> FEATURE:
<223> OTHER INFORMATION: Source Sequence

<400> SEQUENCE: 223
aacaagtcta tcttggaaca ggcccagttg cgatgcccat acagttctcg          50

<210> SEQ ID NO 224
<211> LENGTH: 50
<212> TYPE: DNA
<213> ORGANISM: Artificial Sequence
<220> FEATURE:
<223> OTHER INFORMATION: Source Sequence

<400> SEQUENCE: 224
cagtagtcca ggtgagaggt aataatggcc tgcctaaccc agggaagcag          50

<210> SEQ ID NO 225
<211> LENGTH: 50
<212> TYPE: DNA
<213> ORGANISM: Artificial Sequence
<220> FEATURE:
<223> OTHER INFORMATION: Source Sequence

<400> SEQUENCE: 225
atctaactca accccttag atattcttcc aggtggaatt attggattcg          50

<210> SEQ ID NO 226
<211> LENGTH: 50
<212> TYPE: DNA
<213> ORGANISM: Artificial Sequence
<220> FEATURE:
<223> OTHER INFORMATION: Source Sequence

<400> SEQUENCE: 226
ccatgctcgg ccttctggaa gatgcccaca gacactggca ataatggacg          50

<210> SEQ ID NO 227
<211> LENGTH: 50
<212> TYPE: DNA
<213> ORGANISM: Artificial Sequence
<220> FEATURE:
<223> OTHER INFORMATION: Source Sequence

<400> SEQUENCE: 227
cgccacgtac ccgcagcaga accgctcgct gtcgtcgcag agctacagcc          50

<210> SEQ ID NO 228
<211> LENGTH: 50
<212> TYPE: DNA

<213> ORGANISM: Artificial Sequence
<220> FEATURE:
<223> OTHER INFORMATION: Source Sequence

<400> SEQUENCE: 228
actgcaccca gacaatttag aactttaaaa tacaatatag tccagcatcg        50

<210> SEQ ID NO 229
<211> LENGTH: 50
<212> TYPE: DNA
<213> ORGANISM: Artificial Sequence
<220> FEATURE:
<223> OTHER INFORMATION: Source Sequence

<400> SEQUENCE: 229 gcggggtga attgtgaaga accatcgcgg ggtccttcct gctgaggccg        50

<210> SEQ ID NO 230
<211> LENGTH: 50
<212> TYPE: DNA
<213> ORGANISM: Artificial Sequence
<220> FEATURE:
<223> OTHER INFORMATION: Source Sequence

<400> SEQUENCE: 230
tcgagatcaa gctccgatga ggacccaggg cccctgccct ctggggagcg        50

<210> SEQ ID NO 231
<211> LENGTH: 50
<212> TYPE: DNA
<213> ORGANISM: Artificial Sequence
<220> FEATURE:
<223> OTHER INFORMATION: Source Sequence

<400> SEQUENCE: 231
cgggccttgg tgtgcccacc tgtgaaacgg gagattccta tggtccttct        50

<210> SEQ ID NO 232
<211> LENGTH: 50
<212> TYPE: DNA
<213> ORGANISM: Artificial Sequence
<220> FEATURE:
<223> OTHER INFORMATION: Source Sequence

<400> SEQUENCE: 232
atggctaaaa ggtctgtctg aatccaggac gctggcttta gccttcctcg        50

<210> SEQ ID NO 233
<211> LENGTH: 50
<212> TYPE: DNA
<213> ORGANISM: Artificial Sequence
<220> FEATURE:
<223> OTHER INFORMATION: Source Sequence

<400> SEQUENCE: 233
cggcctgcag agtaagctta ttacccacaa ctgtgcccgc tttgtgcttc        50

<210> SEQ ID NO 234
<211> LENGTH: 50
<212> TYPE: DNA
<213> ORGANISM: Artificial Sequence
<220> FEATURE:
<223> OTHER INFORMATION: Source Sequence

<400> SEQUENCE: 234
ggctgcgcgg ggaggctggt cccgggctgg gcaggcgggc tggcctcgcg        50

<210> SEQ ID NO 235
<211> LENGTH: 50
<212> TYPE: DNA
<213> ORGANISM: Artificial Sequence
<220> FEATURE:
<223> OTHER INFORMATION: Source Sequence

<400> SEQUENCE: 235
cgtgccgcct ccgcatctgc tctggaaacc acagagcccg gggcggcttt        50

<210> SEQ ID NO 236
<211> LENGTH: 50
<212> TYPE: DNA
<213> ORGANISM: Artificial Sequence
<220> FEATURE:
<223> OTHER INFORMATION: Source Sequence

<400> SEQUENCE: 236
gatttctcct tgaacaatcc ccgcaaagat agcagccaaa aaaggatgcg        50

<210> SEQ ID NO 237
<211> LENGTH: 50
<212> TYPE: DNA
<213> ORGANISM: Artificial Sequence
<220> FEATURE:
<223> OTHER INFORMATION: Source Sequence

<400> SEQUENCE: 237
gagaacacca ggctccacat gaaggcgcgc agcagcttca gcgacaggcg        50

<210> SEQ ID NO 238
<211> LENGTH: 50
<212> TYPE: DNA
<213> ORGANISM: Artificial Sequence
<220> FEATURE:
<223> OTHER INFORMATION: Source Sequence

<400> SEQUENCE: 238
gctcagctcc attggaatgc tccgggcgct gtccaaggtg ctggaatgcg        50

<210> SEQ ID NO 239
<211> LENGTH: 50
<212> TYPE: DNA
<213> ORGANISM: Artificial Sequence
<220> FEATURE:
<223> OTHER INFORMATION: Source Sequence

<400> SEQUENCE: 239
tctcactctg tgcctcttag ttatcttgca tgctctggtc tttgcatacg        50

<210> SEQ ID NO 240
<211> LENGTH: 50
<212> TYPE: DNA
<213> ORGANISM: Artificial Sequence
<220> FEATURE:
<223> OTHER INFORMATION: Source Sequence

<400> SEQUENCE: 240
cgcatcctca gggctggggg tctgctgtgg tctcaaggag aaagacctgc        50

METHODS FOR PREDICTING AGE AND IDENTIFYING AGENTS THAT INDUCE OR INHIBIT PREMATURE AGING

This invention was made with Government support under P50GM085764, ES014811, EY014428, EY018660, EY019270 and EY021374 awarded by the NIH. The Government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

Not everyone ages in the same manner. It is well known that women tend to live longer than men, and lifestyle choices such as smoking and physical fitness can hasten or delay the aging process (Steven N., 2006; Blair et al., 1989). These observations have led to the search for molecular markers of age which can be used to predict, monitor, and provide insight into age-associated physiological decline and disease. One such marker is telomere length, a molecular trait strongly correlated with age (Harley et al., 1990) which has been shown to have an accelerated rate of decay under environmental stress (Epel et al., 2004; Valdes et al.). Another marker is gene expression, especially for genes that function in metabolic and DNA repair pathways which are predictive of age across a range of different tissue types and organisms (Fraser et al., 2005; Zahn et al., 2007; de Magalhães et al., 2009).

A growing body of research has reported associations between age and the state of the epigenome—the set of modifications to DNA other than changes in the primary nucleotide sequence (Fraga and Esteller, 2007). In particular, DNA methylation associates with chronological age over long time scales (Alisch et al., 2012; Christensen et al., 2009; Bollati et al., 2009; Boks et al., 2009; Rakyan et al., 2010; Bocklandt et al., 2011; Bell et al., 2012) and changes in methylation have been linked to complex age-associated diseases such as metabolic disease (Barres and Zierath, 2011) and cancer (Jones and Laird, 1999; Esteller, 2008). Studies have also observed a phenomenon dubbed "epigenetic drift", whereby the DNA methylation marks in identical twins increasingly differ as a function of age (Fraga et al., 2005; Boks et al., 2009). Thus, the idea of the epigenome as a fixed imprint is giving way to the model of the epigenome as a dynamic landscape that reflects a variety of chronological changes. The current challenge is to determine whether these changes can be systematically described and modeled to detect different rates of human aging, and to tie these rates to related clinical or environmental variables.

The mechanisms that drive changes in the aging methylome are not well understood, although they have been attributed to at least two underlying factors (Vijg and Campisi, 2008; Fraga et al., 2005). First, it is possible that environmental exposure will over time activate cellular programs associated with consistent and predictable changes in the epigenome. For example, stress has been shown to alter gene expression patterns through specific changes in DNA methylation (Murgatroyd et al., 2009). Alternatively, spontaneous epigenetic changes may occur with or without environmental stress, leading to fundamentally unpredictable differences in the epigenome between aging individuals. Spontaneous changes may be caused by chemical agents that disrupt DNA methyl groups or through errors in copying methylation states during DNA replication. Both mechanisms lead to differences between the methylomes of aging individuals, suggesting that quantitative measurements of methylome states may identify factors involved with slowed or accelerated rates of aging.

To better understand how the methylome ages and to determine whether human aging rates can be quantified and compared, we initiated a project to perform genome-wide methylomic profiling of a large cohort of individuals spanning a wide age range. Based on these findings, we constructed a predictive model of aging rate which we show is influenced by gender and specific genetic variants. These data help explain epigenetic drift and suggest that age-associated changes in the methylome lead to changes in transcriptional patterns over time. These findings were replicated in a second large cohort.

The ability to measure human aging from molecular profiles has practical implications in many fields, including disease prevention and treatment, forensics, and extension of life. Although chronological age has been linked to changes in DNA methylation, the methylome has not yet been used to measure and compare human aging rates. Here, we have created a quantitative model of aging using measurements at more than 450,000 CpG markers from the whole blood of 656 human individuals, aged 19 to 101. This model measures the rate at which an individual's methylome ages. Furthermore, we have discovered that differences in aging rates may explain epigenetic drift and are reflected in the transcriptome. Our discovery highlights specific components of the aging process and provides forensic methods, screening methods for agents retarding or accelerating aging, and methods for preventing and treating diseases.

SUMMARY OF THE INVENTION

The invention provides methods for predicting age of a subject based on the epigenome of the subject. In one embodiment, the method comprises (a) obtaining a biological sample of the subject; (b) determining the methylation status of a set of age-associated epigenetic marker(s) in the epigenome of the subject as shown in any of FIG. 9, Tables 3, 4 and/or 5; and (c) comparing the methylation status of a set of age-associated epigenetic marker(s) of the subject with the methylation status of the same markers from an age correlated reference population so as to obtain a value or a range of values for the predicted age of the subject thereby predicting the age of a subject based on the epigenome of the subject.

The invention also provides for methods for identifying type of tissue for a biological sample from a subject with a known chronological age. In one embodiment, the method comprises (a) ascertaining the chronological age of a subject; (b) determining the AMAR of the subject from the biological sample by dividing the predicted age of a subject from the chronological age of the subject; (c) comparing to a reference standard relating AMAR to chronological age for various types of tissue; (d) determining which value from step (b) closely matches the AMAR in the reference standard for various types of tissue from step (c); and (e) based on the closest match in step (d), assigning the type of tissue for the biological sample, thereby identifying type of tissue for a biological sample from a subject with a known chronological age.

The invention further provides for methods for predicting age of a subject based on age-associated epigenetic modification affecting gene expression comprising: (a) obtaining a biological sample of the subject; (b) determining the expression of one or more gene(s) associated with age-associated epigenetic marker(s) whose expression changes with age; (c) comparing the expression of one or more gene(s) associated with age-associated epigenetic marker(s) whose expression changes with age with the expression of the same gene(s) from an age correlated reference population; and (d) obtaining a value or range of values for the predicted age of the subject; wherein comparing the expression of one or more gene(s) associated with age-associated epigenetic marker(s) whose expression changes with age with the expression of the same gene(s) from an age correlated reference population comprises any statistical method, multivariate regression method, linear regression analysis, tabular method, or graphical method used to predict the age of a subject based on expression of gene(s) associated with age-associated epigenetic marker(s) whose expression changes with age; thereby predicting age of a subject based on age-associated epigenetic modification affecting gene expression.

The invention also provides methods for predicting age of a tissue or organ of a subject based on the epigenome of the tissue or organ of the subject. In one embodiment, the method comprises (a) obtaining a biological sample of a tissue or organ from the subject; (b) determining the methylation status of a set of age-associated epigenetic marker(s) in the epigenome of the subject selected from FIG. 9, Tables 3, 4 and/or 5; and (c) comparing the methylation status of the set of age-associated epigenetic marker(s) of the subject with the methylation status of the same markers from an age-correlated reference population so as to obtain a value or a range of values for the predicted age of the tissue or organ, thereby predicting the age of a tissue or organ of a subject based on the epigenome of the tissue or organ of the subject.

The invention also provides for a kit for determining age of a subject based on epigenetic modification of subject's genetic material comprising any age-associated epigenetic marker or markers as listed in FIG. 9, Table 3, Table 4 or Table 5.

The invention further provides for a kit for predicting age of a subject based on the epigenome of the subject utilizing the set of the age-associated epigenetic marker(s) provided in FIG. 9, Table 3, 4 and/or 5.

BRIEF DESCRIPTION OF THE FIGURES

FIG. 9 is a collection of FIG. 9A (9A through 9A-7), 9B (9B through 9B-7), 9C (9C through 9C-7), 9D (9D through 9D-7) and 9E (9E through 9E-7) which are spreadsheets showing age-associated epigenetic markers, designated by "cg" prefix followed by a number (cg#), related to Table 3 in which each of the CpG dinucleotide so examined is embedded within the sequence shown in column entitled "Forward_Sequence" in the third subpanel of each series (i.e., FIGS. 9x-2, where "x" is A-E). For example, the dinucleotide of interest is bounded by brackets. Additional information may be found in the Gene Expression Omnibus (GEO) database with GEO accession number GPL13534 and Bibikova et al. Genomics, 2011, 98:288-95. The various subpanels of the spreadsheets should be assembled as shown below:

| 9A | 9A-1 | 9A-2 | 9A-3 | 9A-4 | 9A-5 | 9A-6 | 9A-7 |
|----|------|------|------|------|------|------|------|
| 9B | 9B-1 | 9B-2 | 9B-3 | 9B-4 | 9B-5 | 9B-6 | 9B-7 |
| 9C | 9C-1 | 9C-2 | 9C-3 | 9C-4 | 9C-5 | 9C-6 | 9C-7 |
| 9D | 9D-1 | 9D-2 | 9D-3 | 9D-4 | 9D-5 | 9D-6 | 9D-7 |
| 9E | 9E-1 | 9E-2 | 9E-3 | 9E-4 | 9E-5 | 9E-6 | 9E-7 |

Figure 10:
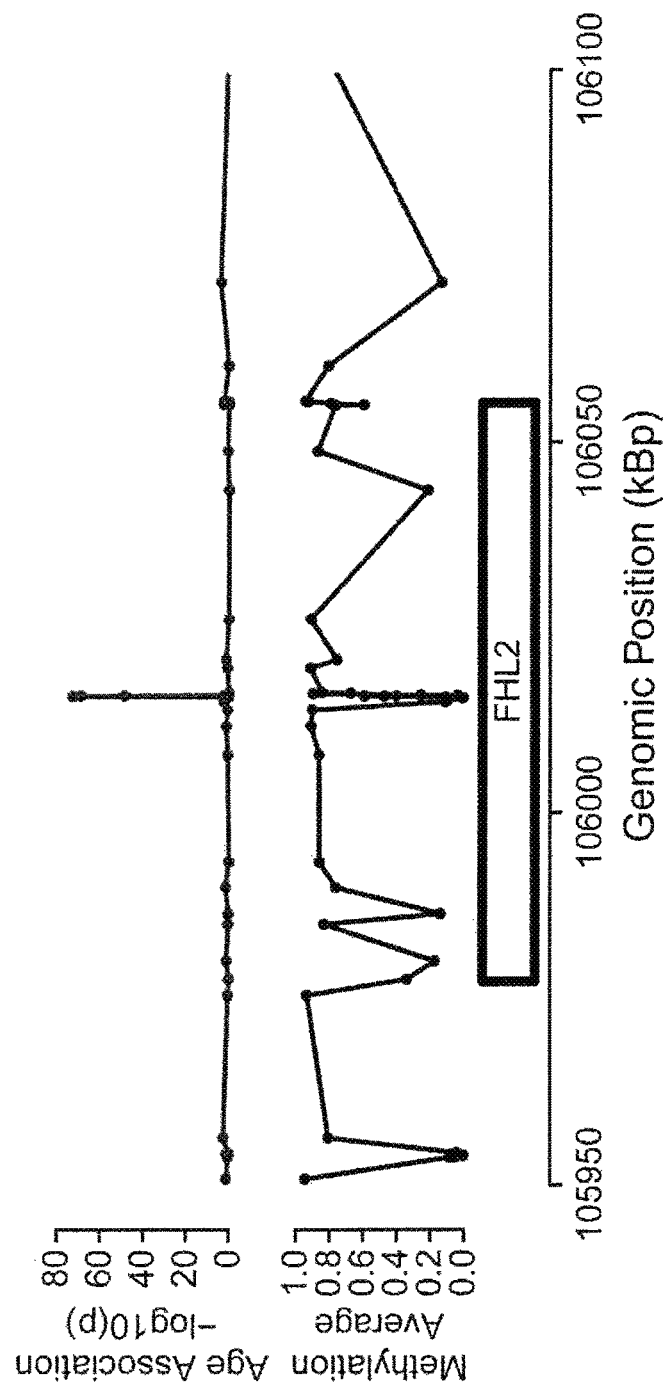

FIG. 10. An example aging association map, related to FIG. 1

Age association levels for the gene Four and a Half LIM Domains 2 (FHL2). A strong aging association is shown for several markers (red: $-\log_{10}$(p-value)) at a CpG island in the center of the gene, coincident with an internal promoter (black: average methylation fraction).

Figure 11:
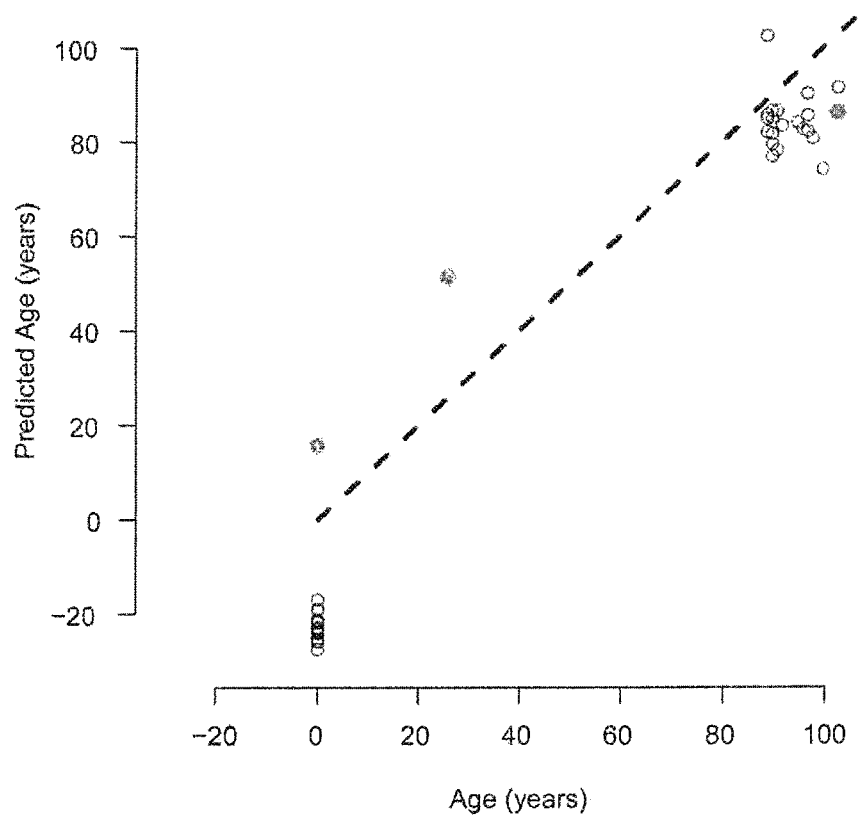

FIG. 11. Apply the aging model to the Heyn et al. dataset, related to FIG. 2

We obtained methylation profiles from the Heyn et al. dataset and applied the age prediction model. Our model successfully separated old and young samples (black circles). In addition, we applied the aging model to the three samples in the Heyn et al. dataset which were measured using bisulfite sequencing rather than the bead-chip technology used for our data. Despite the differences in technology, the model successfully separated the young, middle-aged, and old samples (green dots).

Figure 12:
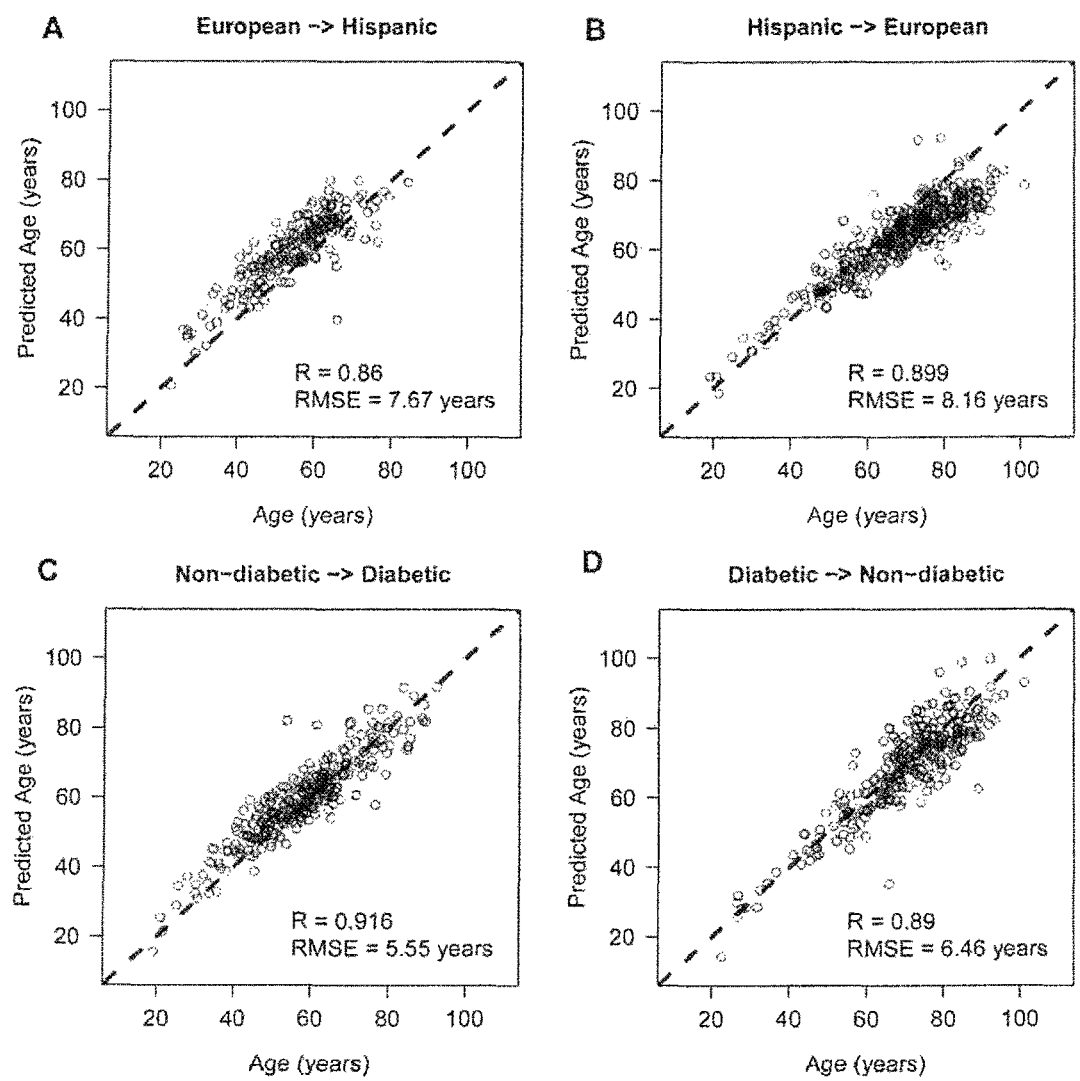

FIG. 12. Measuring the effects of batch-correlated variables, related to FIG. 2

The model covariates of ethnicity and diabetes status were highly correlated with batch variables, such that their effect on the aging process could not be determined. Nonetheless, we built separate models for the subgroups (A) European, (B) Hispanic, (C) Non-diabetic, and (D) Diabetic. Each model was used to predict the age of its complementary cohort. The results show a strong predictive power despite the covariate and/or batch effects.

Figure 13:
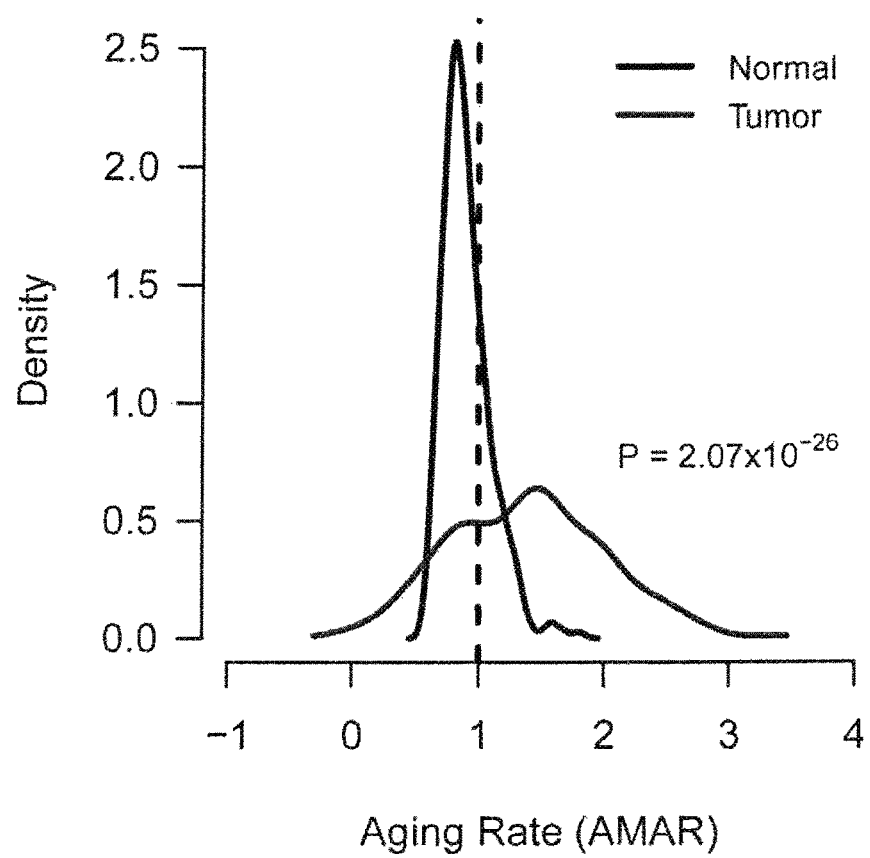

FIG. 13. Normal and tumor aging model predictions, related to FIG. 4

Aging models were built in matched normal and tumor samples using the model markers identified in the primary cohort. The aging rate (AMAR) of tumor samples predicted by normal tissue was found to be higher than expected (red, Wilcox test, $P<10^{-21}$) and the aging rate of normal samples predicted by the tumor model was lower than expected (black, Wilcox test, $P<10^{-17}$). The separation of the two aging rates was also highly significant (Wilcox test, $P<10^{-25}$).

Figure 14:
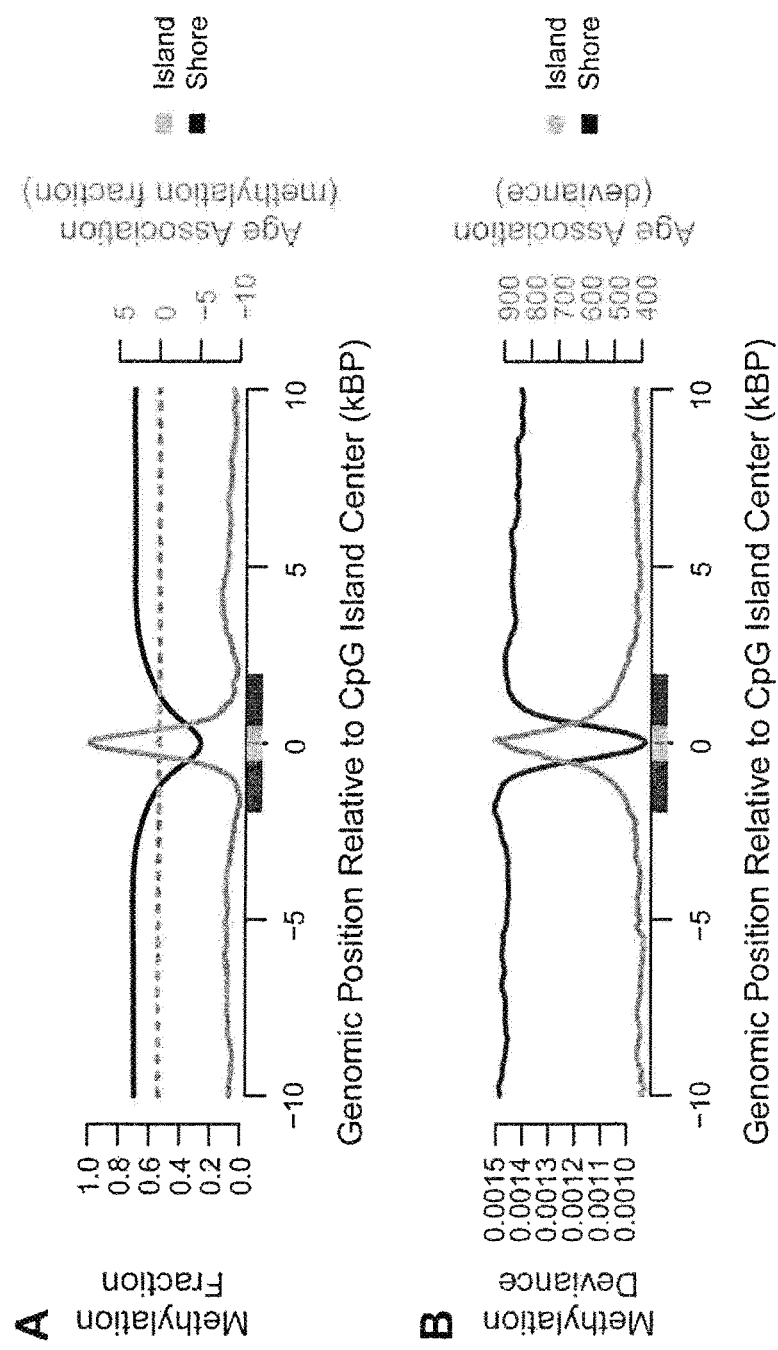

FIG. 14. A map of aging trends in CpG Islands, related to FIG. 5

(A) An aggregate genomic map of the methylation fraction for 27,176 CpG islands (black). The aging coefficient relating methylation fraction to age is shown in the same region (green). Color bars indicating the island and shore regions represent 75% confidence intervals. (B) A CpG island map showing methylation deviance (red) and the aging coefficient for deviance (green).

DETAILED DESCRIPTION OF THE FIGURES

Definitions

As used in this application, the biological age (bioage), chemical age, methylomic age and molecular age are equivalent or synonymous. The biological age is determined using a set of age-associated epigenetic markers of a subject or an organism. In the current invention, the biological age is determined from an analysis of the modification status of specific CpG dinucleotide and, in particular, e.g., the methylation status at the C-5 position of cytosine.

Chronological age is the actual age of a subject or organism. For animals and humans, chronological age may be based on the age calculated from the moment of conception or based on the age calculated from the time and date of birth. The chronological age of the cell, tissue or organ may be determined from the chronological age of the subject or organism from which the cell, tissue or organ is obtained, plus the duration of the cell, tissue or organ is placed in culture. Alternatively, in the case of the cell or tissue culture, the chronological age may be related to the total or accumulative time in culture or passage number.

As used in this application, the term "tissue" may be replaced with "cell," or vice versa, for a biological sample.

The methylation marker as provided in Tables 3, 4 and 5 under the column "Marker" or "Methylation Marker," provided in FIG. 9 under the column "ID" or "Name" in FIG. 9x where "x" is A-E and discussed in the text with a "cg#" designation are age-associated epigenetic markers. The specific CpG dinucleotide within each epigenetic marker probed in the invention is provided in FIG. 9 under the heading "Forward_Sequence" and the specific CpG dinucleotide probed within brackets, i.e., [CG]. Additional sequence information for all "cg#" designation, such as in Tables 4 and 5 and in the text, may be obtained at the National Center for Biotechnology Information of the National Institutes of Health (Bethesda, Md.) in the Gene Expression Omnibus (GEO) database with GEO accession number GPL13534.

The methylation markers as provided in FIG. 9, Tables 3, 4 and 5 were used in an Illumina's Infinium Methylation Assay using the HumanMethylation450 BeadChip. However, these age-associated epigenetic markers may be used in other assays outside of the Infinium Methylation Assay system, based on the sequence, homology, or normal association to sequence for each cg# provided in the invention.

Methods of the Invention

The invention provides for methods for predicting age of a subject based on the epigenome of the subject. The subject may be human, mammal, animal, plant, or any multicellular organism. Examples of suitable mammals include but are not limited human, monkey, ape, dog, cat, cow, horse, goat, pig, rabbit, mouse and rat. The age of a subject may be a chronological age or a molecular age, chemical age, methylomic age or biological age. The epigenome may be deoxyribonucleic acid (DNA) in which the DNA may be subjected to epigenetic modification. The epigenetic modification may be methylation of CpG residues. In one embodiment, the methylation is the covalent attachment of a methyl group at the carbon-5 (C-5) position of cytosine.

In one embodiment, the method comprises obtaining a biological sample of the subject. Additionally, the method comprises determining the methylation status of a set of age-associated epigenetic marker(s) in the epigenome of the subject selected from FIG. 9, Tables 3, 4 and/or 5. Further, the method comprises comparing the methylation status of a set of age-associated epigenetic marker(s) of the subject with the methylation status of the same markers from an age correlated reference population so as to obtain a value or a range of values for the predicted age of the subject, thereby predicting the age of a subject based on the epigenome of the subject.

In one embodiment, the method comprises use of a statistical method to compare the methylation status of a set of age-associated epigenetic marker(s) of the subject with the methylation status of the same markers from an age correlated reference population. Examples of suitable statistical methods include but are not limited to multivariate regression method, linear regression analysis, tabular method or graphical method comprises Elastic Net, Lasso regression method, ridge regression method, least-squares fit, binomial test, Shapiro-Wilk test, Grubb's statistics, Benjamini-Hochberg FDR, variance analysis, entropy statistics, and/or Shannon entropy. In a preferred embodiment, the statistical method comprises a multivariate regression algorithm or linear regression algorithm.

In accordance with the practice of the invention, determining the methylation status may comprise isolating genomic DNA or nuclear DNA from the sample, reacting the isolated genomic DNA or nuclear DNA with one or more probe/agent (e.g., a chemical probe/agent) which differentially reacts with unmodified cytosine so that the cytosine is converted to uracil. The step may also comprise determining or analyzing the methylation status at the cytosine position (also referred to herein as the C position) of a CpG dinucleotide in the isolated genomic DNA or nuclear DNA of the sample by detecting the presence of a cytosine or uracil. The presence of cytosine or uracil indicates the presence of a 5-methylcytosine or unmodified cytosine, respectively, in the original CpG dinucleotide. Alternatively, resistance to cleavage by a restriction enzyme may indicate the presence of 5-methylcytosine at the original CpG dinucleotide. Sensitivity to cleavage by the restriction enzyme may indicate presence of unmodified cytosine at the original CpG dinucleotide. Further, the step may further comprise determining the proportion of 5-methylcytosine or unmodified cytosine initially present at each age-associated epigenetic marker; or alternatively, determining the ratio of 5-methylcytosine to unmodified cytosine or the ratio of unmodified cytosine to 5-methyl-cytosine cytosine initially present at each age-associated epigenetic marker based on characterizing outcome of probing the isolated genomic DNA or nuclear DNA.

In accordance with the practice of the invention, determining the methylation status may comprise isolating genomic DNA or nuclear DNA from the sample, incubating the isolated genomic DNA or nuclear DNA with one or more restriction enzyme which recognizes a specific DNA sequence, is affected by a CpG dinucleotide, within or adjacent to the restriction enzyme recognition or cleavage site, and differentially cleaves the DNA based on the presence or absence of a methyl group at C-5 position of cytosine of the CpG dinucleotide. The step may also comprise determining or analyzing the methylation status at the C position of a CpG dinucleotide in the isolated genomic DNA or nuclear DNA of the sample by its resistance to cleavage at a potential cleavage site by the restriction enzyme indicating presence of 5-methylcytosine at the original CpG dinucleotide within or adjacent to the restriction enzyme recognition or cleavage site. Sensitivity to cleavage by the restriction enzyme may indicate presence of unmodified cytosine. Further, the step may further comprise determining the proportion of 5-methylcytosine or unmodified cytosine initially present at each age-associated epigenetic marker; or alternatively, determining the ratio of 5-methylcytosine to unmodified cytosine or the ratio of unmodified cytosine to 5-methylcytosine initially present at each age-associated epigenetic marker.

In accordance with the practice of the invention, the methylation status may be determined based on five or more age-associated epigenetic marker(s) in the epigenome of the subject selected from FIG. 9, Tables 3, 4 and/or 5; ten or more age-associated epigenetic marker(s) in the epigenome of the subject selected from FIG. 9, Tables 3, 4 and/or 5; fifteen or more age-associated epigenetic marker(s) in the epigenome of the subject selected from FIG. 9, Tables 3, 4 and/or 5; twenty or more age-associated epigenetic marker(s) in the epigenome of the subject selected from FIG. 9, Tables 3, 4 and/or 5; twenty-five or more age-associated epigenetic marker(s) in the epigenome of the subject selected from FIG. 9, Tables 3, 4 and/or 5; thirty or more age-associated epigenetic marker(s) in the epigenome of the subject selected from FIG. 9, Tables 3, 4 and/or 5; thirty-five or more age-associated epigenetic marker(s) in the epigenome of the subject selected from FIG. 9, Tables 3, 4 and/or 5; forty or more age-associated epigenetic marker(s) in the epigenome of the subject selected from FIG. 9, Tables 3, 4 and/or 5; forty-five or more age-associated epigenetic marker(s) in the epigenome of the subject selected from FIG. 9, Tables 3, 4 and/or 5; fifty or more age-associated epigenetic marker(s) in the epigenome of the subject selected from FIG. 9, Tables 3, 4 and/or 5; fifty-five or more age-associated epigenetic marker(s) in the epigenome of the subject selected from FIG. 9, Tables 3, 4 and/or 5; sixty or more age-associated epigenetic marker(s) in the epigenome of the subject selected from FIG. 9, Tables 3, 4 and/or 5; sixty-five or more age-associated epigenetic marker(s) in the epigenome of the subject selected from FIG. 9, Tables 3, 4 and/or 5; or seventy or more age-associated epigenetic marker(s) in the epigenome of the subject selected from FIG. 9, Tables 3, 4 and/or 5.

Further, in a preferred embodiment, the methylation status may be determined based on five or more age-associated epigenetic marker(s) in the epigenome of the subject from FIG. 9 or Table 3; ten or more age-associated epigenetic marker(s) in the epigenome of the subject from FIG. 9 or Table 3; fifteen or more age-associated epigenetic marker(s) in the epigenome of the subject from FIG. 9 or Table 3; twenty or more age-associated epigenetic marker(s) in the epigenome of the subject from FIG. 9 or Table 3; twenty-five or more age-associated epigenetic marker(s) in the epigenome of the subject from FIG. 9 or Table 3; thirty or more age-associated epigenetic marker(s) in the epigenome of the subject from FIG. 9 or Table 3; thirty-five or more age-associated epigenetic marker(s) in the epigenome of the subject from FIG. 9 or Table 3; forty or more age-associated epigenetic marker(s) in the epigenome of the subject from FIG. 9 or Table 3; forty-five or more age-associated epigenetic marker(s) in the epigenome of the subject from FIG. 9 or Table 3; fifty or more age-associated epigenetic marker(s) in the epigenome of the subject from FIG. 9 or Table 3; fifty-five or more age-associated epigenetic marker(s) in the epigenome of the subject from FIG. 9 or Table 3; sixty or more age-associated epigenetic marker(s) in the epigenome of the subject from FIG. 9 or Table 3; sixty-five or more age-associated epigenetic marker(s) in the epigenome of the subject from FIG. 9 or Table 3; or seventy or more age-associated epigenetic marker(s) in the epigenome of the subject from FIG. 9 or Table 3. For example, the set of markers having individual CpG residues subject to methylation of C-5 position of cytosine in the genome of a subject may comprise any one or more of the following methylation marker cg05652533 of Table 4, cg27367526 of Table 4, cg18404041 of Table 4, cg23606718 of FIG. 9, Tables 3 and 5, cg16867657 of FIG. 9, Tables 3 and 5, cg04474832 on chromosome 3 at position 52008487, cg05442902 on chromosome 22 at position 21369010, cg06493994 on chromosome 6 at position 25652602, cg09809672 on chromosome 1 at position 236557682, cg19722847 on chromosome 12 at position 30849114, cg22736354 on chromosome 6 at position 18122719, cg05652533 of Table 4, cg27367526 of Table 4, cg18404041 of Table 4, cg23606718 on chromosome 2 at position 131513927, and/or cg16867657 of chromosome 6 at position 11044877.

In one embodiment, the set of markers having individual CpG residues subject to methylation at C-5 position of cytosine in the genome of a subject may comprise methylation marker cg04474832 on chromosome 3 at position 52008487, cg05442902 on chromosome 22 at position 21369010, cg06493994 on chromosome 6 at position 25652602, cg09809672 on chromosome 1 at position 236557682, cg19722847 on chromosome 12 at position 30849114, and cg22736354 on chromosome 6 at position 18122719.

In another embodiment, the set of markers having individual CpG residues subject to methylation at C-5 position of cytosine in the genome of a subject may be any one or more of methylation marker cg20822990 of FIG. 9 or Table 3, cg04400972 of FIG. 9 or Table 3, cg16054275 of FIG. 9 or Table 3, cg03607117 of FIG. 9 or Table 3, cg20052760 of FIG. 9 or Table 3, cg16867657 of FIG. 9 or Table 3, cg06493994 of FIG. 9 or Table 3, cg06685111 of FIG. 9 or Table 3, cg00486113 of FIG. 9 or Table 3, cg20426994 of FIG. 9 or Table 3, cg14361627 of FIG. 9 or Table 3, cg08097417 of FIG. 9 or Table 3, cg07955995 of FIG. 9 or Table 3, cg22285878 of FIG. 9 or Table 3 and/or cg08540945 of FIG. 9 or Table 3.

In further embodiment, the set of age-associated epigenetic marker(s) may be any one or more of methylation marker cg23606718 of FIG. 9, Tables 3 and 5 and/or cg16867657 of FIG. 9, Tables 3 and 5.

In accordance with the practice of the invention, the methods of the invention may be automated.

In accordance with the practice of the invention, the biological sample may be any of blood, lymphocyte, monocyte, neutrophil, basophil, eosinophil, myeloid lineage cell, lymphoid lineage cell, bone marrow, saliva, buccal swab, nasal swab, urine, fecal material, hair, breast tissue, ovarian tissue, uterine tissue, cervical tissue, prostate tissue, testicular tissue, brain tissue, neuronal cell, astrocyte, liver tissue, kidney, thyroid tissue, stomach tissue, intestine tissue, pancreatic tissue, vascular tissue, skin, lung tissue, bone tissue, cartilage, ligament, tendon, fat cells, muscle cells, neurons, astrocytes, cultured cells with different passage number, cancer/tumor cells, cancer/tumor tissue, normal cells, normal tissue, any tissue(s) or cell(s) with a nucleus containing genetic material, or genetic material in the form of DNA of a known or unknown subject.

The tumor or cancer cells may be derived from blood, lymph node, liver, brain, esophagus, trachea, stomach, intestine, pancreas, throat, tongue, bone, ovary, uterus, cervix, peritoneum, prostate, testes, breast, kidney, lung, or skin. The biological sample with tumor or cancer cells may be predicted to have an older predicted age of at least about 30% or 40% more than the biological sample without tumor or cancer cells.

In one embodiment, the age-associated epigenetic marker(s) comprises a CpG residue. The methylation at C-5 position of cytosine may vary with the chronological age of a species associated with the subject. For example, the species associated with the subject may be *Homo sapiens*.

In another embodiment, the set of age-associated epigenetic marker(s) may comprise individual CpG residues subject to age-dependent methylation at C-5 position of cytosine in the genome of a subject. The set of markers may comprise about 70 distinct CpG residue-containing age-associated epigenetic markers. Additionally, the set of markers may comprise any one or more of markers as shown in FIG. 9, Table 3, Table 4 or Table 5.

For example, the set of age-associated markers may comprise five or more age-associated epigenetic marker(s) as shown in FIG. 9 or Table 3; ten or more age-associated epigenetic marker(s) as shown in FIG. 9 or Table 3; fifteen or more age-associated epigenetic marker(s) as shown in FIG. 9 or Table 3; twenty or more age-associated epigenetic marker(s) as shown in FIG. 9 or Table 3; twenty-five or more age-associated epigenetic marker(s) as shown in FIG. 9 or Table 3; thirty or more age-associated epigenetic marker(s) as shown in FIG. 9 or Table 3; thirty-five or more age-associated epigenetic marker(s) as shown in FIG. 9 or Table 3; forty or more age-associated epigenetic marker(s) as shown in FIG. 9 or Table 3; forty-five or more age-associated epigenetic marker(s) as shown in FIG. 9 or Table 3; fifty or more age-associated epigenetic marker(s) as shown in FIG. 9 or Table 3; fifty-five or more age-associated epigenetic marker(s) as shown in FIG. 9 or Table 3; sixty or more age-associated epigenetic marker(s) as shown in FIG. 9 or Table 3; sixty-five or more age-associated epigenetic marker(s) as shown in FIG. 9 or Table 3; or seventy or more age-associated epigenetic marker(s) as shown in FIG. 9 or Table 3.

In another embodiment, the set of age-associated markers may comprise five or more age-associated epigenetic marker(s) as shown in Table 5; ten or more age-associated epigenetic marker(s) as shown in Table 5; fifteen or more age-associated epigenetic marker(s) as shown in Table 5; twenty or more age-associated epigenetic marker(s) as shown in Table 5; twenty-five or more age-associated epigenetic marker(s) as shown in Table 5; thirty or more age-associated epigenetic marker(s) as shown in Table 5; thirty-five or more age-associated epigenetic marker(s) as shown in Table 5; forty or more age-associated epigenetic marker(s) as shown in Table 5; forty-five or more age-associated epigenetic marker(s) as shown in Table 5; or fifty or more age-associated epigenetic marker(s) as shown in Table 5.

Merely by way of example, the correlation between chronological age and predicted age may be at least about 80%, 90% or 91% with an error of less than about 5 years.

In yet another embodiment, the set of age-associated epigenetic marker(s) may be any of methylation marker cg23606718 of FIG. 9, Tables 3 and 5 and/or cg16867657 of FIG. 9, Tables 3 and 5 and the biological sample with tumor or cancer cells may be predicted to have an older predicted age of at least about 30% or 40% more than the biological sample without tumor or cancer cells.

In an embodiment, a majority of the age-associated epigenetic markers in the epigenome of the subject may predict an older age for a biological sample with tumor than biological sample of the same type without tumor. Similarly, pre-cancerous lesions may show an older biological age or predicted age than a normal tissue type without such a lesion.

In another embodiment, a majority of the age-associated epigenetic markers in the epigenome of the subject predicting an older age for a biological sample with tumor than biological sample of the same type without tumor may be more than about 70% of total age-associated epigenetic markers.

In an embodiment, one or more probes (e.g., chemical probes) may differentially react with an unmodified cytosine and 5-methyl-modified cytosine. The probe may be chosen from a set comprising a sodium bisulfite, sodium metabisulfite, and/or bisulfite salts.

In another embodiment, the outcome of reacting the isolated genomic DNA or nuclear DNA with one or more probes may be the deamination of unmodified cytosine to uracil and unaltered 5-methylcytosine. Characterizing the outcome of probing (or reacting) the isolated genomic DNA or nuclear DNA with one or more probe(s) or analyzing the methylation status may involve DNA amplification and nucleic acid sequence determination and detecting for the presence of either cytosine or thymine at the C position of the CpG dinucleotide within the age-associated epigenetic marker. Further, DNA amplification may be followed by phage RNA polymerase transcription, RNase cleavage and matrix-assisted laser desorption ionization time-of-flight mass spectrometry (MALDI-TOF MS) of RNase cleavage products.

The nucleic acid sequence determination may involve one or more of the following procedures: nucleic acid fragmentation, restriction enzyme digestion, nucleic acid hybridization, primer extension, pyrosequencing, single nucleotide extension, single nucleotide extension with biotin-labelled ddNTP, single nucleotide extension with 2,4-dinitrophenol (DNP)-labelled ddNTP, radioactive isotope labeling, non-radioactive label incorporation, fluorescent label incorporation, biotin incorporation, antigen-antibody complex formation, antibody detection, colorimetric detection, fluorescence detection, detection with fluorescent dye-labelled antibody, detection with labeled avidin or streptavidin, bead analysis or detection method, signal amplification, polymerase chain reaction, DNA amplification with thermostable DNA polymerase, phi-29 DNA polymerase DNA amplification, RNA production, in vitro transcription, phage RNA polymerase transcription, T7 RNA polymerase transcription, SP6 RNA polymerase transcription, T3 RNA polymerase transcription, RNAse digestion, RNase A digestion, DNA cloning, bacterial transformation, gel electrophoresis, mass spectroscopy, MALDI-TOF mass spectroscopy, microarray analysis, fluorescence scanner analysis, automated digital image capture, automated digital image analysis, ratiometric analysis, and Infinium® HumanMethylation450 BeadChip analysis.

In another embodiment, the proportion of unmodified cytosine initially present at each age-associated epigenetic marker may be a fraction or percent of an age-associated epigenetic marker with thymine at pyrimidine position of the CpG dinucleotide.

The ratio of 5-methylcytosine to unmodified cytosine initially present at each age-associated epigenetic marker may be the ratio of cytosine to thymidine at pyrimidine position of the CpG dinucleotide after exposure to one or more probe and following analysis of products of nucleic acid amplification.

In yet another embodiment, the ratio of unmodified cytosine to 5-methylcytosine initially present at each age-associated epigenetic marker may be the ratio of thymidine to cytosine at pyrimidine position of the CpG dinucleotide after exposure to one or more probe and following analysis of products of nucleic acid amplification.

In an embodiment, one or more restriction enzyme probe which recognizes a specific DNA sequence, is affected by a CpG dinucleotide, within or adjacent to the restriction enzyme recognition or cleavage site, and differentially cleaves the DNA based on the presence or absence of a methyl group at C-5 position of cytosine of the dinucleotide may be selected. Examples of such restriction enzymes include but are not limited to AatII, Acc65I, AccI, AciI, AclI, AfeI, AgeI, AhdI, AleI, ApaI, ApaLI, AscI, AsiSI, AvaI, AvaII, BaeI, BanI, BbrPI, BbvCI, BceAI, BcgI, BcoDI, BfuAI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DraIII, DrdI, EaeI, EagI, EarI, EciI, Eco53kI, EcoRI, EcoRV, FauI, Fnu4HI, FokI, FseI, FspI, HaeII, HaeIII, HgaI, HhaI, HincII, HinfI, HinPlI, HpaI, HpaII, Hpyl66II, Hpyl88III, Hpy99I, HpyAV, HpyCH4IV, HpyCH4V, KasI, MboI, MluI, MmeI, MspAlI, MwoI, NaeI, NarI, NciI, NgoMIV, NheI, NlaIV, NotI, NruI, Nt. BbvCI, Nt. BsmAI, Nt. CviPII, PaeR71, PhoI, PleI, PluTI, PmeI, PmlI, PshAI, PspOMI, PspXI, PvuI, RsaI, RsrII, SacII, SalI, Sau3AI, Sau96I, ScrFI, SfaNI, SfiI, SfoI, SgrAI, SmaI, SnaBI, StyD4I, TfiI, TliI, TseI, TspMI, XhoI, XmaI, and ZraI.

In an embodiment, the outcome of reacting the isolated genomic DNA or nuclear DNA with one or more restriction enzyme probe may be the production of a double-stranded DNA break at a restriction enzyme cleavage site when cytosine at a CpG dinucleotide is not modified or no double-stranded DNA break at a restriction enzyme cleavage site when cytosine at a CpG dinucleotide is modified at its C-5 position with a methyl group.

In another embodiment, analyzing the methylation status may comprise DNA amplification and analysis of age-associated epigenetic marker for specific DNA end(s) or fragment(s) due to cleavage by the restriction enzyme(s) and for intact restriction enzyme cleavage site associated at a particular age-associated epigenetic marker.

In another embodiment, the proportion of 5-methylcytosine initially present at each age-associated epigenetic marker may be a fraction or percent of the age-associated epigenetic marker with an intact restriction enzyme cleavage site due to resistance to cleavage by the restriction enzyme.

In yet another embodiment, the proportion of unmodified cytosine initially present at each age-associated epigenetic marker may be a fraction or percent of the age-associated epigenetic marker cleaved by the restriction enzyme.

In another embodiment, the ratio of 5-methylcytosine to unmodified cytosine initially present at each age-associated epigenetic marker may be the ratio of number or concentration of intact restriction enzyme cleavage sites to the number or concentration of double-stranded DNA breaks produced by the restriction enzyme for the age-associated epigenetic marker.

In another embodiment, the ratio of unmodified cytosine to 5-methylcytosine initially present at each age-associated epigenetic marker may be the ratio of number or concentration of double-stranded DNA breaks produced by the restriction enzyme to number or concentration of intact restriction enzyme cleavage sites resistant to cleavage by the restriction enzyme due to presence of 5-methylcytosine for the age-associated epigenetic marker.

In one embodiment, determining the methylation status comprises isolating genomic DNA or nuclear DNA from the sample. Additionally, the step involves probing the isolated genomic DNA or nuclear DNA with one or more probes which differentially reacts with unmodified and 5-methyl-modified cytosine and amplifying the DNA. The step also involves digesting the amplified DNA with one or more restriction enzyme that recognizes a restriction enzyme site that contains a CpG dinucleotide but fails to digest the restriction enzyme site mutated to TpG dinucleotide from a CpG dinucleotide. Further, the step involves determining the proportion of 5-methylcytosine or unmodified cytosine initially present at each age-associated epigenetic marker based on the fraction or percentage of restriction enzyme sites sensitive or resistant to digestion.

Alternatively, the methylation status may involve determining the ratio of 5-methylcytosine to unmodified cytosine initially present at each age-associated epigenetic marker based on the ratio of number or concentration of sensitive restriction enzyme sites to number or concentration of resistant restriction enzyme sites to digestion. The methylation status may also involve determining the ratio of unmodified cytosine to 5-methylcytosine initially present at each age-associated epigenetic marker based on the ratio of number or concentration of resistant restriction enzyme sites to number or concentration of sensitive restriction enzyme sites to digestion.

In another embodiment, determining the methylation status of the set of age-associated epigenetic marker(s) in the epigenome of the subject selected from FIG. 9, Tables 3, 4, and/or 5 may comprise isolating genomic DNA or nuclear DNA and fragmenting the genomic DNA or nuclear DNA. Additionally, the step involves exposing the fragmented DNA to a 5-methylcytosine-binding protein and separating 5-methylcytosine-binding protein-bound DNA fragments from 5-methylcytosine-binding protein-free DNA fragments. The step further involves determining for each age-associated epigenetic marker, the proportion of 5-methylcytosine-containing DNA fragments or unmodified cytosine-containing DNA fragments by determining the fraction or percent of 5-methylcytosine-binding protein bound or free DNA fragments, respectively, for each age-associated epigenetic marker.

Alternatively, the methylation status may involve determining for each age-associated epigenetic marker, the ratio of 5-methylcytosine-containing DNA fragments to unmodified cytosine-containing DNA fragments by determining the ratio of number or concentration of 5-methylcytosine-binding protein-bound DNA fragments to the number or concentration of 5-methylcytosine-binding protein-free DNA fragments.

The methylation status step may also involve determining for each age-associated epigenetic marker, the ratio of unmodified cytosine-containing DNA fragments to 5-methylcytosine-containing DNA fragments by determining the ratio of number or concentration of 5-methylcytosine-binding protein-free DNA fragments to the number or concentration of 5-methylcytosine-binding protein-bound DNA fragments for each age-associated epigenetic marker.

In one embodiment, the 5-methylcytosine-binding protein may be an antibody for 5-methylcytosine, MeCP2, MBD2, MBD2/MBD3L1 complex, core MBD domain of MBD2, or poly-MBD protein, a naturally occurring 5-methylcytosine binding protein, genetically engineered 5-methylcytosine binding protein, or derivative or fragment thereof.

In one embodiment, separating 5-methylcytosine-binding protein-bound DNA fragments from 5-methylcytosine-binding protein-free DNA fragments may include immunoprecipitation, immunocapture, solid phase chromatography, liquid chromatography, and/or gel electrophoresis.

In accordance with the practice of the invention, the invention provides methods for determining apparent methylomic aging rate (AMAR) of a subject. The method comprises predicting age by the method of the invention and dividing the age predicted by the actual chronological age.

In one embodiment, the invention provides methods for diagnosing the presence of tumor in a subject. The method comprises obtaining biological sample suspected to contain tumor and a second biological sample of the same type but known not to contain tumor. Additionally, the method comprises predicting the age of the each biological sample by the method of the invention. The method further comprises comparing the ages predicted for the two samples, such that a biological sample with tumor will have an older predicted age than biological sample without tumor.

In an embodiment, the invention provides a forensic diagnosis of human actual age from a tissue from a human by predicting age of a subject based on the epigenome of the subject by the method of the invention.

In another embodiment, the invention provides methods for health assessment of a subject by predicting age of a subject based on the epigenome of the subject by the method of the invention.

In yet another embodiment, the invention provides methods for screening whether an agent of interest can retard or accelerate aging process. The method comprises obtaining a biological sample from a living organism, and optionally, culturing cells, tissue, or organ derived from a living organism and predicting age or AMAR of the organism, following the method of the invention, using organism appropriate age-associated epigenetic marker(s) such that the age-associated epigenetic marker(s) for a human subject may need to be substituted with age-associated epigenetic marker(s) for the organism being examined. Additionally, the method comprises exposing the living organism or cultured living cells, tissue, or organ from the living organism to an agent of interest in a single dose, multiple doses, or continuous doses and obtaining a biological sample from the living organism or the cultured living cells, tissue, or organ. The method further comprises predicting age or AMAR of the organism from the biological sample using organism appropriate age-associated epigenetic marker(s) such that the age-associated epigenetic marker(s) for a human subject may need to be substituted with age-associated epigenetic marker(s) for the organism being examined. The method also comprises performing the same steps on another individual from the same organism or a duplicate cultured living cells, tissue, or organ from the same individual or organism but not treated with any agent of interest or treated with a placebo and comparing, for biological sample of the same predicted age or AMAR, the predicted age or AMAR of the agent-of-interest-treated organism/individual or cultured cells, tissue, or organ with the predicted age or AMAR of the untreated or placebo-treated organism/individual or cultured cells, tissue, or organ, such that a lower value or range of values for the agent-of-interest-treated organism/individual or cultured cells, tissue, or organ indicates that an agent of interest can retard an aging process whereas a higher value or range of values indicates an agent of interest can accelerate aging process. The agent of interest may be an anti-oxidant, reducing agent, DNA damaging agent, vitamin, dietary supplement, food, food additive, food coloring, salt, vegetable, vegetable extract, fruit, fruit extract, flower, flower extract, fragrance, seed, seed extract, herb, herb extract, plant extract, fiber, fat, fatty acid, oil, sugar, artificial sweetener, probiotics, alcohol, wine, fungus, mold, cream, lotion, powder, makeup, sun blocker, gas, pollutant, smoke, environmental pollutant, paint, solvent, organic solvent, plastic, plasticizers, bisphenol, phenolic compounds, tobacco, inhalant, drug, biologic, hormone, endocrine disruptor, environmental estrogen, hormone antagonist, hormone agonist, caffeine, phytoestrogen, metal, enzyme, chelator, yogurt, sulfur compound, physical barrier, electromagnetic barrier, and radiation barrier.

In an embodiment, the organism may be yeast, fruit fly, fish, worm, insect, zebra fish, nematode, plant, or mammal. Mammal includes, but is not limited to, human, murine, simian, feline, canine, equine, bovine, porcine, ovine, caprine, rabbit, mammalian farm animal, mammalian sport animal, and mammalian pet.

In one embodiment, the invention provides methods for identifying type of tissue for a biological sample from a subject with a known chronological age. The method comprises ascertaining the chronological age of a subject and determining the predicted age of the subject from the biological sample by the method of the invention. Additionally, the method comprises comparing to a reference standard relating the predicted age for various types of tissue to chronological age and determining which value closely matches the predicted age in the reference standard for various types of tissue. Further, the method comprises assigning the type of tissue for the biological sample based on the closest match.

The invention also provides methods for identifying type of tissue for a biological sample from a subject with a known chronological age. The method comprises ascertaining the chronological age of a subject and determining the AMAR of the subject from the biological sample by dividing the predicted age of a subject from the chronological age of the subject. Additionally, the method comprises comparing to a reference standard relating the AMAR to chronological age for various types of tissue and determining which value closely matches the AMAR in the reference standard for various types of tissue. The method further comprises assigning the type of tissue for the biological sample based on the closest match.

In one embodiment, the set of age-associated epigenetic marker(s) comprises any one or more of methylation marker cg23606718 of FIG. 9, Tables 3 and 5 and/or cg16867657 of FIG. 9, Tables 3 and 5.

The invention further provides methods for predicting age of a subject based on age-associated epigenetic modification affecting gene expression. The method comprises obtaining a biological sample of the subject and determining the expression of one or more gene(s) associated with age-associated epigenetic marker(s) whose expression changes with age. Additionally, the method comprises comparing the expression of one or more gene(s) associated with age-associated epigenetic marker(s) whose expression changes with age with the expression of the same gene(s) from an age-correlated reference population. The method further comprises obtaining a value or range of values for the predicted age of the subject. Comparing the expression of one or more gene(s) associated with age-associated epigenetic marker(s) whose expression changes with age with the expression of the same gene(s) from an age-correlated reference population may comprise any statistical method, multivariate regression method, linear regression analysis, tabular method, or graphical method used to predict the age of a subject based on expression of gene(s) associated with age-associated epigenetic marker(s) whose expression changes with age. In one embodiment, the statistical method may be a multivariate regression algorithm or linear regression algorithm.

In another embodiment, one or more gene(s) associated with age-associated epigenetic marker(s) whose expression changes with age may comprise one or more of the genes listed in Table 6 or Table 7.

In another embodiment, the gene expression may be a transcription or translation. In another embodiment, the transcription results in the production of RNA transcripts and translation results in the production of proteins.

In accordance with the practice of the invention, the invention provides a method of screening a tissue sample from a subject in order to predict the age of the tissue sample based on the epigenome of the subject by the method the invention.

In one embodiment, the tissue sample may be exposed to at least one test agent in a high-throughput screening assay. In another embodiment, said process may be used for any one of diagnosis and/or high-throughput screening.

The invention also provides methods for predicting age of a tissue or organ of a subject based on the epigenome of the tissue or organ of the subject. The method comprises obtaining a biological sample of a tissue or organ from the subject and determining the methylation status of a set of age-associated epigenetic marker(s) in the epigenome of the subject selected from FIG. 9, Tables 3, 4, and/or 5. The method further comprises comparing the methylation status of a set of age-associated epigenetic marker(s) of the subject with the methylation status of the same markers from an age-correlated reference population so as to obtain a value or a range of values for the predicted age of the tissue or organ.

The methylation status of the same markers from an age-correlated reference population may be determined on a same or a different type of tissue or organ. The methylation status of the same markers from an age-correlated reference population may be determined on blood or fractionated blood.

In an embodiment, the methods of the invention provides for determining differential aging rates of tissues or organs of a subject. The method comprises obtaining biological samples from different tissue(s) or organ(s) from the subject and predicting the age of the tissue or organ using the methods of the invention. The method further comprises comparing the predicted ages where a difference in the predicted ages indicates a difference in the aging rate of the tissue(s) or organ(s) of the subject. The predicted age may be divided by the chronological age of the subject to obtain AMAR.

Compositions of the Invention

The invention further provides compositions which comprise a set of epigenetic markers based on five or more age-associated epigenetic marker(s) in the epigenome of the subject selected from FIG. 9, Tables 3, 4, and/or 5; ten or more age-associated epigenetic marker(s) in the epigenome of the subject selected from FIG. 9, Tables 3, 4, and/or 5; fifteen or more age-associated epigenetic marker(s) in the epigenome of the subject selected from FIG. 9, Tables 3, 4, and/or 5; twenty or more age-associated epigenetic marker(s) in the epigenome of the subject selected from FIG. 9, Tables 3, 4, and/or 5; twenty-five or more age-associated epigenetic marker(s) in the epigenome of the subject selected from FIG. 9, Tables 3, 4, and/or 5; thirty or more age-associated epigenetic marker(s) in the epigenome of the subject selected from FIG. 9, Tables 3, 4, and/or 5; thirty-five or more age-associated epigenetic marker(s) in the epigenome of the subject selected from FIG. 9, Tables 3, 4, and/or 5; forty or more age-associated epigenetic marker(s) in the epigenome of the subject selected from FIG. 9, Tables 3, 4, and/or 5; forty-five or more age-associated epigenetic marker(s) in the epigenome of the subject selected from FIG. 9, Tables 3, 4, and/or 5; fifty or more age-associated epigenetic marker(s) in the epigenome of the subject selected from FIG. 9, Tables 3, 4, and/or 5; fifty-five or more age-associated epigenetic marker(s) in the epigenome of the subject selected from FIG. 9, Tables 3, 4, and/or 5; sixty or more age-associated epigenetic marker(s) in the epigenome of the subject selected from FIG. 9, Tables 3, 4, and/or 5; sixty-five or more age-associated epigenetic marker(s) in the epigenome of the subject selected from FIG. 9, Tables 3, 4, and/or 5; or seventy or more age-associated epigenetic marker(s) in the epigenome of the subject selected from FIG. 9, Tables 3, 4, and/or 5.

Further, in a preferred embodiment, the composition may comprise a set of epigenetic markers based on five or more age-associated epigenetic marker(s) in the epigenome of the subject from FIG. 9 or Table 3; ten or more age-associated epigenetic marker(s) in the epigenome of the subject from FIG. 9 or Table 3; fifteen or more age-associated epigenetic marker(s) in the epigenome of the subject from FIG. 9 or Table 3; twenty or more age-associated epigenetic marker(s) in the epigenome of the subject from FIG. 9 or Table 3; twenty-five or more age-associated epigenetic marker(s) in the epigenome of the subject from FIG. 9 or Table 3; thirty or more age-associated epigenetic marker(s) in the epigenome of the subject from FIG. 9 or Table 3; thirty-five or more age-associated epigenetic marker(s) in the epigenome of the subject from FIG. 9 or Table 3; forty or more age-associated epigenetic marker(s) in the epigenome of the subject from FIG. 9 or Table 3; forty-five or more age-associated epigenetic marker(s) in the epigenome of the subject from FIG. 9 or Table 3; fifty or more age-associated epigenetic marker(s) in the epigenome of the subject from FIG. 9 or Table 3; fifty-five or more age-associated epigenetic marker(s) in the epigenome of the subject from FIG. 9 or Table 3; sixty or more age-associated epigenetic marker(s) in the epigenome of the subject from FIG. 9 or Table 3; sixty-five or more age-associated epigenetic marker(s) in the epigenome of the subject from FIG. 9 or Table 3; or seventy or more age-associated epigenetic marker(s) in the epigenome of the subject from FIG. 9 or Table 3. For example, the set of age-associated epigenetic marker(s) may comprise any one or more of the following methylation marker cg05652533 of Table 4, cg27367526 of Table 4, cg18404041 of Table 4, cg23606718 of FIG. 9, Tables 3 and 5, cg16867657 of FIG. 9, Tables 3 and 5, cg04474832 on chromosome 3 at position 52008487, cg05442902 on chromosome 22 at position 21369010, cg06493994 on chromosome 6 at position 25652602, cg09809672 on chromosome 1 at position 236557682, cg19722847 on chromosome 12 at position 30849114, cg22736354 on chromosome 6 at position 18122719, cg05652533 of Table 4, cg27367526 of Table 4, cg18404041 of Table 4, cg23606718 on chromosome 2 at position 131513927, and/or cg16867657 of chromosome 6 at position 11044877.

In yet another embodiment, the composition comprises a set of age-associated epigenetic marker(s) of methylation marker cg04474832 on chromosome 3 at position 52008487, cg05442902 on chromosome 22 at position 21369010, cg06493994 on chromosome 6 at position 25652602, cg09809672 on chromosome 1 at position 236557682, cg19722847 on chromosome 12 at position 30849114, and cg22736354 on chromosome 6 at position 18122719.

In another embodiment, the composition comprises a set of age-associated epigenetic marker(s) of any one or more of methylation marker cg20822990 of FIG. 9 or Table 3, cg04400972 of FIG. 9 or Table 3, cg16054275 of FIG. 9 or Table 3, cg03607117 of FIG. 9 or Table 3, cg20052760 of FIG. 9 or Table 3, cg16867657 of FIG. 9 or Table 3, cg06493994 of FIG. 9 or Table 3, cg06685111 of FIG. 9 or Table 3, cg00486113 of FIG. 9 or Table 3, cg20426994 of FIG. 9 or Table 3, cg14361627 of FIG. 9 or Table 3, cg08097417 of FIG. 9 or Table 3, cg07955995 of FIG. 9 or Table 3, cg22285878 of FIG. 9 or Table 3 and/or cg08540945 of FIG. 9 or Table 3.

In further embodiment, the composition comprises a set of age-associated epigenetic marker(s) of any one or more of methylation marker cg23606718 of FIG. 9, Tables 3 and 5 and/or cg16867657 of FIG. 9, Tables 3 and 5.

Kits

According to another aspect of the invention, kits are provided. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compounds or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler. In still other embodiments compounds are provided in a polymeric matrix or in the form of a liposome.

The invention provides for a kit for determining age of a subject based on epigenetic modification of subject's genetic material comprising the set of age-associated epigenetic marker or markers as listed in FIG. 9, Table 3, Table 4 or Table 5 as described in the methods of the invention, supra.

The invention further provides for a kit for predicting age of a subject based on the epigenome of the subject utilizing the set of the age-associated epigenetic marker(s) provided in FIG. 9, Table 3, 4 and/or 5 as described in the methods of the invention, supra.

In one embodiment, the age-associated epigenetic marker(s) may comprise a nucleic acid with a CpG dinucleotide. In another embodiment, the cytosine of the CpG dinucleotide may be subject to age-dependent changes in methylation at the C-5 position. In another embodiment, the CpG dinucleotide is at the chromosomal position as indicated in FIG. 9, Table 3, 4, and/or 5.

In an embodiment, the age-associated epigenetic marker(s) may be a human marker and selected from cg04474832 on chromosome 3 at position 52008487, cg05442902 on chromosome 22 at position 21369010, cg06493994 on chromosome 6 at position 25652602, cg09809672 on chromosome 1 at position 236515682, cg19722847 on chromosome 12 at position 30849114, cg22736354 on chromosome 6 at position 18122719, cg05652533 of Table 4, cg27367526 of Table 4, cg18404041 of Table 4, cg23606718 on chromosome 2 at position 131513927, and cg16867657 of chromosome 6 at position 11044877.

In yet another embodiment, the age-associated epigenetic marker(s) may have the sequence as provided in FIG. 9 or as can be found at the National Center for Biotechnology Information of the National Institutes of Health (Bethesda, Md.) in the Gene Expression Omnibus (GEO) database with GEO accession number GPL13534.

The following examples are provided to further illustrate aspects of the invention. These examples are non-limiting and should not be construed as limiting any aspect of the invention.

EXAMPLES

Example 1

Materials and Methods

Sample Collection and Test Procedures

This study was approved by the institutional review boards of the University of California, San Diego; the University of Southern California; and West China Hospital. All participants signed informed consent statements prior to participation. Blood was drawn from a vein in the patient's arm into blood collection tubes containing the anticoagulant acid citrate dextrose. Genomic DNA was extracted from the whole blood with a QIAGEN FlexiGene DNA Kit and stored at −20° C. Methylation fraction values for the autosomal chromosomes were measured with the Illumina Infinium HumanMethylation450 BeadChip (Bibikova et al., 2011). This procedure uses bisulfate-treated DNA and two site-specific probes for each marker, which bind to the associated methylated and unmethylated sequences. The intensity of the methylated probe relative to the total probe intensity for each site represents the fractional level of methylation at that site in the sample. These values were adjusted for internal controls with Illumina's Genome Studio software. Methylation fraction values with a detection p value greater than 0.01 were set to "missing." One patient sample and 830 markers were removed as they had greater than 5% missing values. The remaining missing values were imputed with the KNN approach (ten nearest markers) using the R "impute" package (Troyanskaya et al., 2001). We performed exome sequencing on 258 of these samples, using a solution hybrid selection method to capture DNA followed by parallel sequencing on an Illumina HiSeq platform. Genotype calls were made with the SOAP program (Li et al., 2008). Calls with a quality score less than twenty were set as missing. Only variants that had fewer than 10% missing calls, were within Hardy-Weinberg equilibrium ($p \le 10^{-4}$), and were of a common frequency (>5%) were retained (10,694). Individuals with less than 20% missing calls (252) were retained. Additional genotyping was done with multiplex PCR followed by MALDI-TOF mass spectrometry analysis with the iPLEX/MassARRAY/Typer platform.

Methylation Quality Control

We used principal component (PC) analysis to identify and remove outlier samples. We converted each sample into a z score statistic, based on the squared distance of its 1st PC from the population mean. The z statistic was converted to a false-discovery rate with the Gaussian cumulative distribution and the Benjamini-Hochberg procedure (Benjamini and Hochberg, 1995). Samples falling below an FDR of 0.2 were designated at outliers and removed. This filtering procedure was performed iteratively until no samples were determined to be an outlier. A total of 24 samples were removed in this manner.

Association Testing

Association tests for trends in methylation fraction and deviance were performed with nested linear models and the F test. As methylation levels may be sensitive to a number of factors, we included several covariates, including gender, BMI, diabetes status, ethnicity, and batch. Tests for whole-methylome changes in deviance were computed with the binomial test, based on the number of markers with a positive rather than negative coefficient. Markers were annotated as having support from the TCGA data when the coefficient of aging was the same sign and the significance was better than $p < 0.05$.

Annotation Enrichment

Methylation marker annotations for CpG islands and GO terms were obtained from the IlluminaHumanMethylation450k.db database from Bioconductor (Gentleman et al., 2004). Annotation enrichment tests were performed with the two-sided Fisher's exact test.

Aging Model

The diagnostic model of age was made with a multivariate linear model approach based on the Elastic Net algorithm implemented in the R package "glmnet" (Friedman et al., 2010). This approach is a combination of traditional Lasso and ridge regression methods, emphasizing model sparsity while appropriately balancing the contributions of correlated variables. It is ideal for building linear models in situations where the number of variables (markers) greatly outweighs the number of samples. Optimal regularization parameters were estimated via 10-fold crossvalidation. We employed bootstrap analysis, sampling the data set with replacement 500 times and building a model for each bootstrap cohort. We included in the final model only markers that were present in more than half of all bootstraps. The covariates gender, BMI, diabetes status, ethnicity, and batch were included in the model and were exempted from penalization (regularization). p values are based on a least-squares model built with the same terms and drop-one F tests. As BMI was strongly associated with age, the term was first adjusted for age before computing significance in the model. AMAR was computed with the aging model, but without the variables of gender, BMI, and diabetes status. The coefficients were not changed. AMAR was then taken as an individual's predicted age divided by her or his actual age.

Genetic Variant Associations

Each genetic variant was tested for association in an additive model with the top aging-associated methylation markers with nested linear models and the F test. We included covariates for gender, BMI, diabetes status, ethnicity, and batch. Variant positions were based on the human reference build GRCh37 and gene annotations were based on chromosomal proximity within 20 kbp.

Computing Methylation Deviance

Methylation deviance was computed via the following approach: First, we removed the methylation trends due to all given variables, including age, gender, and BMI by fitting a linear model for each marker and acting only on the residuals. Next, we identified and removed highly nonnormal markers on the basis of the Shapiro-Wilk test ($p<10^{-5}$). To allow for naturally occurring extreme deviations in the normality test, we first estimated the outliers of each marker based on a Grubb's statistic, choosing the inclusion threshold based on the Benjamini-Hochberg FDR (Benjamini and Hochberg, 1995). If any samples had an FDR less than 0.4, we ignored them and repeated the outlier detection until no outliers were detected. Finally, the deviance of each remaining marker was computed as the square of its adjusted methylation value.

Entropy Analysis

Entropy statistics were computed on methylation data adjusted for covariates and filtered for normality (see Computing Methylation Deviance). We computed the normalized Shannon entropy (Shannon and Weaver, 1963) of an individual's methylome according to the formula $$\text{Entropy} = \frac{1}{N*\log\left(\frac{1}{2}\right)} \sum_i [MFi*\log(MFi) + (1 - MFi)*\log(1 - MFi)],$$

where MFi is the methylation fraction of the $i^{th}$ methylation marker and N is the number of markers.

Mapping CpG Islands

Genomic positions and marker annotations for 27,176 CpG islands were obtained from the IlluminaHumanMethylation450k.db database from Bioconductor (Gentleman et al., 2004). We obtained the positions for markers within each island with at least four markers (25,028), as well as the nearest 100 markers upstream and downstream. These positions were then combined with the marker value of interest (i.e., methylation fraction, aging coefficient, or deviance) to produce a genomic map for each island and the surrounding region. After normalizing each map to the center of the island, we averaged the values at each relative genomic point across all islands to produce a common map.

Results and Discussion

Global Methylomic Profiling Over a Wide Age Range

We obtained methylome-wide profiles of two different cohorts (N1=482, N2=174) sampled from a mixed population of 426 Caucasian and 230 Hispanic individuals, aged 19 to 101. Samples were taken as whole blood and processed with the Illumina Infinium HumanMethylation450 BeadChip assay (Bibikova et al., 2011), which measures the methylation states of 485,577 CpG markers. Methylation was recorded as a fraction between zero and one, representing the frequency of methylation of a given CpG marker across the population of blood cells taken from a single individual. Conservative quality controls were applied to filter spurious markers and samples. For simplicity, we discarded values for markers on sex chromosomes. Association tests revealed that 70,387 (15%) of the markers had significant associations between methylation fraction and age (FIG. 1, false discovery rate [FDR]<0.05 by F test). We were able to verify at a p<0.05 significance level 53,670 (76%) of these associations using 40 young and old samples recently published by Heyn et al. (2012). More detailed accounts of the individual aging markers and their genomic features are presented in the FIG. 10 and Tables 1 and 2. The resulting data set represents the largest and highest-resolution collection of methylation data produced for the study of aging, providing an unprecedented opportunity to understand the role of epigenetics in the aging process. The complete methylation profiles are available at the Gene Expression Omnibus (GSE40279).

Figure 1:
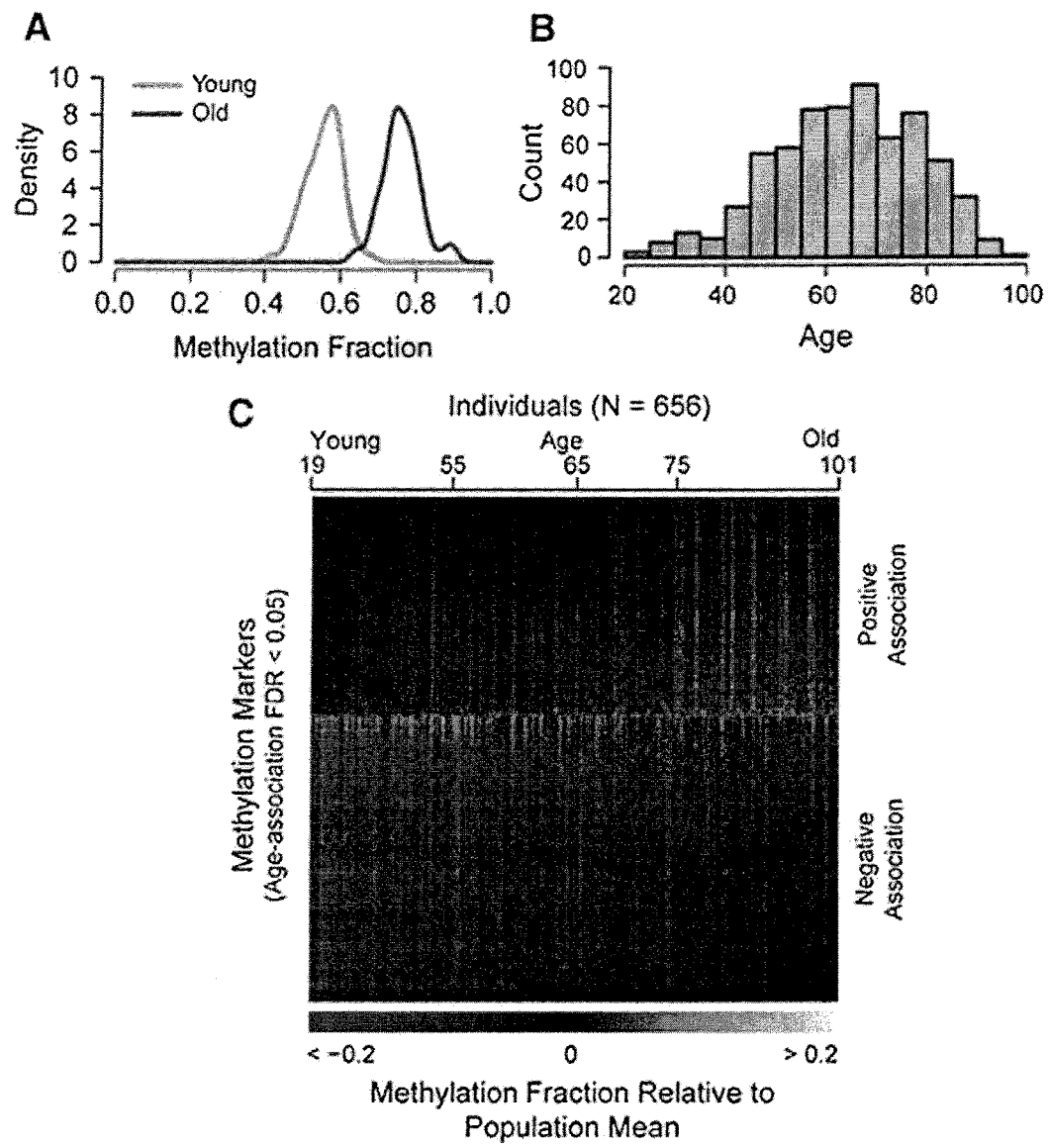
FIG. 1. Global Data on the Aging Methylome. (A) A density plot of methylation fraction values for the marker cg16867657, separated by young (green) and old (blue) individuals. (B) A histogram of the age distribution for all individuals. (C) A heatmap of the age-associated methylation markers, sorted by the magnitude of association (regression coefficient). The individuals are ordered youngest to oldest. See also FIG. 10 and Tables 1 and 2 for a specific example of an age-associated region and for annotation coincidence tables, respectively.

Table 1, Functional Annotations for Age-Associated Markers, Related to FIG. 1

Genes with nearby age-associated markers were enriched for many functions. A selection of these functions are shown here.

| Over-enriched Terms | Under-enriched Terms |
| --- | --- |
| Cell communication (FDR ~$10^{-76}$) | G-protein coupled receptor activity (FDR < $10^{-11}$) |
| Locomotion (FDR < $10^{-33}$) | Ribosome (FDR < $10^{-5}$) |
| Cell proliferation (FDR < $10^{-17}$) | RNA splicing (FDR < 0.05) |
| Growth (FDR < $10^{-7}$) | M phase (FDR < 0.05) |

Table 2, Age-Associated Marker Properties, Related to FIG. 1

A table of age-associated markers and their coincidence with several genomic features. Each value represents the percentage of the age-associated markers of a particular type (columns) that are coincident with a particular annotation (rows).

|  | All Markers (%) | Increasing Mean (%) | Decreasing Mean (%) | Increasing Variance (%) |
| --- | --- | --- | --- | --- |
| MF > 0.5 | 55 | 13 | 57 | 51 |
| MF < 0.5 | 45 | 87 | 43 | 49 |
| CpG Island | 31 | 68 | 8 | 24 |
| CpG Shore | 23 | 18 | 35 | 36 |
| CpG Shelf | 10 | 3 | 13 | 8 |
| Enhancer | 22 | 22 | 30 | 27 |
| Promoter | 20 | 7 | 13 | 8 |
| DHS | 12 | 30 | 14 | 16 |

A Predictive Model for the Aging Methylome

We built a predictive model of aging on the primary cohort using a penalized multivariate regression method known as Elastic Net (Zou and Hastie, 2005), combined with bootstrap approaches. The model included both methylomic and clinical parameters such as gender and body mass index (BMI) (FIG. 2A). The optimal model selected a set of 71 methylation markers that were highly predictive of age (FIG. 2A and Table 3). The accuracy of the model was high, with a correlation between age and predicted age of 96% and an error of 3.9 years (FIG. 2B). Nearly all markers in the model lay within or near genes with known functions in aging-related conditions, including Alzheimer's disease, cancer, tissue degradation, DNA damage, and oxidative stress. By way of example, two markers lay within the gene somatostatin (SS7), a key regulator of endocrine and nervous system function (Yacubova and Komuro, 2002). SST is known to decline with age and has been linked to Alzheimer's disease (Saito et al., 2005). As a second example, six model markers lay within the transcription factor KLF14, which has been called a "master regulator" of obesity and other metabolic traits (Small et al., 2011). Given the links between aging, longevity, and metabolic activity (Lane et al., 1996; Tatar et al., 2003), it is not surprising that several of our model markers are implicated in obesity and metabolism.

Figure 2:
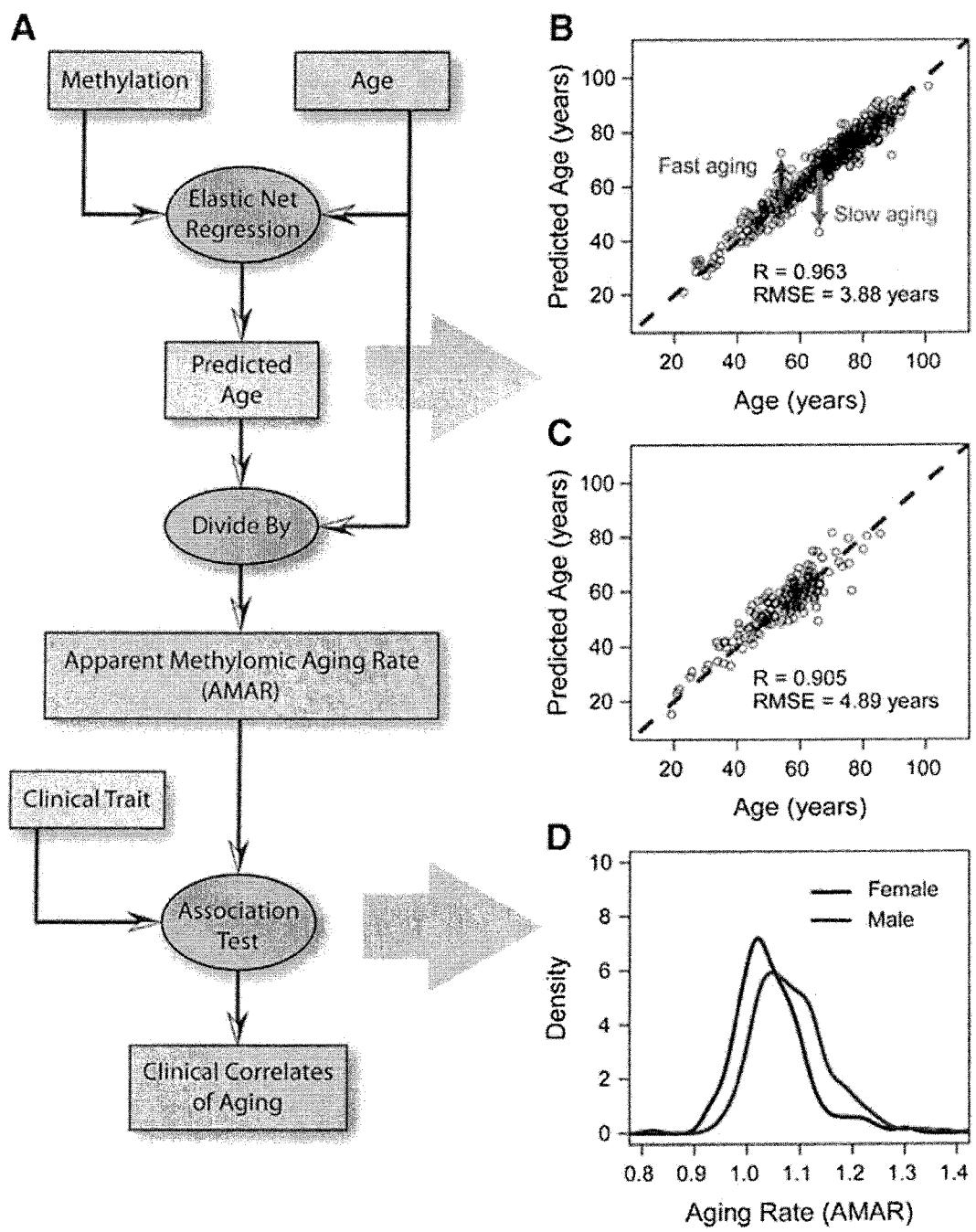
FIG. 2. Model Predictions and Clinical Variables. (A) A flow chart of the data (green boxes) and analyses (red ovals) used to generate aging predictions (blue boxes). (B) A comparison of predicted and actual ages for all individuals based on the aging model. (C) Out-of-sample predictions for individuals in the validation cohort. (D) Apparent methylomic aging rate (AMAR) for each individual, based on the aging model without clinical variables. The distribution of aging rates shows faster aging for men than women. A table of the markers used in the aging model is provided in Table 3. See also FIGS. 11 and 12, Table 3 and FIG. 9.

Table 3, Aging Model Markers, Related to FIG. 2

A table of the methylation markers included in the primary aging model. The coefficient listed for each marker is its regression coefficient within the model. A second table is provided for the model based on all samples (primary and validation).

| Marker | Chromosome | Position | Genes | CpG Island | Coefficient |
|---|---|---|---|---|---|
| cg20822990 | 1 | 17338766 | ATP13A2, SDHB | No | −15.7 |
| cg22512670 | 1 | 26855765 | RPS6KA1 | No | 1.05 |
| cg25410668 | 1 | 28241577 | RPA2, SMPDL3B | No | 3.87 |
| cg04400972 | 1 | 117665053 | TRIM45, TTF2 | Yes | 9.62 |
| cg16054275 | 1 | 169556022 | F5, SELP | No | −11.1 |
| cg10501210 | 1 | 207997020 | C1orf132 | No | −6.46 |
| cg09809672 | 1 | 236557682 | EDARADD | No | −0.74 |
| ch.2.30415474F | 2 | 30561970 | LBH | No | 5.79 |
| cg22158769 | 2 | 39187539 | ARHGEF33 | Yes | −2.06 |
| cg02085953 | 2 | 97202260 | ARID5A | No | 1.02 |
| cg06639320 | 2 | 106015739 | FHL2 | Yes | 8.95 |
| cg22454769 | 2 | 106015767 | FHL2 | Yes | 4.85 |
| cg24079702 | 2 | 106015771 | FHL2 | Yes | 2.48 |
| cg23606718 | 2 | 131513927 | FAM123C | Yes | 8.35 |
| cg22016779 | 2 | 230452311 | DNER, RNU7-9P | No | 1.79 |
| cg04474832 | 3 | 52008487 | ABHD14A, ABHD14B, ACY1, GPR62, PCBP4, RPL29 | No | −7.1 |
| cg03607117 | 3 | 53080440 | SFMBT1 | Yes | 10.7 |
| cg07553761 | 3 | 160167977 | SMC4, TRIM59 | Yes | 3.72 |
| cg00481951 | 3 | 187387650 | SST | No | −2.72 |
| cg25478614 | 3 | 187387866 | SST | No | 4.01 |
| cg25428494 | 4 | 84255411 | HPSE | No | −1.81 |
| cg02650266 | 4 | 147558239 | POU4F2 | Yes | 10.2 |
| cg08234504 | 5 | 139013317 | CTD-3224K15.2, CXXC5, UBE2D2 | No | −3.16 |
| cg23500537 | 5 | 140419819 | PCDHB1 | No | 5.67 |
| cg20052760 | 6 | 10510789 | GCNT2 | No | −12.6 |
| cg16867657 | 6 | 11044877 | ELOVL2 | Yes | 10.8 |
| cg22736354 | 6 | 18122719 | NHLRC1, TPMT | Yes | 4.42 |
| cg06493994 | 6 | 25652602 | SCGN | Yes | 9.42 |
| cg06685111 | 6 | 30295466 | XXbac-BPG283O16.8 | No | −13.1 |
| cg00486113 | 6 | 31105711 | | No | −10.7 |
| cg13001142 | 6 | 147528521 | STXBP5 | No | −5.8 |
| cg20426994 | 7 | 130418324 | KLF14 | Yes | 19.1 |
| cg14361627 | 7 | 130419116 | KLF14 | Yes | 10.7 |
| cg08097417 | 7 | 130419133 | KLF14 | Yes | 27.3 |
| cg07955995 | 7 | 130419159 | KLF14 | Yes | 13.7 |
| cg22285878 | 7 | 130419173 | KLF14 | Yes | −20.7 |
| cg03473532 | 7 | 131008743 | MKLN1 | No | −3.31 |
| cg08540945 | 7 | 152591698 | | Yes | 9.41 |
| cg07927379 | 7 | 156433108 | C7orf13, RNF32 | Yes | −1.42 |
| cg16419235 | 8 | 57360613 | PENK | Yes | −1.6 |
| cg07583137 | 8 | 82644012 | CHMP4C, ZFAND1 | No | 3.03 |
| cg22796704 | 10 | 49673534 | ARHGAP22 | No | −10.6 |
| cg19935065 | 10 | 98062687 | DNTT | No | 13.4 |
| cg23091758 | 11 | 9025767 | NRIP3, SCUBE2 | Yes | −0.392 |
| cg23744638 | 11 | 10323902 | ADM, AMPD3, SBF2 | No | 0.0859 |
| cg04940570 | 11 | 12696758 | TEAD1 | Yes | 11.6 |
| cg11067179 | 11 | 66083541 | CD248, RIN1, TMEM151A | No | 14.7 |
| cg22213242 | 11 | 66083573 | CD248, RIN1, TMEM151A | Yes | 23.7 |
| cg06419846 | 11 | 66083697 | CD248, RIN1, TMEM151A | Yes | 13.4 |
| cg02046143 | 11 | 133797911 | IGSF9B | No | −10.2 |
| cg00748589 | 12 | 11653486 | | Yes | 8.21 |
| cg19722847 | 12 | 30849114 | CAPRIN2, IPO8 | No | −5.66 |
| cg18473521 | 12 | 54448265 | HOXC4, HOXC5 | No | 8.85 |
| cg01528542 | 12 | 81468232 | ACSS3 | No | −2.98 |
| ch.13.39564907R | 13 | 40666907 | | No | −20.6 |
| cg03032497 | 14 | 61108227 | SIX1 | No | 8.4 |
| cg04875128 | 15 | 31775895 | OTUD7A | Yes | −4.37 |
| cg21296230 | 15 | 33010536 | GREM1 | Yes | 8.39 |
| cg09651136 | 15 | 72525012 | PARP6, PKM2 | No | −15.8 |
| cg03399905 | 15 | 79576060 | ANKRD34C | Yes | 28 |
| cg04416734 | 16 | 30075192 | ALDOA, PPP4C | No | 11.9 |
| cg07082267 | 16 | 85429035 | | No | 2.87 |
| cg14692377 | 17 | 28562685 | BLMH, SLC6A4, SNORD63.3 | Yes | 19.1 |
| cg06874016 | 17 | 40177415 | DNAJC7, NKIRAS2, ZNF385C | No | −4.37 |
| cg21139312 | 17 | 55663225 | MSI2 | No | 17.1 |
| cg02867102 | 17 | 62398693 | | No | −12.5 |
| cg19283806 | 18 | 66389420 | CCDC102B, TMX3 | No | −4.29 |
| cg14556683 | 19 | 15342982 | BRD4, EPHX3 | Yes | −4.04 |
| cg07547549 | 20 | 44658225 | MMP9, SLC12A5 | Yes | 3.11 |
| cg05442902 | 22 | 21369010 | LZTR1, MIR649, P2RX6, SLC7A4, THAP7 | No | −22.7 |

-continued

| Marker | Chromosome | Position | Genes | CpG Island | Coefficient |
|---|---|---|---|---|---|
| cg08415592 cg24724428 | 22 | 36648973 | APOL1, APOL2, Z82215.1 | No | −6.92 |

We validated this model on the secondary cohort, consisting of an additional 174 independent samples. These samples were processed in the same manner as the primary cohort and were then used to predict age based on the original model (i.e., as trained on the original cohort). The predictions were highly accurate, with a correlation between age and predicted age of 91% and an error of 4.9 years (FIG. 2C). The significance of the aging model was also confirmed by the data set presented in Heyn et al., verifying the age association of 70 of the 71 markers (Heyn et al., 2012). Furthermore, the model was able to fully separate old and young individuals in the Heyn et al. study, even for profiles obtained via bisulfate sequencing rather than the bead-chip technology used in this study (FIG. 11).

Methylome Aging Rate and its Associations

While the aging model is able to predict the age of most individuals with high accuracy, it is equally valuable as a tool for identifying individual outliers who do not follow the expectation. For example, FIG. 2B highlights two individuals whose age is vastly over- or under-predicted on the basis of their methylation data. To examine whether these differences reflect true biological differences in the state of the individual (i.e., versus measurement error or intrinsic variability), we used the aging model to quantify each individual's apparent methylomic aging rate (AMAR), defined as the ratio of the predicted age, based on methylation data, to the chronological age. We then tested for associations between AMAR and possibly relevant clinical factors, including gender and BMI. Analysis of ethnicity and diabetes status was not possible due to correlations with batch variables (FIG. 12). We found that gender, but not BMI had significant contributions to aging rate (F test, $p=6 \times 10^{-6}$, $p>0.05$). The methylome of men appeared to age approximately 4% faster than that of women (FIG. 2D), even though the overall distributions of age were not significantly different between the men and women in the cohort ($p>0.05$, KS test). Likewise, the validation cohort confirmed the increased aging rate for men ($p<0.05$), but was inconclusive for BMI ($p>0.05$). This complements a previous finding of an epigenetic signal for BMI that does not change with age (Feinberg et al., 2010).

As genetic associations have been previously reported with human longevity and aging phenotypes (Atzmon et al., 2006; Suh et al., 2008; Willcox et al., 2008; Wheeler et al., 2009), we examined whether the model could distinguish aging rates for individuals with different genetic variants. For this purpose, we obtained whole-exome sequences for 252 of the individuals in our methylome study at 15× coverage. After sequence processing and quality control, these sequences yielded 10,694 common single-nucleotide variants across the population. As a negative control, we confirmed that none of the genetic variants were significant predictors of age itself, which is to be expected since the genome sequence is considered to be relatively static over the course of a lifetime. On the other hand, one might expect to find genetic variants that modulate the methylation of age-associated markers, i.e., methylation quantitative-trait loci or meQTLs (Bell et al., 2011). Testing each genetic variant for association with the top age-associated methylation markers, we identified 303 meQTLs (FDR<0.05, FIG. 3A). For validation, we selected eight genetic variants (corresponding to 14 meQTLs) to test in a validation cohort of 322 individuals from our methylation study. This analysis found that seven of eight genetic variants (corresponding to seven meQTLs) remained highly significant in the validation cohort (FDR<0.05, Table 4). While all of these variants acted in cis with their meQTLs (within 150 kbp), we confirmed that none directly modified the CpG site or associated probe sequence of the associated methylation marker.

Figure 3:
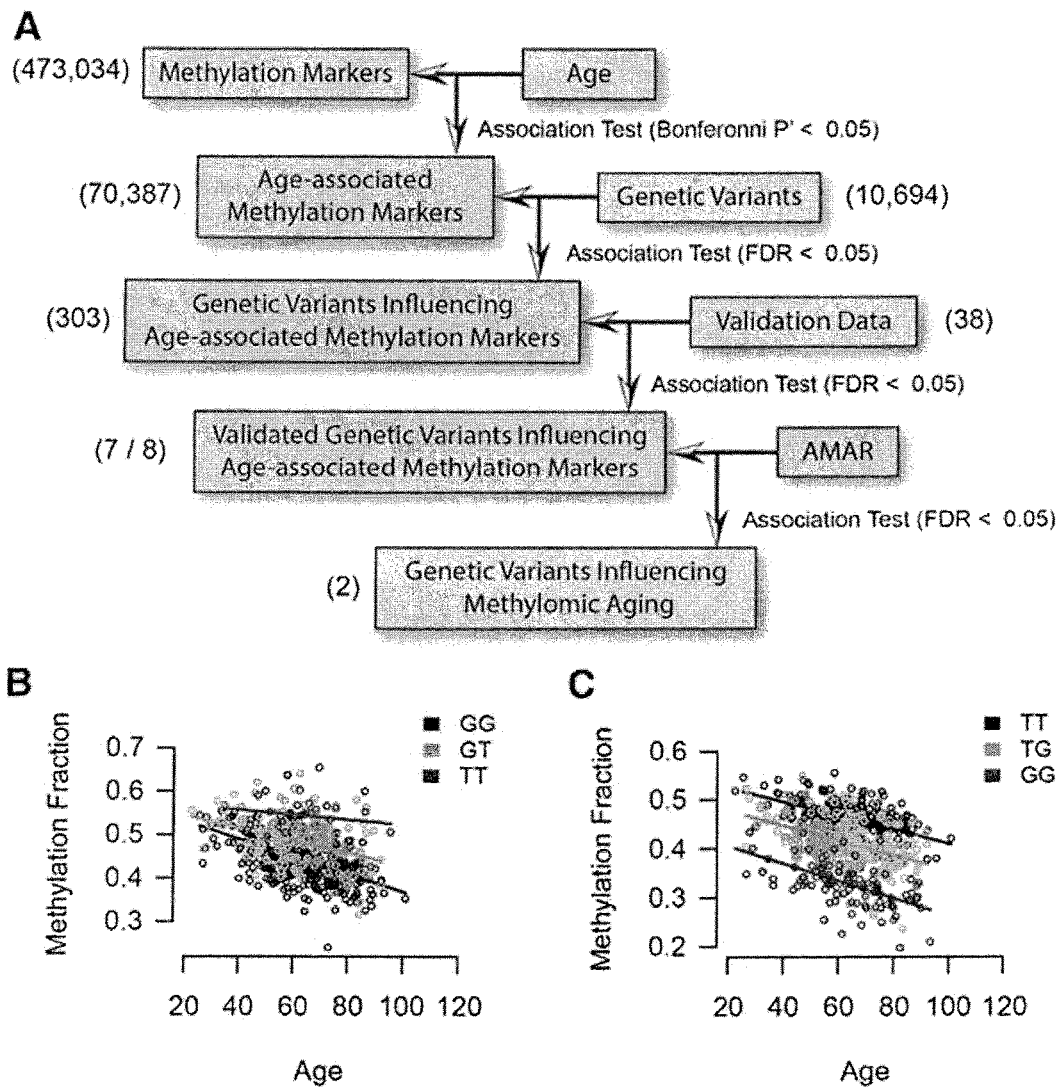
FIG. 3. Genetic Effects on Methylomic Aging. (A) We surveyed genomic variants for an association with age-associated methylation markers. Eight genetic variants, corresponding to 14 meQTLs, were chosen for validation. Of these, seven were significant in the validation cohort and two showed an association with AMAR. (B) A plot of the trend between the methylation marker cg27367526 (STEAP2) and age. The state of variant rs42663 (GTPBP10) causes an offset in this relationship. (C) A second example for cg18404041 and rs2230534 (ITIH1, NEK4). See also Table 4 for a table of confirmed genetic associations.

Table 4, Genetic Variants Influencing Age-Associated Methylation, Related to FIG. 3

A table of the genetic variants which were found to influence age-associated methylation. Distance is the genomic distance from the genetic marker to the methylation marker. Association values are listed as p-values. AMAR association is the significance of the association between the genetic marker and AMAR.

| Genetic Marker | Genetic Genes | Methylation Marker | Methylation Genes | Distance (bp) | Meth-Age Association | Meth-Geno Association | AMAR Association |
|---|---|---|---|---|---|---|---|
| rs2818384 | JAKMIP3 | cg05652533 | DPYSL4, JAKMIP3 | 38793 | $5.86 \times 10^{-9}$ | $3.73 \times 10^{-21}$ | 0.00133 |
| rs42663 | GTPBP10 | cg27367526 | STEAP2 | 142116 | $1.44 \times 10^{-18}$ | $8.05 \times 10^{-22}$ | 0.00476 |
| rs2230534 | ITIH1, NEK4 | cg18404041 | ITIH1, ITIH3, NEK4 | 21881 | $6.78 \times 10^{-14}$ | $1.26 \times 10^{-87}$ | 0.02125 |
| rs17152433 | CTBP2, ZRANB1 | cg07906193 | | 70390 | $8.51 \times 10^{-9}$ | $7.54 \times 10^{-56}$ | 0.05273 |
| rs1058405 | ATF6 | cg19735514 | ATF6 | 10998 | $4.50 \times 10^{-11}$ | $3.87 \times 10^{-63}$ | 0.55546 |
| rs57913893 | ACSS1, C20orf3 | cg26306437 | C20orf3, CST7 | 59756 | $5.20 \times 10^{-8}$ | $5.50 \times 10^{-16}$ | 0.80327 |
| rs6115003 | ACSS1 | cg26306437 | C20orf3, CST7 | 70693 | $5.20 \times 10^{-8}$ | $4.17 \times 10^{-17}$ | 0.92096 |

The methylation marker cg27193080 was one of those found to be significantly associated with age ($p<10^{-17}$), and its methylation fraction was found to be influenced by the single-nucleotide polymorphism (SNP) variant rs140692 ($p<10^{-21}$) (FIG. 3B). This meQTL was particularly interesting as both the SNP and the methylation marker mapped to the gene methyl-CpG binding domain protein 4 (MBD4, with the SNP in an intron and the methylation marker just upstream of the coding region), one of the few known genes encoding a protein that can bind to methylated DNA. This meQTL thus captures a cis relationship in which rs140692 influences the methylation state of MBD4. That MBD4 plays a role in human aging is supported by previous work linking MBD4 to DNA repair, as well as work showing that mutations and knockdowns of MBD4 lead to increased genomic instability (Bellacosa et al., 1999; Bertoni et al., 2009).

Of the seven validated meQTLs, three were identified that had a statistically significant association not only with age but also with aging rate (AMAR, FDR<0.05, FIGS. 3B and 3C). One is the genetic marker rs2230534, which is a synonymous mutation in the gene NEK4, and has a cis association with the methylation marker cg18404041. The NEK family of kinases plays a key role in cell-cycle regulation and cancer (Moniz et al., 2011). The second variant is rs2818384, which is a synonymous mutation in the gene JAKMIP3 and has a cis association with the methylation marker cg05652533. Copy-number variants in JAKMIP3 have been previously associated with glioblastoma (Xiong et al., 2010). The final variant found to influence AMAR is rs42663, which is a missense mutation in the gene GTPBP10 and associates with cg27367526 in the gene STEAP2. STEAP2 is known to play a role in maintaining homeostasis of iron and copper—metals that serve as essential components of the mitochondrial respiratory chain (Ohgami et al., 2006). Studies have shown that perturbations of iron concentrations can induce DNA damage through oxidative stress in mammalian cells (Hartwig and Schlepegrell, 1995; Karthikeyan et al., 2002). These meQTLs represent genetic variants that appear to broadly influence the aging methylome and may be good candidates for further age-associated disease and longevity research.

A Multi-Tissue Diagnostic

Our aging model was derived from whole blood, which is advantageous in the design of practical diagnostics and for testing samples collected from other studies. To investigate whether our aging model was representative of other tissues, we obtained DNA methylation profiles for 368 individuals in the control category of The Cancer Genome Atlas (TCGA) (Collins and Barker, 2007), including 83 breast, 183 kidney, 60 lung, and 42 skin samples. An aging model based on both our primary and validation cohorts demonstrated strong predictive power for chronological age in these samples (expected value R=0.72), although each tissue had a clear linear offset (intercept and slope) from the expectation (FIG. 4A). This offset was consistent within a tissue, even across different batches of the TCGA data. We adjusted for each tissue trend using a simple linear model, producing age predictions with an error comparable to that found in blood (FIG. 4B). Furthermore, predicted AMARs in each tissue supported the effect of men appearing to age more quickly than women ($p<0.05$). Thus, computation of aging rate (AMAR) from blood samples reflects trends that are not specific to blood and may be common throughout many tissues of the human body. Furthermore, this analysis provides evidence that the observed methylomic changes are intrinsic to the methylome and not due primarily to cell heterogeneity, i.e., changing cell-type composition of whole blood with age. In this regard, this study is consistent with a prior analysis of purified CD4+ T cells and CD14+ monocytes, in which the age-associated epigenetic modifications were found to be similar to the changes observed in whole blood (Rakyan et al., 2010).

To investigate the similarities and differences between the tissues, we built age models de novo for breast, kidney, and lung tissues (Table 5; the skin cohort had too few samples to build a model). Most of the markers in the models differed, although all of these models and the primary model share the markers cg23606718 and cg16867657. These markers are both annotated to the gene ELOVL2, which has been linked to the photoaging response in human skin (Kim et al., 2010).

Figure 4:
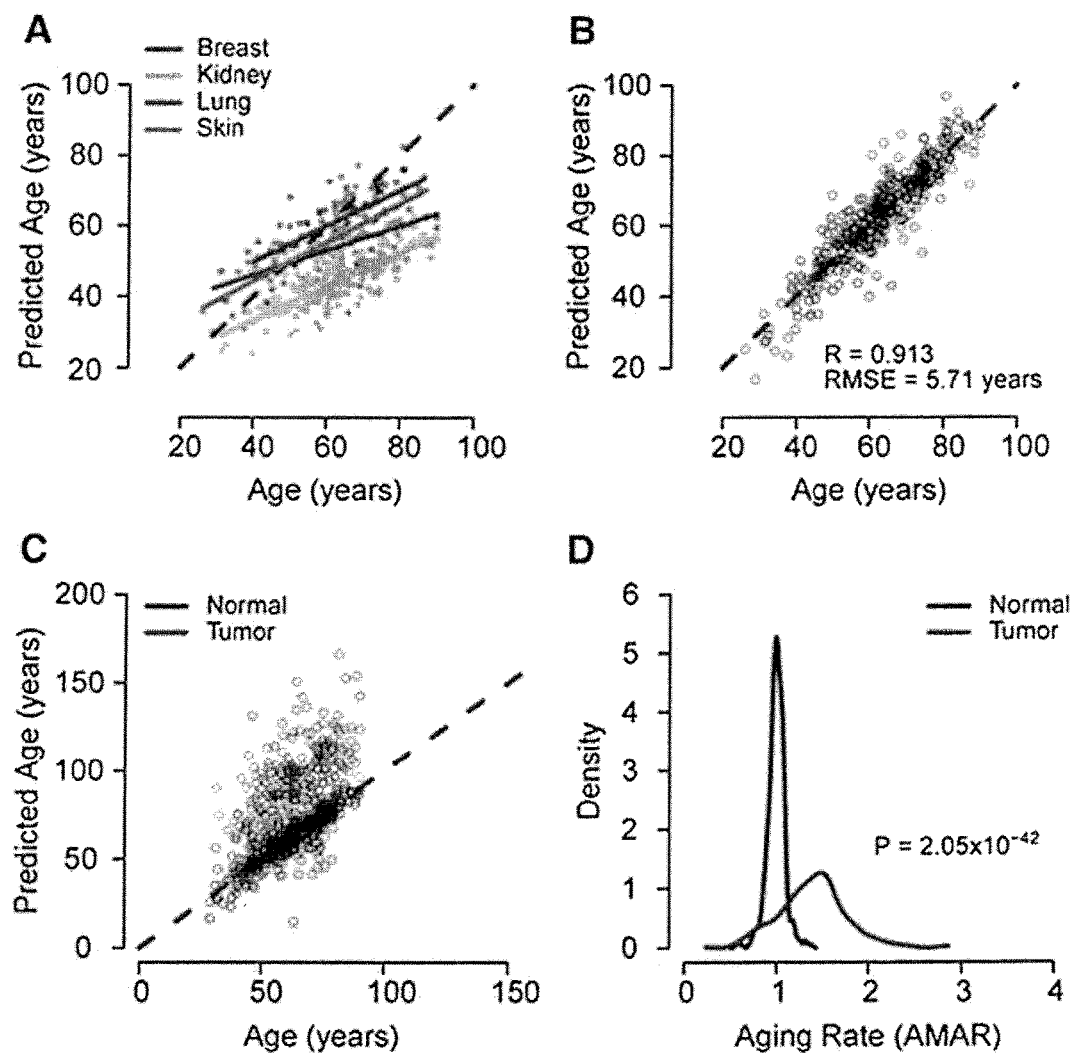
FIG. 4. Multi-Tissue Support. (A) Predictions of age made by the full aging model on the TCGA control samples. There is a high correlation between chronological and predicted age, but each tissue has a different linear intercept and slope. (B) After adjusting the intercept and slope of each tissue, the error of the model is similar to that of the original whole-blood data. Age predictions made on cancer samples are presented in FIG. 11. (C) Age predictions made on matched normal and tumor samples from TCGA. Predictions are adjusted for the linear offset of the parent tissue (breast, kidney, lung, or skin). (D) Tumor samples show a significant increase in AMAR. See also FIG. 13 and Table 5.

Table 5, Aging Model Markers for TCGA Data, Related to FIG. 4

To investigate the similarities and differences between the tissues, we built an age model for breast, kidney, and lung tissues. The skin cohort did not have enough samples to build a model. The markers and coefficients of each model are listed here.

| Marker | Chromosome | Position | Genes | CpG Island | Coefficient |
|---|---|---|---|---|---|
| cg23040782 | 1 | 6762215 | DNAJC11 | No | −7.45 |
| cg11197101 | 1 | 33219998 | KIAA1522 | Yes | 8.73 |
| cg00252781 | 1 | 179334658 | C1orf125, SOAT1 | No | 13.2 |
| cg16909962 | 1 | 229406711 | RAB4A, TMEM78 | Yes | 27.6 |
| cg23606718 | 2 | 131513927 | FAM123C | Yes | 25.1 |
| cg03545227 | 2 | 220173100 | MIR153-1, PTPRN, RESP18 | Yes | 13.5 |
| cg00702638 | 3 | 44803293 | KIAA1143, KIF15 | Yes | 53.1 |
| cg05555455 | 3 | 148804550 | HLTF, Y_RNA.240 | Yes | −18.5 |
| cg03844506 | 4 | 4109441 | | Yes | −7.72 |
| cg16558177 | 4 | 4109446 | | Yes | −2.25 |
| cg11299854 | 5 | 132083184 | CCNI2, KIF3A, SEPT8 | Yes | 43.6 |
| cg05708550 | 5 | 137688227 | CDC25C, FAM53C, KDM3B | Yes | 8.4 |
| cg16867657 | 6 | 11044877 | ELOVL2 | Yes | 23.1 |
| cg22736354 | 6 | 18122719 | NHLRC1, TPMT | Yes | −15 |
| cg14848772 | 6 | 27099813 | HIST1H2AG, HIST1H2AH, HIST1H2BJ, HIST1H2BK, HIST1H4I | No | −14.3 |
| cg15623062 | 6 | 31747133 | Y_RNA.307 | No | 32.2 |
| cg16489193 | 6 | 33240059 | | Yes | 25.5 |
| cg18468088 | 6 | 35490818 | TULP1 | No | 5.96 |
| cg04911280 | 6 | 44281184 | AARS2, TCTE1, TMEM151B | Yes | −9.67 |
| cg19291355 | 6 | 44281188 | AARS2, TCTE1, TMEM151B | Yes | −5.16 |
| cg05917988 | 6 | 44281197 | AARS2, TCTE1, TMEM151B | Yes | 2.77 |
| cg20160885 | 7 | 5013524 | MMD2, RBAK, RNF216L | Yes | 49.6 |
| cg19230755 | 7 | 65878503 | GS1-124K5.2, GS1-124K5.6, NCRNA00174, SKP1P1, TPST1, U6.862 | Yes | −2.26 |
| cg09941452 | 7 | 97557827 | | Yes | −14.2 |
| cg26830108 | 7 | 100813299 | AP1S1, C7orf52, VGF | No | 1.22 |
| cg19273773 | 7 | 102790112 | NAPEPLD | Yes | 1.56 |

-continued

| Marker | Chromosome | Position | Genes | CpG Island | Coefficient |
|---|---|---|---|---|---|
| cg14361627 | 7 | 130419116 | KLF14 | Yes | 1.17 |
| cg08097417 | 7 | 130419133 | KLF14 | Yes | 53.5 |
| cg02821342 | 7 | 130793551 | MKLN1 | No | −19.8 |
| cg07392449 | 8 | 11324666 | FAM167A | Yes | 73 |
| cg08318076 | 8 | 62051812 | CLVS1 | Yes | 13 |
| cg02560186 | 11 | 3602584 | OR7E117P | Yes | 27.8 |
| cg08715791 | 11 | 66189297 | MRPL11, NPAS4, SNORA43.2 | Yes | −30.6 |
| cg23156348 | 11 | 124981869 | TMEM218 | No | −21.1 |
| cg10820926 | 14 | 30397408 | PRKD1 | Yes | 19.2 |
| cg06121469 | 15 | 44956098 | PATL2, SPG11 | No | −0.156 |
| cg07477282 | 15 | 44956107 | PATL2, SPG11 | No | 2.22 |
| cg21801378 | 15 | 72612125 | CELF6 | Yes | −49.5 |
| cg02331561 | 16 | 2391081 | ABCA17P, ABCA3 | Yes | −17 |
| cg06144905 | 17 | 27369780 | PIPOX | No | 9.13 |
| cg14692377 | 17 | 28562685 | BLMH, SLC6A4, SNORD63.3 | Yes | 13.7 |
| cg18569335 | 17 | 40171970 | DNAJC7, NKIRAS2, ZNF385C | Yes | −30.6 |
| cg26147554 | 18 | 712733 | ENOSF1, YES1 | Yes | 17.7 |
| cg21927946 | 19 | 4769688 | C19orf30, MIR7-3 | No | 73.4 |
| cg15789607 | 19 | 4769690 | C19orf30, MIR7-3 | No | −15.4 |
| cg12589298 | 19 | 50828905 | KCNC3, MYH14, NAPSB | Yes | 15.3 |
| cg06458239 | 19 | 58038573 | MIR1274B, ZNF549, ZNF550, ZNF773 | Yes | 22.4 |
| cg10729426 | 19 | 58038585 | MIR1274B, ZNF549, ZNF550, ZNF773 | Yes | 13.5 |
| cg26734668 | 19 | 58111094 | ZIK1, ZNF134, ZNF530 | No | 9.2 |
| cg22888484 | 20 | 37075185 | SNHG11, SNORA39, SNORA60, SNORA71.3, SNORA71A, SNORA71C, SNORA71D | No | 201 |

The TCGA data set also contains methylome profiles representing a total of 319 tumors and matched normal tissue samples (breast, kidney, lung, and skin). Interestingly, use of our aging model indicated that tumors appear to have aged 40% more than matched normal tissue from the same individual (Wilcox test, $p<10^{-41}$, FIGS. 4C and 4D). Accelerated tumor aging was apparent regardless of the primary tissue type. We investigated whether this was the result of broad shifts in global methylation levels by examining all 70,387 age-associated markers, of which 44% tend to increase and 56% tend to decrease with age. Methylation fraction values in matched tumor and normal samples supported the finding that tumors coincide with older values for 74% of the markers regardless of the trending direction (binomial p~0). Furthermore, separate aging models built in the matched normal and tumor samples confirm the apparent aging effect (FIG. 13).

Different Aging Rates Lead to Divergent Methylomes

Figure 5:
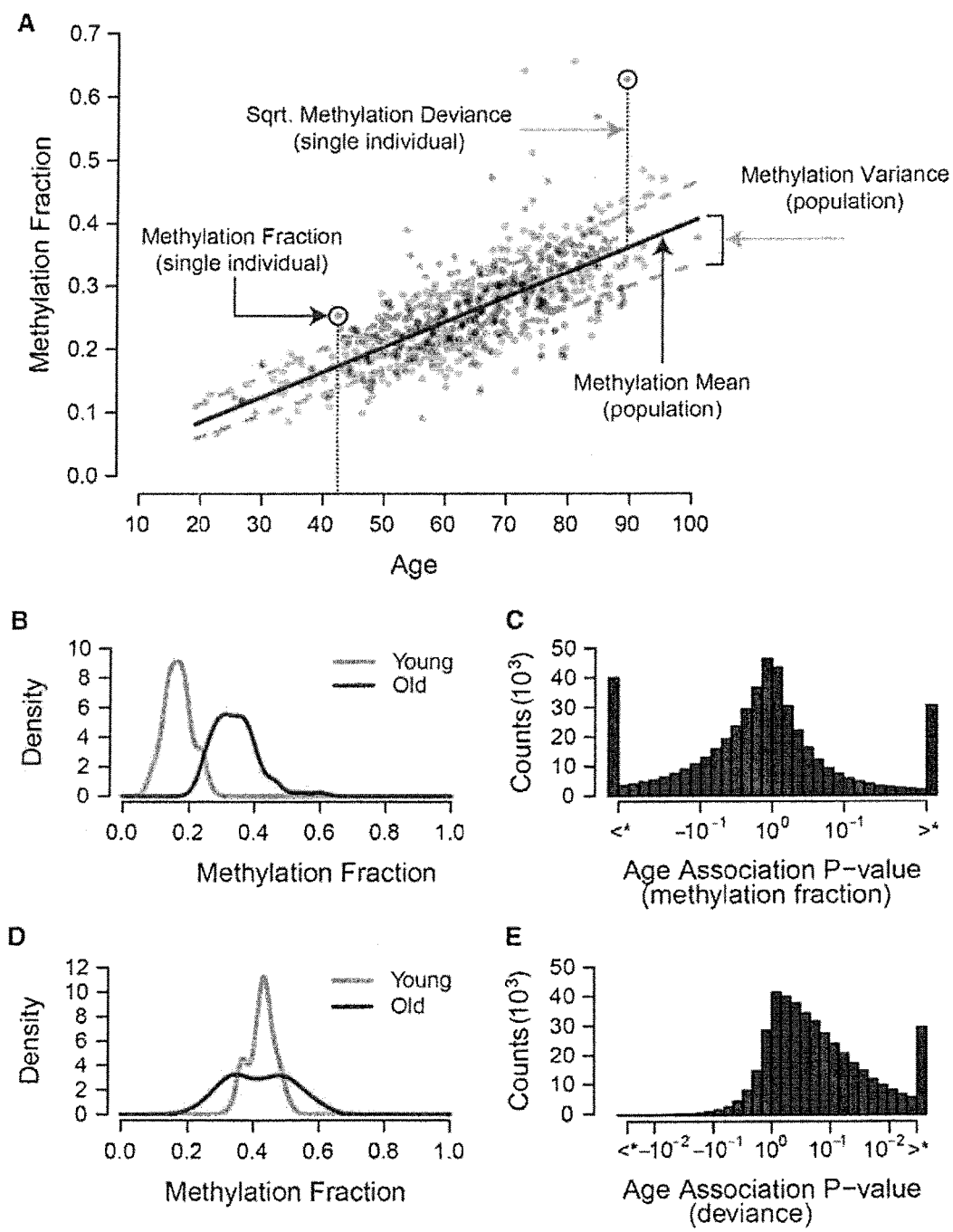
FIG. 5. Age Associations for Methylation. Fraction and Deviance (A) Methylation fraction values for are shown for the marker cg24724428. Over any subset of the cohort, we consider two group methylation statistics: the mean and variance. Marker variance is a measure of the mean methylation deviance, which is defined as the squared difference between an individual's methylation fraction and their expected methylation fraction. (B) A density plot showing the change in mean methylation with age for the marker cg24724428. Young and old groups are based on the top and bottom 10%. (C) A histogram of the significance of association between the methylation fraction of all markers and age. p values are signed such that positive values represent an increase of methylation with age. Markers that exceeded the FDR<0.05 threshold are grouped into the most extreme bins. (D) A density plot showing the change in methylation deviance with age for the marker cg24724428. (E) A histogram, in the same form as (D), of the significance of association between the methylation deviance of all markers and age. Aging trends are mapped for CpG islands in FIG. 12. See also FIG. 14.

If individuals indeed age at different rates, it might be expected that their individual methylomes should diverge over time. This is based on the premise that the methylomes of the very young share certain similarities and that these similarities diminish as individuals accumulate changes over time. This effect, called epigenetic drift, has been observed in monozygotic twins (Fraga et al., 2005), but few specific hypothesis have been put forth to account for it. To examine epigenetic drift in our samples, we computed the deviance of each methylation marker value as its squared distance from the expected population mean (FIG. 5A). Then, in addition to testing for markers whose methylation fraction changes with age (FIGS. 5B and 5C), we were able to test for markers whose deviance changes with age (FIGS. 5D and 5E) (Breusch and Pagan, 1979). Increasing deviance was a widespread phenomenon—we identified 27,800 markers for which the deviance was significantly associated with age (FDR<0.05), of which 27,737 (99.8%) represented increased rather than decreased deviance (FIGS. 5E and 5). For any given individual, especially high or low methylome deviance was a strong predictor of aging rate (R=0.47, p~0), suggesting that differences in aging rates account for part of methylome heterogeneity and epigenetic drift.

Figure 6:
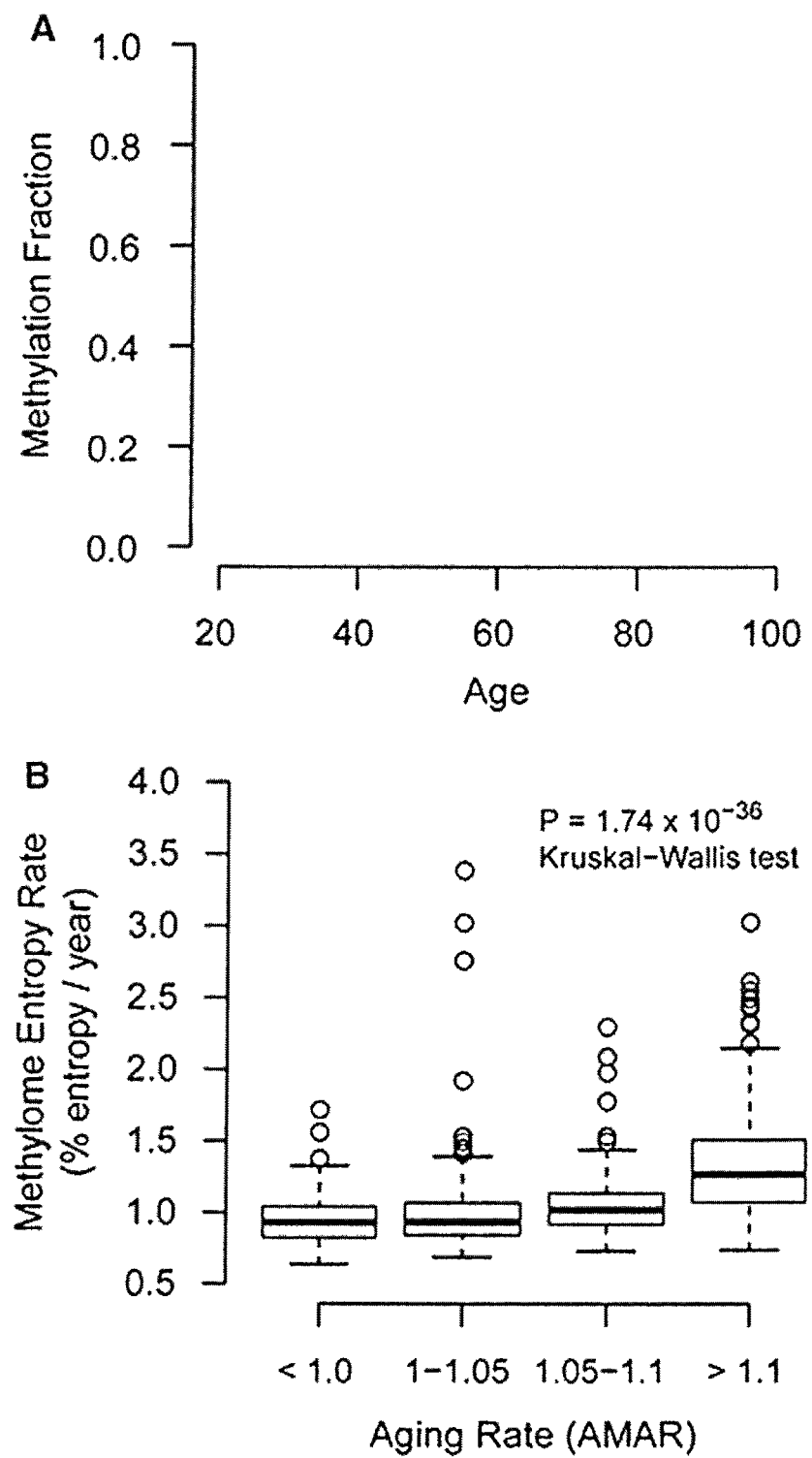
FIG. 6. Methylome-wide Trends with Age. (A) Aggregate regression lines for all methylation markers that increased with age (red) and decreased with age (blue). The darkest color represents the median regression line and the bounds represent the 25% and 75% quantile. Both increasing and decreasing markers trend toward moderate methylation fraction values. (B) An entropy aging rate was calculated as the mean Shannon entropy of age-associated methylation markers divided by chronological age. This was strongly associated with AMAR.

Another way to examine epigenetic drift is in terms of Shannon entropy, or loss of information content in the methylome over time (Shannon and Weaver, 1963). An increase in entropy of a CpG marker means that its methylation state becomes less predictable across the population of cells, i.e., its methylation fraction tends toward 50%. Indeed, over all markers associated with a change in methylation fraction in the sample cohort, 70% tended toward a methylation fraction of 50% (FIG. 6A, binomial p~0, Table 2). Consequently, we observed a highly significant increase in methylome entropy over the sample cohort (R=0.21, $p<10^{-7}$). Furthermore, extreme methylome entropy for an individual was highly correlated with accelerated aging rate based on AMAR (R=0.49, p~0, FIG. 6B).

Aging Rates and the Transcriptome

As changes in methylation have been directly linked to changes in gene expression (Sun et al., 2011), we were interested in whether these changes in the aging methylome were mirrored on a functional level in the human transcriptome and reflected differences in aging rates. For this purpose, we obtained and analyzed publicly available gene expression profiles from the whole blood of 488 individuals spanning an age range of 20 to 75 (Emilsson et al., 2008). We found strong evidence for genes whose expression associates with age (326 genes, FDR<0.05) and for genes with increasing expression deviance (binomial $p<10^{-276}$). Strikingly, we found that genes with age-associated expression profiles were more likely to have nearby age-associated methylation markers in our data (p<0.01, Table 6). We used this information to build a model of aging based on the expression of genes that were associated with age in the methylome (FIG. 7A, Table 7). This model demonstrated a clear ability to measure aging rate using expression data, reproducing our finding of increased aging rates for men as compared to women (FIG. 7B, 11% difference, $p<10^{-4}$). The gender effect was not present in a model built using all available genes rather than those associated with age-related changes in the methylome (p>0.05). Thus, age-associated changes to the methylome are indicative of functional changes in gene expression patterns.

Figure 7:
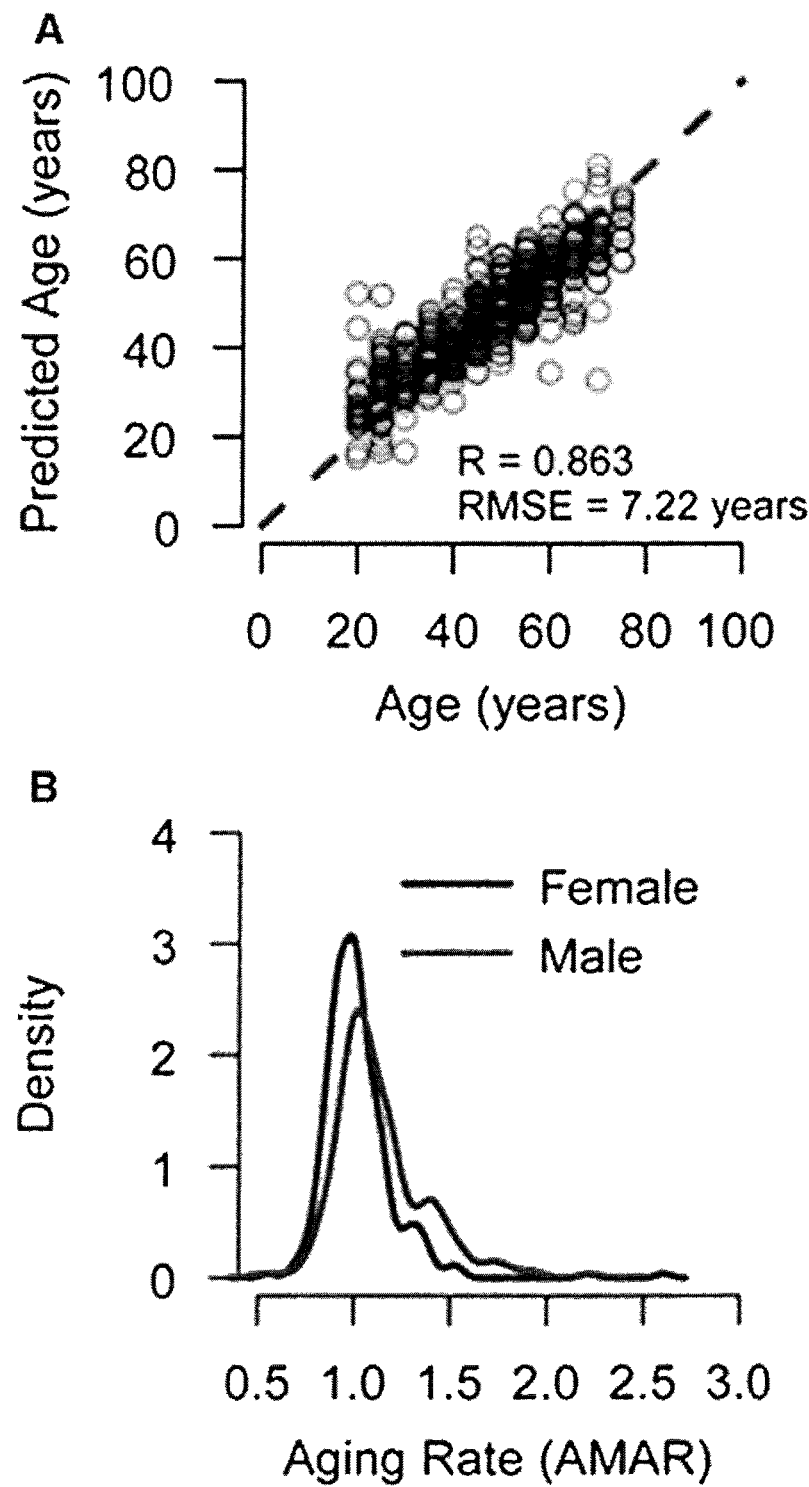
FIG. 7. Transcription Aging Model. (A) We built an aging model using mRNA expression data for genes that showed an aging trend in the methylome. Its standard error (RMSE=7.22 years) is increased due to the rounding of ages to the nearest 5 year interval in the data set. (B) Similar to the methylome, the transcriptome shows an increased aging rate for men as compared to women ($p<10^4$). See also Table 6 and Table 7.
Figure 8:
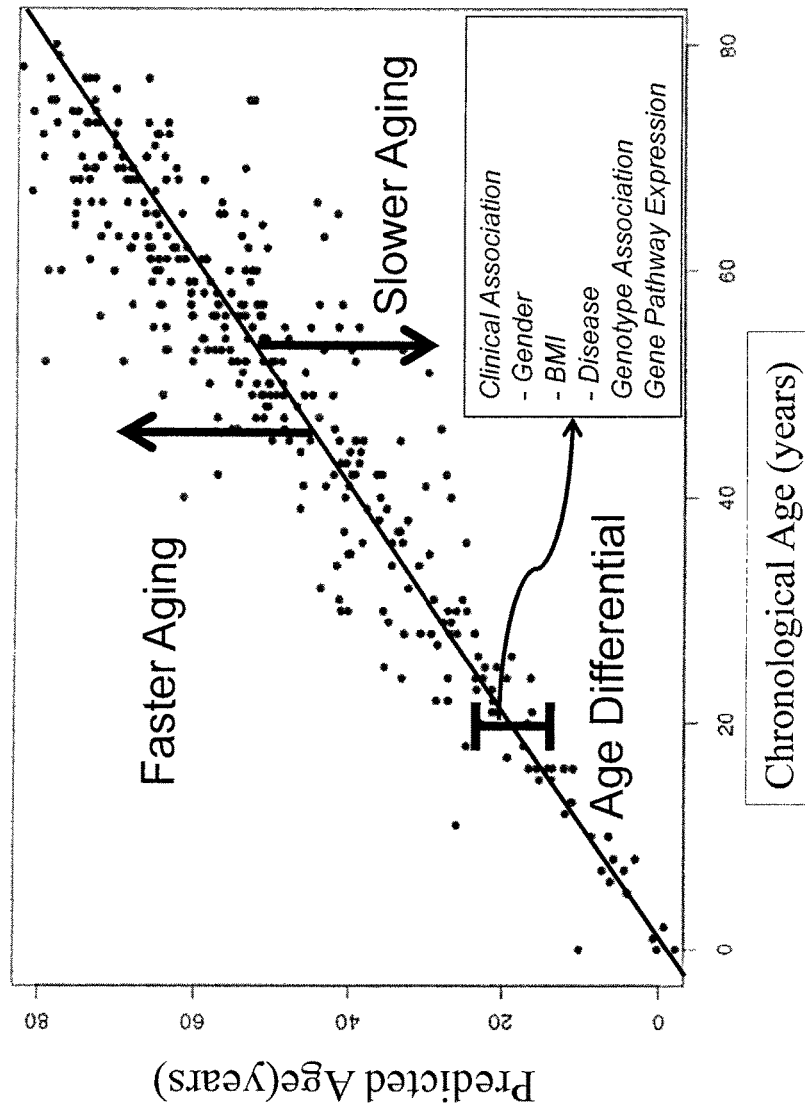
FIG. 8 shows the model of biological age.

Table 6, Genes Associated with Aging in Both the Methylome and the Transcriptome, Related to FIG. 7

A list of genes which mapped to age-associated methylation markers and showed age-associated changes the transcriptome.

ABCA3
ABCB9
ABLIM1
ACAA2
ACCN2
ACSF2
ACVR2A
AEBP1
AGBL2
AGPAT4
AK5
ALDH5A1
ANKRD13B
ANKS6
ANXA1
APBA2
APBB1
APOBEC3H
ARAP2
ARHGEF4
ATP1B1
B3GAT1
BACH2
BATF3
BCAS4
BCL7A
BCL9
BDH1
BFSP1
BHLHE40
BLNK
BYSL
C10orf128
C12orf23
C16orf45
C17orf58
C1orf172
C1orf21
C1orf216
C1orf51
C21orf63
C2orf40
C6orf97
CACHD1
CACNA2D2
CALHM2
CAMK2N1
CAPN2
CCDC106
CCR10
CCR7
CD200
CD244
CD8B
CD9
CDCA7L
CDKN1C
CEBPG
CECR5
CENPE
CENPV
CHMP7
CHSY3
CAPIN1
CISH
CMC1
COBLL1
COL5A3
CR2
CRIP1
CRTAM
CRTC3
CSF1R
CST7

-continued

CTLA4
CTNNA1
CTSL1
CX3CR1
CYP2J2
CYP4F12
DCBLD2
DDB2
DEFA4
DENND2D
DEPDC7
DGKA
DLL1
DNASE1L3
DNMT3A
DNMT3B
DPH5
DUSP4
DYNLL1
ECT2
EDAR
EEF1G
EFNA1
EOMES
EPHA1
EPHA2
EPHX2
EPPK1
EXPH5
FAIM3
FAM129C
FAM134B
FAM13A
FAN1
FASLG
FBL
FBLN2
FBXO24
FCGBP
FGFBP2
FGFRL1
FLNB
FOXP1
FZD1
GAL3ST4
GATA3
GFI1
GLT25D2
GNG7
GPC2
GPR114
GPR137B
GPR153
GPR56
GSC
GTSF1
GYG1
GZMH
HEXIM1
HIST1H3D
HOPX
IGFBP7
IGLL1
IL10RA
IL16
IL4I1
IL7R
INPP4B
IRS1
ITFG2
ITGA6
ITM2C
JAKMIP1
KAT2A
KATNAL1
KCNMB4
KIAA1841
KLF4
KLF6

-continued

KLHL14
KLHL3
KLRG1
LAMA5
LBH
LDLRAP1
LEF1
LGALS1
LILRA4
LIMS2
LMO7
LPCAT1
LRP11
LRRC32
LTK
MAN1C1
MB21D2
MEOX1
MEST
MLF1
MPI
MS4A3
MS4A4A
MT1E
MT1M
MTSS1
MTUS1
MXRA8
MYC
MYO6
MYOF
NBEA
NCAPH
NEFH
NELL2
NHLRC1
NKG7
NMT2
NMUR1
NOB1
NOP16
NOSIP
NPM3
NRCAM
NSUN5
NT5E
NTAN1
NUAK1
OSBPL10
OXNAD1
P2RX5
PACSIN1
PALLD
PAQR4
PCBP4
PCDH12
PCSK4
PCSK5
PDE6B
PDE7A
PDE9A
PDGFD
PDGFRB
PELI3
PHGDH
PHLDA3
PHYHD1
PI16
PIK3IP1
PLAG1
PLCG1
PLEKHA7
PLXDC1
PMEPA1
PMP22
POMC
POU2AF1
PPAP2C
PPM1J

-continued

PPP2R2B
PRR5L
PRSS23
PRSS35
PTGDS
PTGER2
PTPRK
PTTG1
PUS1
PYROXD1
RAB15
RAB27B
RAB6B
RAB6C
RAD54B
RAMP1
RAPGEF6
RASD1
RASGEF1A
RGMA
RGS9
RHOC
RNASE2
RNASE3
RNF144A
ROBO1
RPL13
RUNX3
S100A10
S1PR5
SATB1
SCARB1
SEC14L2
SEMA3G
SFRP5
SFTPD
SIRPG
SLAMF7
SLC1A7
SLC23A1
SLC27A5
SLC2A6
SLC45A3
SOCS2
SORC53
SOX15
SPEG
SPIB
SPINK2
SPN
STOM
STX8
SUSD1
SYT11
TARBP1
TBX21
TCAP
TCF3
TCF4
TCF7
TCF7L2
TGFBR3
TIGIT
TM6SF1
TMEM121
TMEM8B
TMIGD2
TNFRSF17
TNFRSF25
TPPP3
TRAF5
TRAP1
TRIM2
TSPAN13
TSPAN2
TWIST1
TXNDC5
USP18
VCAM1

-continued

VIT
WARS
ZBED3
ZFYVE28
ZNF135
ZNF167
ZNF177
ZNF263
ZNF285
ZNF365
ZNF462
ZNF528
ZNF544
ZNF551
ZSCAN18

Table 7, Transcriptome Aging Model, Related to FIG. 7
The list of genes and coefficients used for predicting age based on transcriptome data.

| Gene | Coefficient |
|---|---|
| ABLIM1 | −4.537363687 |
| ACCN2 | −4.021935755 |
| ACVR2A | 5.862922173 |
| AK5 | −10.29726151 |
| ANXA1 | 6.307730249 |
| ASNS | 23.66865779 |
| AUTS2 | −13.3985662 |
| C16orf45 | 4.553248948 |
| CACHD1 | −7.768187189 |
| CDKN1C | −0.0105012 |
| CENPV | −2.462314825 |
| CMC1 | 8.866490009 |
| CR2 | −1.78645877 |
| CRIP1 | 4.33558575 |
| EFNA1 | −5.741766145 |
| EPHA2 | 2.917895917 |
| FAIM3 | 1.019538625 |
| FBLN2 | −2.061520114 |
| FLNB | −3.844863485 |
| FZD1 | 1.375051746 |
| GPC2 | −7.431385678 |
| GSC | 4.904090057 |
| GTSF1 | 12.58953522 |
| HIST1H3D | −8.692565907 |
| IGLL1 | −4.235566899 |
| KRT72 | 2.814127932 |
| LRP11 | 5.664133584 |
| MEOX1 | 13.8516364 |
| MS4A3 | −2.661573104 |
| NEFH | −6.728594491 |
| NMT2 | −15.38338708 |
| NOSIP | −13.61680769 |
| NT5E | −1.994658678 |
| PHLDA3 | 18.71229769 |
| PHYHD1 | −5.052538719 |
| PLXDC1 | −5.337661458 |
| POMC | −6.100365433 |
| PRSS35 | −6.498528559 |
| PTGER2 | −8.407414661 |
| PYROXD1 | 13.70056157 |
| RGMA | 5.458322024 |
| ROBO1 | −7.342718162 |
| SEC14L2 | −2.887682148 |
| SFRP5 | 4.430923586 |
| SLC45A3 | 8.799140451 |
| SORCS3 | 9.998064269 |
| SPEG | 0.574659287 |
| SPINK2 | 0.302316458 |
| SYT11 | 7.093819787 |
| TMEM8B | −13.0069907 |
| TM1GD2 | 6.006761191 |
| TNFRSF17 | −6.154501401 |
| TXNDC5 | −0.265342977 |
| ZNF285 | −4.729710661 |

CONCLUSIONS

In this study, we have shown that genome-wide methylation patterns represent a strong and reproducible biomarker of biological aging rate. These patterns enable a quantitative model of the aging methylome that demonstrates high accuracy and an ability to discriminate relevant factors in aging, including gender and genetic variants. Moreover, our ability to apply this model in multiple tissues suggests the possibility of a common molecular clock, regulated in part by changes in the methylome. It remains to be seen whether these changes occur on an intracellular level uniformly across a population of cells, or reflect consistent changes in tissue composition over time.

The ability to predict age from whole blood may permit a wider analysis in longitudinal studies such as the Framingham Study, the Women's Health Initiative, blood samples collected on neonatal Guthrie cards, and other longitudinal studies with rich annotation of biometric and disease traits. Aging trends could emerge from such studies with many potential practical implications, from health assessment and prevention of disease to forensic analysis. Similar to the effect of gender in this study, the identification of additional biometric or environmental factors that influence AMAR, such as smoking, alcohol consumption, or diet, will permit quantitative assessments of their impacts on health and longevity. A useful example would be to periodically assess the rate of aging of an individual using AMAR and determine whether diet or environmental factors can accelerate or retard the aging process and diseases such as age related macular degeneration. As models of human aging improve, it is conceivable that biological age, as measured from molecular profiles, might one day supersede chronological age in the clinical evaluation and treatment of patients.

REFERENCES FOR EXAMPLE 1

Alisch, R. S., Barwick, B. G., Chopra, P., Myrick, L. K., Satten, G. A., Conneely, K. N., and Warren, S. T. (2012). Age-associated DNA methylation in pediatric populations. Genome Res. 22, 623-632.

Atzmon, G., Rincon, M., Schechter, C. B., Shuldiner, A. R., Lipton, R. B., Bergman, A., and Barzilai, N. (2006). Lipoprotein genotype and conserved pathway for exceptional longevity in humans. PLoS Biol. 4, e113.

Austad, S. N. (2006). Why women live longer than men: sex differences in longevity. Gend. Med. 3, 79-92.

Barres, R., and Zierath, J. R. (2011). DNA methylation in metabolic disorders. Am. J. Clin. Nutr. 93, 897S-900.

Bell, J. T., Pai, A. A., Pickrell, J. K., Gaffney, D. J., Pique-Regi, R., Degner, J. F., Gilad, Y., and Pritchard, J. K. (2011). DNA methylation patterns associate with genetic and gene expression variation in HapMap cell lines. Genome Biol. 12, R10. http://www.ncbi.nlm.nih-.gov/pubmed/21251332.

Bell, J. T., Tsai, P.-C., Yang, T.-P., Pidsley, R., Nisbet, J., Glass, D., Mangino, M., Zhai, G., Zhang, F., Valdes, A., et al.; MuTHER Consortium. (2012). Epigenome-wide scans identify differentially methylated regions for age and age-related phenotypes in a healthy ageing population. PLoS Genet. 8, e1002629.

Bellacosa, A., Cicchillitti, L., Schepis, F., Riccio, A., Yeung, A. T., Matsumoto, Y., Golemis, E. A., Genuardi, M., and Neri, G. (1999). MED1, a novel human methyl-CpG-binding endonuclease, interacts with DNA mismatch repair protein MLH1. Proc. Natl. Acad. Sci. USA 96, 3969-3974.

Benjamini, Y., and Hochberg, Y. (1995). Controlling the False Discovery Rate: A Practical and Powerful Approach to Multiple Testing. J. R. Stat. Soc. B 57, 289-300.

Bertoni, C., Rustagi, A., and Rando, T. A. (2009). Enhanced gene repair mediated by methyl-CpG-modified single-stranded oligonucleotides. Nucleic Acids Res. 37, 7468-7482.

Bibikova, M., Barnes, B., Tsan, C., Ho, V., Klotzle, B., Le, J. M., Delano, D., Zhang, L., Schroth, G. P., Gunderson, K. L., et al. (2011). High density DNA methylation array with single CpG site resolution. Genomics 98, 288-295.

Blair, S. N., Kohl, H. W., 3rd, Paffenbarger, R. S. J., Jr., Clark, D. G., Cooper, K. H., and Gibbons, L. W. (1989). Physical fitness and all-cause mortality. A prospective study of healthy men and women. JAMA 262, 2395-2401.

Bocklandt, S., Lin, W., Sehl, M. E., Sanchez, F. J., Sinsheimer, J. S., Horvath, S., and Vilain, E. (2011). Epigenetic predictor of age. PLoS ONE 6, e14821.

Boks, M. P., Derks, E. M., Weisenberger, D. J., Strengman, E., Janson, E., Sommer, I. E., Kahn, R. S., and Ophoff, R. A. (2009). The relationship of DNA methylation with age, gender and genotype in twins and healthy controls. PLoS ONE 4, e6767.

Bollati, V., Schwartz, J., Wright, R., Litonjua, A., Tarantini, L., Suh, H., Sparrow, D., Vokonas, P., and Baccarelli, A. (2009). Decline in genomic DNA methylation through aging in a cohort of elderly subjects. Mech. Ageing Dev. 130, 234-239.

Breusch, T. S., and Pagan, A. R. (1979). A Simple Test for Heteroscedasticity and Random Coefficient Variation. Econometrica 47, 1287.

Christensen, B. C., Houseman, E. A., Marsit, C. J., Zheng, S., Wrensch, M. R., Wiemels, J. L., Nelson, H. H., Karagas, M. R., Padbury, J. F., Bueno, R., et al. (2009). Aging and environmental exposures alter tissue-specific DNA methylation dependent upon CpG island context. PLoS Genet. 5, e1000602.

Collins, F. S., and Barker, A. D. (2007). Mapping the cancer genome. Pinpointing the genes involved in cancer will help chart a new course across the complex landscape of human malignancies. Sci. Am. 296, 50-57.

de Magalhães, J. P., Curado, J., and Church, G. M. (2009). Meta-analysis of age-related gene expression profiles identifies common signatures of aging. Bioinformatics 25, 875-881.

Emilsson, V., Thorleifsson, G., Zhang, B., Leonardson, A. S., Zink, F., Zhu, J., Carlson, S., Helgason, A., Walters, G. B., Gunnarsdottir, S., et al. (2008). Genetics of gene expression and its effect on disease. Nature 452, 423-428.

Epel, E. S., Blackburn, E. H., Lin, J., Dhabhar, F. S., Adler, N. E., Morrow, J. D., and Cawthon, R. M. (2004). Accelerated telomere shortening in response to life stress. Proc. Natl. Acad. Sci. USA 101, 17312-17315.

Esteller, M. (2008). Epigenetics in cancer. N. Engl. J. Med. 358, 1148-1159.

Feinberg, A. P., Irizarry, R. A., Fradin, D., Aryee, M. J., Murakami, P., Aspelund, T., Eiriksdottir, G., Harris, T. B., Launer, L., Gudnason, V., and Fallin, M. D. (2010). Personalized epigenomic signatures that are stable over time and covary with body mass index. Sci. Transl. Med. 2, 49ra67.

Fraga, M. F., and Esteller, M. (2007). Epigenetics and aging: the targets and the marks. Trends Genet. 23, 413-418.

Fraga, M. F., Ballestar, E., Paz, M. F., Ropero, S., Setien, F., Ballestar, M. L., Heine-Suñer, D., Cigudosa, J. C., Urioste, M., Benitez, J., et al. (2005). Epigenetic differences arise during the lifetime of monozygotic twins. Proc. Natl. Acad. Sci. USA 102, 10604-10609.

Fraser, H. B., Khaitovich, P., Plotkin, J. B., Pääbo, S., and Eisen, M. B. (2005). Aging and gene expression in the primate brain. PLoS Biol. 3, e274.

Friedman, J., Hastie, T., and Tibshirani, R. (2010). Regularization Paths for Generalized Linear Models via Coordinate Descent. J. Stat. Softw. 33, 1-22.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol. 5, R80.

Harley, C. B., Futcher, A. B., and Greider, C. W. (1990). Telomeres shorten during ageing of human fibroblasts. Nature 345, 458-460.

Hartwig, A., and Schlepegrell, R. (1995). Induction of oxidative DNA damage by ferric iron in mammalian cells. Carcinogenesis 16, 3009-3013.

Heyn, H., Li, N., Ferreira, H. J., Moran, S., Pisano, D. G., Gomez, A., Diez, J., Sanchez-Mut, J. V., Setien, F., Carmona, F. J., et al. (2012). Distinct DNA methylomes of newborns and centenarians. Proc. Natl. Acad. Sci. USA 109, 10522-10527.

Jones, P. A., and Laird, P. W. (1999). Cancer epigenetics comes of age. Nat. Genet. 21, 163-167. Karthikeyan, G., Lewis, L. K., and Resnick, M. A. (2002). The mitochondrial protein frataxin prevents nuclear damage. Hum. Mol. Genet. 11, 1351-1362.

Kim, E. J., Kim, M.-K., Jin, X.-J., Oh, J.-H., Kim, J. E., and Chung, J. H. (2010). Skin aging and photoaging alter fatty acids composition, including 11,14,17-eicosatrienoic acid, in the epidermis of human skin. J. Korean Med. Sci. 25, 980-983.

Lane, M. A., Baer, D. J., Rumpler, W. V., Weindruch, R., Ingram, D. K., Tilmont, E. M., Cutler, R. G., and Roth, G. S. (1996). Calorie restriction lowers body temperature in rhesus monkeys, consistent with a postulated anti-aging mechanism in rodents. Proc. Natl. Acad. Sci. USA 93, 4159-4164.

Li, R., Li, Y., Kristiansen, K., and Wang, J. (2008). SOAP: short oligonucleotide alignment program. Bioinformatics 24, 713-714.

Moniz, L., Dutt, P., Haider, N., and Stambolic, V. (2011). Nek family of kinases in cell cycle, checkpoint control and cancer. Cell Div. 6, 18.

Murgatroyd, C., Patchev, A. V., Wu, Y., Micale, V., Bockmühl, Y., Fischer, D., Holsboer, F., Wotjak, C. T., Almeida, O. F. X., and Spengler, D. (2009). Dynamic DNA methylation programs persistent adverse effects of early-life stress. Nat. Neurosci. 12, 1559-1566.

Ohgami, R. S., Campagna, D. R., McDonald, A., and Fleming, M. D. (2006). The Steap proteins are metalloreductases. Blood 108, 1388-1394.

Rakyan, V. K., Down, T. A., Maslau, S., Andrew, T., Yang, T.-P., Beyan, H., Whittaker, P., McCann, O. T., Finer, S., Valdes, A. M., et al. (2010). Human aging-associated DNA hypermethylation occurs preferentially at bivalent chromatin domains. Genome Res. 20, 434-439.

Saito, T., Iwata, N., Tsubuki, S., Takaki, Y., Takano, J., Huang, S.-M., Suemoto, T., Higuchi, M., and Saido, T. C. (2005). Somatostatin regulates brain amyloid beta peptide Abeta42 through modulation of proteolytic degradation. Nat. Med. 11, 434-439.

Shannon, C. E., and Weaver, W. (1963). The Mathematical Theory of Communication (Champaign, Ill.: University of Illinois Press).

Small, K. S., Hedman, A. K., Grundberg, E., Nica, A. C., Thorleifsson, G., Kong, A., Thorsteindottir, U., Shin, S.-Y., Richards, H. B., Soranzo, N., et al.; GIANT Consortium; MAGIC Investigators; DIAGRAM Consortium; MuTHER Consortium. (2011). Identification of an imprinted master trans regulator at the KLF14 locus related to multiple metabolic phenotypes. Nat. Genet. 43, 561-564.

Suh, Y., Atzmon, G., Cho, M.-O., Hwang, D., Liu, B., Leahy, D. J., Barzilai, N., and Cohen, P. (2008). Functionally significant insulin-like growth factor I receptor mutations in centenarians. Proc. Natl. Acad. Sci. USA 105, 3438-3442.

Sun, Z., Asmann, Y. W., Kalari, K. R., Bot, B., Eckel-Passow, J. E., Baker, T. R., Carr, J. M., Khrebtukova, I., Luo, S., Zhang, L., et al. (2011). Integrated analysis of gene expression, CpG island methylation, and gene copy number in breast cancer cells by deep sequencing. PLoS ONE 6, e17490.

Tatar, M., Bartke, A., and Antebi, A. (2003). The endocrine regulation of aging by insulin-like signals. Science 299, 1346-1351.

Troyanskaya, O., Cantor, M., Sherlock, G., Brown, P., Hastie, T., Tibshirani, R., Botstein, D., and Altman, R. B. (2001). Missing value estimation methods for DNA microarrays. Bioinformatics 17, 520-525.

Valdes, A. M., Andrew, T., Gardner, J. P., Kimura, M., Oelsner, E., Cherkas, L. F., Aviv, A., and Spector, T. D. (2005). Obesity, cigarette smoking, and telomere length in women. Lancet 366, 662-664.

Vijg, J., and Campisi, J. (2008). Puzzles, promises and a cure for ageing. Nature 454, 1065-1071.

Wheeler, H. E., Metter, E. J., Tanaka, T., Absher, D., Higgins, J., Zahn, J. M., Wilhelmy, J., Davis, R. W., Singleton, A., Myers, R. M., et al. (2009). Sequential use of transcriptional profiling, expression quantitative trait mapping, and gene association implicates MMP20 in human kidney aging. PLoS Genet. 5, e1000685.

Willcox, B. J., Donlon, T. A., He, Q., Chen, R., Grove, J. S., Yano, K., Masaki, K. H., Willcox, D. C., Rodriguez, B., and Curb, J. D. (2008). FOXO3A genotype is strongly associated with human longevity. Proc. Natl. Acad. Sci. USA 105, 13987-13992.

Xiong, M., Dong, H., Siu, H., Peng, G., Wang, Y., and Jin, L. (2010). Genome-Wide Association Studies of Copy Number Variation in Glioblastoma. Proceedings of the 4th International Conference on Bioinformatics and Biomedical Engineering (iCBBE), 1-4.

Yacubova, E., and Komuro, H. (2002). Stage-specific control of neuronal migration by somatostatin. Nature 415, 77-81.

Zahn, J. M., Poosala, S., Owen, A. B., Ingram, D. K., Lustig, A., Carter, A., Weeraratna, A. T., Taub, D. D., Gorospe, M., Mazan-Mamczarz, K., et al. (2007). AGEMAP: a gene expression database for aging in mice. PLoS Genet. 3, e201.

Zou, H., and Hastie, T. (2005). Regularization and variable selection via the elastic net. J. R. Stat. Soc. Series B Stat. Methodol. 67, 301-320.

Example 2

Building a Methylation Model of Aging

We measured the methylation states of 485,577 CpG markers in genomic DNA collected from whole blood samples of 302 Caucasian individuals. Of these, 80 individuals had been diagnosed with type-2 diabetes, 22 of which were also characterized with diabetic nephropathy. For further study and validation, the methylation states of a second cohort were obtained, consisting of 188 Hispanic individuals. Everyone in the second cohort was diagnosed with type-2 diabetes, and 89 individuals also had diabetic nephropathy. Careful filtering and normalization was performed to remove the effects of gender, batch, and other unknown covariates.

In general, we assume biological activity will track with chronological age, allowing us to infer a biological model from chronological age. We hypothesize that changes in molecular activity from a common baseline will reflect a deceleration or acceleration of the aging process, to which disease, environment, and genetics might contribute.

Formally, we define biological age (bioage) as:

$$Bioage = f(M_{sub}) = Age + \sum_{j=1}^{f} \alpha_j c_j + \varepsilon$$

where $M_{sub}$ is a small subset of the methylation data, $\alpha_j$ is a numerical coefficient, $c_j$ is the j-th trait, and $\varepsilon$ is model error. A critical point here is that by selecting model probes that are coordinately linked to chronological aging, alterations to the methyl states corresponding to these same probes are likely to reflect either attenuation or amplification of the aging process.

We considered that the rate of biological aging is not constant, and that during different milestones of human development and senescence large shifts in biological aging will occur. We tested this hypothesis by first using a univariate association test, to identify the top age-associated methylation markers in the primary cohort (FDR<0.05). We then measured the relative coherence of these markers between young and old individuals using an entropy metric (FIG. 1). We found that the associated markers were much more coherent in the young individuals than in the old individuals (p<0.05). This suggests that methylation aging patterns are similar for young individuals, but diverge over time.

What is claimed is:

1. A method for detecting the methylation status of a set of age-associated epigenetic makers from a subject in relation to an age correlated reference population, said method comprising:

(a) isolating genomic or nuclear DNA from a biological sample obtained from a subject; and (b) detecting the methylation status of a set of age-associated epigenetic markers from the genomic DNA or nuclear DNA isolated from the subject's sample in relation to the methylation status of the same set of age-associated epigenetic markers from an age correlated reference population, wherein the set of age-associated epigenetic markers are selected from:
epigenetic markers of FIG. 9 of cg0440972, cg09809672, cg10501210, cg16054275, cg20822990, cg22512670, cg25410668, cg02085953, cg06639320, cg22016779, cg22158769, cg22454769, cg23606718, cg24079702, ch.2.30415474F, cg00481951, cg03607117, cg04474832, cg07553761, cg25478614, cg02650266, cg25428494, cg08234504, cg23500537, cg00486113, cg06493994, cg06685111, cg13001142, cg16867657, cg20052760, cg22736354, cg03473532, cg07927379, cg07955995, cg08097417, cg08540945, cg14361627, cg20426994, cg22285878, cg07583137, cg16419235, cg19935065, cg22796704, cg02046143, cg04940570, cg06419846, cg11067179, cg22213242, cg23091758, cg23744638, cg00748589, cg01528542, cg18473521, cg19722847, ch.13.39564907R, cg03032497, cg03399905, cg04875128, cg09651136, cg21296230, cg104416734, cg07082267, cg102867102, cg106874016, cg14692377, cg21139312, cg19283806, cg14556683, cg07547549, cg05442902, and cg08415592;
epigenetic markers of Table 3 of cg20822990, cg22512670, cg25410668, cg04400972, cg16054275, cg10501210, cg09809672, ch.2.30415474F, cg22158769, cg02085953, cg06639320, cg22454769, cg24079702, cg23606718, cg22016779, cg04474832, cg03607117, cg07553761, cg00481951, cg25478614, cg25428494, cg02650266, cg08234504, cg23500537, cg20052760, cg16867657, cg22736354, cg06493994, cg06685111, cg00486113, cg13001142, cg20426994, cg14361627, cg08097417, cg07955995, cg22285878, cg03473532, cg08540945, cg07927379, cg16419235, cg07583137, cg22796704, cg19935065, cg23091758, cg23744638, cg04940570, cg11067179, cg22213242, cg06419846, cg02046143, cg00748589, cg19722847, cg18473521, cg01528542, ch.13.39564907R, cg03032497, cg04875128, cg21296230, cg09651136, cg03399905, cg04416734, cg07082267, cg14692377, cg06874016, cg21139312, cg02867102, cg19283806, cg14556683, cg07547549, cg05442902, cg08415592, and cg24724428; and/or
epigenetic markers of Table 5 of cg23040782, cg11197101, cg00252781, cg16909962, cg23606718, cg03545227, cg00702638, cg05555455, cg03844506, cg16558177, cg11299854, cg05708550, cg16867657, cg22736354, cg14848772, cg115623062, cg116489193, cg118468088, cg104911280, cg119291355, cg105917988, cg20160885, cg19230755, cg09941452, cg26830108, cg19273773, cg14361627, cg08097417, cg02821342, cg07392449, cg08318076, cg02560186, cg08715791, cg23156348, cg10820926, cg06121469, cg07477282, cg21801378, cg02331561, cg06144905, cg14692377, cg18569335, cg26147554, cg21927946, cg15789607, cg12589298, cg06458239, cg10729426, cg26734668, and cg22888484, and
wherein the set of epigenetic markers further comprise the epigenetic markers of cg05652533, cg18404041, and cg27367526.

2. The method of claim 1, wherein in (b), detecting the methylation status of a set of age-associated epigenetic markers comprises:
(i) analyzing the methylation status at the C position of a CpG dinucleotide in the isolated genomic DNA or nuclear DNA of the sample by detecting the presence of a cytosine or uracil, the presence of cytosine or uracil indicating presence of a 5-methylcytosine or unmodified cytosine, respectively, in the original CpG dinucleotide; and
(ii) determining proportion of 5-methylcytosine or unmodified cytosine initially present at each age-associated epigenetic marker from (i); or alternatively, determining the ratio of 5-methyl-cytosine to unmodified cytosine or the ratio of unmodified cytosine to 5-methyl-cytosine initially present at each age-associated epigenetic marker from (i).

3. The method of claim 2, wherein the ratio of unmodified cytosine to 5-methylcytosine initially present at each age-associated epigenetic marker is the ratio of thymidine to cytosine at pyrimidine position of the CpG dinucleotide after hybridization to one or more probes, and analyzing the products generated by nucleic acid amplification.

4. The method of claim 2, wherein analyzing the methylation status in step (i) comprises DNA amplification and analysis of age-associated epigenetic marker for specific DNA end(s) or fragment(s) due to cleavage by the restriction enzyme(s) and for intact restriction enzyme cleavage sites associated at a particular age-associated epigenetic marker.

5. The method of claim 1, wherein in (b), the set of age-associated epigenetic markers comprises five or more, ten or more, fifteen or more, twenty or more, twenty-five or more, thirty or more, thirty-five or more, forty or more, forty-five or more, fifty or more, fifty-five or more, sixty or more, sixty-five or more, or seventy or more age-associated epigenetic markers.

6. The method of claim 1, wherein the biological sample is blood, lymphocyte, monocyte, neutrophil, basophil, eosinophil, myeloid lineage cell, lymphoid lineage cell, bone marrow, saliva, buccal swab, nasal swab, urine, fecal material, hair, breast tissue, ovarian tissue, uterine tissue, cervical tissue, prostate tissue, testicular tissue, brain tissue, neuronal cell, astrocyte, liver tissue, kidney, thyroid tissue, stomach tissue, intestine tissue, pancreatic tissue, vascular tissue, skin, lung tissue, bone tissue, cartilage, ligament, tendon, fat cells, muscle cells, neurons, astrocytes, cultured cells with different passage number, cancer/tumor cells, cancer/tumor tissue, normal cells, normal tissue, any tissue(s) or cell(s) with a nucleus containing genetic material, or genetic material in the form of DNA.

7. The method of claim 1, wherein the set of markers further comprises one or more of cg24724428, cg16419235, cg22454769, cg24079702, cg23606718, cg16867657, cg04474832, cg05442902, cg06493994, cg09809672, cg19722847, cg22736354, cg23606718, and/or cg16867657.

8. The method of claim 1, wherein in (b), detecting the methylation status of a set of age-associated epigenetic markers comprises:
hybridizing the isolated genomic DNA or nuclear DNA with two site-specific probes for each age-associated epigenetic marker, wherein the each of the two site-specific probes differentially react with unmodified and 5-methyl-modified cytosine;
amplifying the hybridized probe/DNA;
digesting the amplified DNA with one or more restriction enzymes that recognize a restriction enzyme site that contains a CpG dinucleotide but fails to digest the restriction enzyme site mutated to TpG dinucleotide from a CpG dinucleotide;
determining the proportion of 5-methylcytosine or unmodified cytosine initially present at each age-associated epigenetic marker based on the fraction or percentage of restriction enzyme sites sensitive or resistant to digestion; or alternatively, determining the ratio of 5-methylcytosine to unmodified cytosine initially present at each age-associated epigenetic marker based on the ratio of number or concentration of sensitive restriction enzyme sites to number or concentration of resistant restriction enzyme sites; or alternatively, determining the ratio of unmodified cytosine to 5-methylcytosine initially present at each age-associated epigenetic marker based on the ratio of number or concentration of resistant restriction enzyme sites to number or concentration of sensitive restriction enzyme sites to digestion.

9. The method of claim 1, wherein in (b), detecting the methylation status of a set of age-associated epigenetic markers:

fragmenting the genomic DNA or nuclear DNA;

exposing the fragmented DNA to a 5-methylcytosine-binding protein;

separating 5-methylcytosine-binding protein-bound DNA fragments from 5-methylcytosine-binding protein-free DNA fragments;

determining for each age-associated epigenetic marker, the proportion of 5-methyl-cytosine-containing DNA fragments or unmodified cytosine-containing DNA fragments by determining the fraction or percent of 5-methylcytosine-binding protein bound or free DNA fragments, respectively, for each age-associated epigenetic marker; or alternatively, determining for each age-associated epigenetic marker, the ratio of 5-methylcytosine-containing DNA fragments to unmodified cytosine-containing DNA fragments by determining the ratio of number or concentration of 5-methylcytosine-binding protein-bound DNA fragments to the number or concentration of 5-methylcytosine-binding protein-free DNA fragments; or alternatively, determining for each age-associated epigenetic marker, the ratio of unmodified cytosine-containing DNA fragments to 5-methylcytosine-containing DNA fragments by determining the ratio of number or concentration of 5-methylcytosine-binding protein-free DNA fragments to the number or concentration of 5-methylcytosine-binding protein-bound DNA fragments for each age-associated epigenetic marker, thereby determining the methylation status.

\* \* \* \* \*

UNITED STATES PATENT AND TRADEMARK OFFICE
CERTIFICATE OF CORRECTION

PATENT NO. : 10,087,486 B2
APPLICATION NO. : 14/442089
DATED : October 2, 2018
INVENTOR(S) : Kang Zhang et al.

Page 1 of 1

It is certified that error appears in the above-identified patent and that said Letters Patent is hereby corrected as shown below:

In the Specification

Column 1, Line 5, please replace the paragraph as follows:
--STATEMENT OF GOVERNMENT SPONSORED RESEARCH
This invention was made with Government support under Grant Nos. GM085764, ESO14811, EY014428, EY018660, EY019270 and EY021374 awarded by the National Institutes of Health (NIH). The government has certain rights in the invention.--

Signed and Sealed this
Twentieth Day of November, 2018

Andrei Iancu
*Director of the United States Patent and Trademark Office*